(12) United States Patent
Kadlec et al.

(10) Patent No.: US 10,441,527 B2
(45) Date of Patent: Oct. 15, 2019

(54) FLUID COMPOSITIONS AND PERSONAL CARE

(71) Applicant: Dow Silicones Corporation, Midland, MI (US)

(72) Inventors: Donald Kadlec, Midland, MI (US); Zhi Li, Midland, MI (US); Kimmai Thi Nguyen, Midland, MI (US); Ryan Christopher Thomas, Freeland, MI (US); Jason A Vogel, Freeland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 15/559,442

(22) PCT Filed: Apr. 4, 2016

(86) PCT No.: PCT/US2016/025831
§ 371 (c)(1),
(2) Date: Sep. 19, 2017

(87) PCT Pub. No.: WO2016/164292
PCT Pub. Date: Oct. 13, 2016

(65) Prior Publication Data
US 2018/0078486 A1  Mar. 22, 2018

Related U.S. Application Data

(60) Provisional application No. 62/144,669, filed on Apr. 8, 2015.

(51) Int. Cl.
| | |
|---|---|
| *A61K 8/894* | (2006.01) |
| *A61K 8/891* | (2006.01) |
| *A61K 8/898* | (2006.01) |
| *A61Q 19/00* | (2006.01) |
| *A61K 8/04* | (2006.01) |
| *A61K 8/81* | (2006.01) |

(52) U.S. Cl.
CPC ............. *A61K 8/894* (2013.01); *A61K 8/04* (2013.01); *A61K 8/8152* (2013.01); *A61K 8/891* (2013.01); *A61K 8/898* (2013.01); *A61Q 19/00* (2013.01); *A61K 2800/10* (2013.01)

(58) Field of Classification Search
CPC ........ A61K 8/585; A61K 8/891; A61K 8/898; C08G 77/70; C08G 77/26
See application file for complete search history.

(56) References Cited

U.S. PATENT DOCUMENTS

| | | |
|---|---|---|
| 2,814,601 A | 11/1957 | Currie et al. |
| 3,046,250 A | 7/1962 | Plueddemann |
| 3,159,601 A | 12/1964 | Ashby |
| 3,220,972 A | 11/1965 | Lamoreaux |
| 3,296,291 A | 1/1967 | Chalk et al. |
| 3,419,593 A | 12/1968 | Willing |
| 3,516,946 A | 6/1970 | Modic |
| 3,715,334 A | 2/1973 | Karstedt |
| 3,814,730 A | 6/1974 | Karstedt |
| 3,923,705 A | 12/1975 | Smith |
| 3,928,629 A | 12/1975 | Chandra et al. |
| 3,989,668 A | 11/1976 | Lee et al. |
| 4,122,029 A | 10/1978 | Gee et al. |
| 4,218,250 A | 8/1980 | Kasprzak |
| 4,311,695 A | 1/1982 | Starch |
| 5,036,117 A | 7/1991 | Chung et al. |
| 5,175,325 A | 12/1992 | Brown et al. |
| 5,302,382 A | 4/1994 | Kasprzak |
| 5,387,417 A | 2/1995 | Rentsch |
| 5,505,937 A | 4/1996 | Castrogiovanni et al. |
| 5,811,487 A | 9/1998 | Schulz, Jr. et al. |
| 5,891,954 A | 4/1999 | Gee et al. |

(Continued)

FOREIGN PATENT DOCUMENTS

| | | |
|---|---|---|
| EP | 0709083 | 5/1996 |
| EP | 1266647 | 12/2002 |

(Continued)

OTHER PUBLICATIONS

Scientific Literature Review (2012) (http://www.cir-safety.org/sites/default/files/Dimeth032012SLR_forposting.pdf).*
Search report from corresponding Japanese 2017-551630 application, dated Oct. 5, 2018.
Mintel, "Milano Cosmetic Set", Dec. 2008 (Dec. 2008), XP002758599.
Mintel, "Eye & Lip Serum-in-blur", Oct. 2014 (Oct. 2014), XP002758600.
Search report from corresponding Japanese 2017-551630 application, dated Mar. 22, 2019.
JPO2017551630, ShinEtsu, Silicone Gels KSG-Z Series, May 2012.
JPO2017551630, ShinEtsu, Silicone Gels KSG-Z Series, May 2012 with English translation.

*Primary Examiner* — Kuo Liang Peng

(57) ABSTRACT

A fluid composition comprises I) a first component and II) second component different from the first component I). The first component I) comprises at least one copolymer. The copolymer can include a cross-linked siloxane (e.g. a cross-linked aminosiloxane), a silicone polyether copolymer (e.g. an $(AB)_n$ silicone polyether copolymer), and/or a saccharide siloxane copolymer. The second component II) comprises an organopolysiloxane resin (e.g. an MQ resin) and/or an acrylate copolymer. The fluid composition can further comprise a carrier fluid, such as a silicone, an organic solvent, and/or an organic oil. The fluid composition may have a viscosity of at least 100 mPa·s at 23° C. and exhibit pituitous rheological properties (generally determined from a plot of normal force (in Pascals) vs a perpendicular shear rate in $(sec^{-1})$). Also disclosed is a personal care composition that comprises the fluid composition.

10 Claims, 11 Drawing Sheets

(56) References Cited

U.S. PATENT DOCUMENTS

| | | |
|---|---|---|
| 5,919,441 A | 7/1999 | Mendolia et al. |
| 5,948,855 A | 9/1999 | Lin et al. |
| 5,981,680 A | 11/1999 | Petroff et al. |
| 6,051,216 A | 4/2000 | Barr et al. |
| 6,071,503 A | 6/2000 | Drechsler et al. |
| 6,074,654 A | 6/2000 | Drechsler et al. |
| 6,075,087 A | 6/2000 | Juen et al. |
| 6,124,490 A * | 9/2000 | Gormley .............. A61K 8/0208 106/287.11 |
| 6,133,370 A | 10/2000 | Gutek et al. |
| 6,139,823 A | 10/2000 | Drechsler et al. |
| 6,180,117 B1 | 1/2001 | Berthiaume et al. |
| 6,200,581 B1 | 3/2001 | Lin et al. |
| 6,306,992 B1 | 10/2001 | Yoshitake et al. |
| 6,420,504 B1 | 7/2002 | Yoshitake et al. |
| 6,605,734 B2 | 8/2003 | Roy et al. |
| 6,653,378 B2 | 11/2003 | Ferritto et al. |
| 6,803,399 B2 | 10/2004 | Ferritto et al. |
| 6,967,024 B2 | 11/2005 | Scancarella et al. |
| 6,987,157 B2 | 1/2006 | Clement et al. |
| 6,991,782 B2 | 1/2006 | Kanji et al. |
| 7,238,768 B2 | 7/2007 | Hupfield et al. |
| 7,452,849 B2 | 11/2008 | Berry et al. |
| 7,781,505 B2 | 8/2010 | Cook et al. |
| 7,790,827 B2 | 9/2010 | Nguyen et al. |
| 7,803,358 B2 | 9/2010 | Gordan et al. |
| 7,834,087 B2 | 11/2010 | Joffre et al. |
| 7,871,633 B2 | 1/2011 | Bekele et al. |
| 7,887,834 B2 | 2/2011 | Lin et al. |
| 8,008,407 B2 | 8/2011 | Oberhellman et al. |
| 8,012,544 B2 | 9/2011 | Liu |
| 8,013,097 B2 | 9/2011 | Kennan et al. |
| 8,017,712 B2 | 9/2011 | Berry et al. |
| 8,071,079 B2 | 12/2011 | DeCaire et al. |
| 8,557,230 B2 | 10/2013 | Bui et al. |
| 8,586,013 B2 | 11/2013 | Bradshaw et al. |
| 8,603,444 B2 | 12/2013 | Bui |
| 8,673,282 B2 | 3/2014 | Bui et al. |
| 8,673,283 B2 | 3/2014 | Bui et al. |
| 8,673,284 B2 | 3/2014 | Bui et al. |
| 8,734,767 B2 | 5/2014 | Johnson et al. |
| 8,758,739 B2 | 6/2014 | Bui et al. |
| 8,778,323 B2 | 7/2014 | Bui et al. |
| 8,853,372 B2 | 10/2014 | Beck et al. |
| 8,877,216 B2 | 11/2014 | Joffre et al. |
| 8,907,026 B2 | 12/2014 | Joffre et al. |
| 9,181,434 B2 | 11/2015 | Shikano et al. |
| 9,260,607 B2 | 2/2016 | Iimura et al. |
| 9,714,323 B2 | 7/2017 | Kadlec et al. |
| 2002/0086935 A1 | 7/2002 | Ferritto et al. |
| 2003/0072730 A1 | 4/2003 | Tournilhac |
| 2003/0170188 A1 | 9/2003 | Ferrari et al. |
| 2003/0235552 A1 | 12/2003 | Yu |
| 2003/0235553 A1 | 12/2003 | Lu et al. |
| 2004/0180032 A1 | 9/2004 | Manelski et al. |
| 2006/0079415 A1 | 4/2006 | Kozubal et al. |
| 2006/0111452 A1 | 5/2006 | Wallace et al. |
| 2006/0269506 A1 | 11/2006 | De Caire et al. |
| 2007/0166263 A1 | 7/2007 | Lin |
| 2007/0243241 A1 | 10/2007 | Lin et al. |
| 2008/0138386 A1 | 6/2008 | Joffre et al. |
| 2009/0036615 A1 | 2/2009 | Miyadai et al. |
| 2009/0258058 A1 | 10/2009 | Thomas et al. |
| 2010/0048795 A1 | 2/2010 | Kennan et al. |
| 2010/0184935 A1 | 7/2010 | Oberhellman et al. |
| 2010/0233104 A1 | 9/2010 | Drake et al. |
| 2011/0150818 A1 | 6/2011 | Canfield et al. |
| 2011/0189248 A1 | 8/2011 | Baldaro et al. |
| 2011/0245374 A1 | 10/2011 | Barnes et al. |
| 2012/0156148 A1 | 6/2012 | Shikano et al. |
| 2012/0171137 A1 | 7/2012 | Bradsaw et al. |
| 2012/0220549 A1 | 8/2012 | Starch et al. |
| 2012/0251605 A1 * | 10/2012 | Iimura ................ A61K 8/0241 424/401 |
| 2013/0030131 A1 | 1/2013 | Deeth et al. |
| 2013/0149259 A1 | 6/2013 | Delvalle et al. |
| 2013/0149260 A1 | 6/2013 | Delvalle et al. |
| 2013/0149261 A1 | 6/2013 | Delvalle et al. |
| 2014/0249106 A1 | 9/2014 | Starch et al. |
| 2014/0357884 A1 | 12/2014 | Joffre et al. |
| 2016/0262991 A1 | 9/2016 | Akabane et al. |

FOREIGN PATENT DOCUMENTS

| | | |
|---|---|---|
| EP | 1266648 | 12/2002 |
| EP | 1266653 | 12/2002 |
| JP | 61158913 | 7/1986 |
| JP | 61161211 | 7/1986 |
| JP | 6118708 | 4/1994 |
| JP | 2010184885 | 8/2010 |
| JP | 2013103885 | 5/2013 |
| WO | 03105789 | 12/2003 |
| WO | 03106614 | 12/2003 |
| WO | 2004000247 | 12/2003 |
| WO | 2004054523 | 7/2004 |
| WO | 2004054524 | 7/2004 |
| WO | 2004060101 | 7/2004 |
| WO | 2004060271 | 7/2004 |
| WO | 2005103117 | 11/2005 |
| WO | 2006127883 | 11/2006 |
| WO | 2010149493 | 12/2010 |
| WO | 2011078408 | 6/2011 |
| WO | 2013103832 | 7/2013 |
| WO | 2013117490 | 8/2013 |
| WO | 2015066165 | 5/2015 |
| WO | 2016014127 | 1/2016 |
| WO | 2016014128 | 1/2016 |

* cited by examiner

Cross-linked siloxane network with cationic groups (secondary amines) & anionic groups (COOH)

Cross-linked siloxane network with cationic groups (secondary & quaternary amines)

FLUID COMPOSITIONS AND PERSONAL CARE

CROSS REFERENCE TO RELATED APPLICATIONS

This application is a U.S. national stage filing under 35 U.S.C. § 371 of PCT Application No. PCT/US16/025831 filed on 4 Apr. 2016, currently pending, which claims the benefit of U.S. Provisional Patent Application No. 62/144,669 filed 8 Apr. 2015 under 35 U.S.C. § 119 (e). PCT Application No. PCT/US16/025831 and U.S. Provisional Patent Application No. 62/144,669 are hereby incorporated by reference.

COMPOSITIONS COMPRISING THE SAME

This disclosure relates to fluid compositions comprising I) a first component comprising at least one copolymer and II) a second component different from the first component I) and comprising an organopolysiloxane resin, an acrylate copolymer, or a combination thereof. The fluid compositions generally exhibit pituitous rheological properties. This disclosure also relates to personal care compositions (e.g. cosmetic products or formulations) comprising the fluid compositions, which provide improved physical properties to the personal care compositions.

Consumer brands often use film formers and cosmetic oils to fill and smooth the surface of skin to conceal skin imperfections. The film formers generally improve transfer resistance and long wear of cosmetic products. In particular, silicone resins have been widely used in the beauty care industry to provide color cosmetics' transfer resistance and long wear. However, after drying and forming films on surfaces, silicone resins tend to be brittle and flake off. This phenomenon results in a need to use plasticizers, in combination with silicone resins, in order to render the resultant films more flexible and less susceptible to flake off.

To this end, a number of efforts have been made to identify suitable plasticizers for silicone resins. For instance, silicone gums of various molecular weights have been used in combination with silicone resins ("conventional combinations") for plasticizing silicone resins in dried films. However, other than film forming, conventional combinations provide very limited additional benefits to cosmetic formulations. In addition, conventional combinations' actual performance in cosmetic formulations is not quite predictable. In many cases, their performance can be further negatively impacted by a large amount of additional functional components (e.g. rheology modifiers) needed in the cosmetic formulations.

In view of the foregoing, there remains an opportunity to provide additional compositions that have desirable physical properties for use in personal care compositions. There also remains an opportunity to provide additional methods of forming such compositions and personal care compositions.

BRIEF SUMMARY OF THE INVENTION

Disclosed is a fluid composition. The fluid composition comprises I) a first component and II) a second component different form the first component I). The first component I) comprises at least one copolymer. The second component II) comprises an organopolysiloxane resin, an acrylate copolymer, or a combination thereof. The fluid composition generally exhibits pituitous rheological properties.

Pituitous fluids are fluids that display particular types of rheological behavior. The most easily recognized rheological behavior for pituitous fluids is their "stringing" behavior, which is the formation of thin strings or threads when a small amount of the pituitous fluid is separated from the bulk of the fluid. The fluid compositions of this disclosure are often highly lubricious yet form very persistent films on surfaces. As the fluid compositions are sheared, the normal force developed resists thinning of the fluid composition, thereby maintaining a thicker lubrication layer between the moving surfaces. Other benefits are described below.

Also disclosed is a personal care composition. The personal care composition comprises the fluid composition of this disclosure. The fluid composition provides personal care compositions with enhanced aesthetic and sensory properties. For example, the fluid compositions can form a pseudo-film on skin. This provides improved coverage on skin and longer lasting physical properties. Furthermore, the fluid compositions may provide enhanced film formation of various personal care actives upon application to skin. For example, the SPF performance of sunscreens may be enhanced when delivered with the fluid compositions.

To their surprise, the inventors of the fluid compositions of this disclosure discovered a certain group of copolymers (i.e., the first component; e.g. aminosiloxane copolymers) capable of plasticizing a certain group of acrylate copolymers and polyorganosiloxane resins (i.e., the second component; e.g. MQ resins) that allow for the formation of flexible films with improved transfer resistance and long wear. Also to their surprise, the inventors discovered that their fluid compositions are capable of providing novel sensory profiles to cosmetic formulations, sebum resistance, and better formulation flexibility (e.g. the ability to maintain considerable formulation viscosity while incorporating additional solvent(s)).

Incorporation of their fluid compositions into personal care compositions also limits the usage of additional rheology modifiers and sensory modifiers that potentially provide negative impacts to lasting performance. So in addition to film forming benefits, the fluid compositions of this disclosure offer additional benefits for cosmetic formulations over conventional combinations, e.g. enabling lowered siloxane and film formers usage levels which provide lowered formulation cost and flexible viscosity control. In sum, the fluid compositions of this disclosure address one or more deficiencies of the prior art, and provide improved flexible films for more comfortable, improved transfer and sebum resistance, and longer wear, allowing cosmetic products utilizing the fluid compositions to retain their desired appearance and meet consumer needs.

BRIEF DESCRIPTION OF THE DRAWINGS

Other advantages of the present disclosure will be readily appreciated, as the same becomes better understood by reference to the following detailed description when considered in connection with the accompanying drawings wherein.

DETAILED DESCRIPTION

Figure 1:
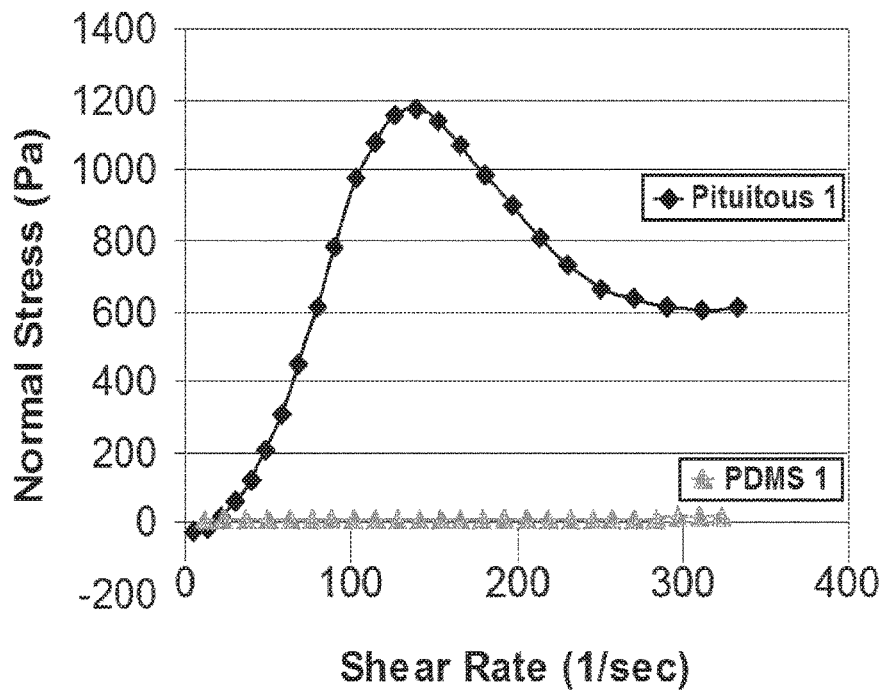
FIG. 1 is a line graph illustrating normal stress as a function of shear rate of a first pituitous fluid composition and a first polydimethylsiloxane ("PDMS")

This disclosure relates to a fluid composition ("composition"). The composition comprises I) a first component. The composition further comprises II) a second component different from the first component I). In various embodiments, the first component serves as a plasticizer for the second component. The composition may also include one or more additional components as disclosed herein. As detailed below, the composition generally exhibits pituitous rheological properties. The composition may also be referred to herein as the "silicone fluid", "fluid composition", "pituitous silicone composition", "pituitous silicone fluid", or "pituitous silicone fluid composition".

As used herein, "pituitous" describes a rheological property of the silicone fluid wherein the fluid exhibits an increasing normal stress observed in a perpendicular direction when a constantly increasing shear force is applied. For example, when the pituitous silicone fluid is subjected to shear stress in the x-y plane, a force is developed in the z direction (perpendicular or normal to the plane of shear). Pituitous rheology of the silicone fluid may be measured using a controlled stress rheometer. Such rheometers are commercially available, such as TA Instruments AR 1000-N (109 Lukens Drive, New Castle Del. 19720).

Typically, a fluid sample is held between a flat disc (attached to the rheometer) and a stationary plate equipped with a load cell. A controlled amount of force (torque) is applied to the shaft attached to the disc thus subjecting the sample to a shear stress. The torque is increased and the disc rotates at an increasing rate, which is recorded as the shear rate. As the sample is being subjected to the shear stress, the normal stress is recorded by the load cell. The results of the evaluations of the rheological properties are generally reported as a plot of normal stress (in Pascals) vs. a perpendicular shear rate (in $sec^{-1}$ or 1/sec).

In other embodiments, a fluid is considered pituitous if a plot of normal stress versus shear rate falls above a limit line on a graph wherein the limit line is created using the equation y=3.6x, where y in the normal stress and x is the shear rate. However, the results are not limited to such types of reporting and may be reported or evaluated using any technique appreciated in the art.

In various embodiments, the composition possesses rheological properties such that when a plot of normal force (in Pascals) vs a perpendicular shear rate (in $sec^{-1}$) is measured using a controlled stress rheometer as described above, the plot generally has an average slope that is >3.6 (based on the x-axis being 1/sec and the y-axis being Pa).

First Component:

The first component comprises at least one copolymer. Various types of copolymers can be utilized to form the composition; however, suitable copolymers generally include silicon-containing moieties, more typically siloxy-containing moieties. In various embodiments, the copolymer is selected from the group of cross-linked siloxanes, silicone polyether copolymers, saccharide siloxane copolymers, and combinations thereof.

The first component can be utilized in the composition in various amounts. Typically, the first component is present in an amount of from about 0.1-99.9, 1-99, 5-95, 10-90, 20-80, 30-70, 40-60, 45-55, or 50, wt % based on 100 parts by weight of the composition. It is contemplated that any and all values or ranges of values between those described above may also be utilized.

Non-Limiting Examples of Suitable Cross-Linked Siloxanes:

In certain embodiments, the copolymer of the first component comprises a cross-linked siloxane. Various types of cross-linked siloxanes can be used. Reaction schemes of different types can be utilized to obtain suitable cross-linked siloxanes, and many are commercially available (e.g. from Dow Corning Corporation of Midland, Mich.).

Typically, the cross-linked siloxane comprises an addition reaction product, alternatively a hydrosilylation reaction product. For example, the cross-linked siloxane can be obtained via amine/epoxy, anhydride/amine, anhydride/alcohol, or SiH/alkenyl, reactions as understood in the art. Other reaction schemes/products understood in the art can also be used, such as radical or condensation cure components/schemes. Non-limiting examples of suitable cross-linked siloxanes for forming the composition follow below.

First Non-Limiting Example of a Suitable Cross-Linked Siloxane:

The cross-linked siloxane can be a cross-linked aminosiloxane. Various types of cross-linked aminosiloxanes can be used. In certain embodiments, the cross-linked aminosiloxane comprises the reaction product of a) a polyorganosiloxane and b) a cross-linker. In general, there are at least two molecules of component a) for every molecule of component b). Various combinations and amounts of components a) and b) can be utilized, which can be used, for example, to impart various cross-link densities, residual functional groups (e.g. amino groups), different chemistries (inorganic and organic), etc.

Figure 2:
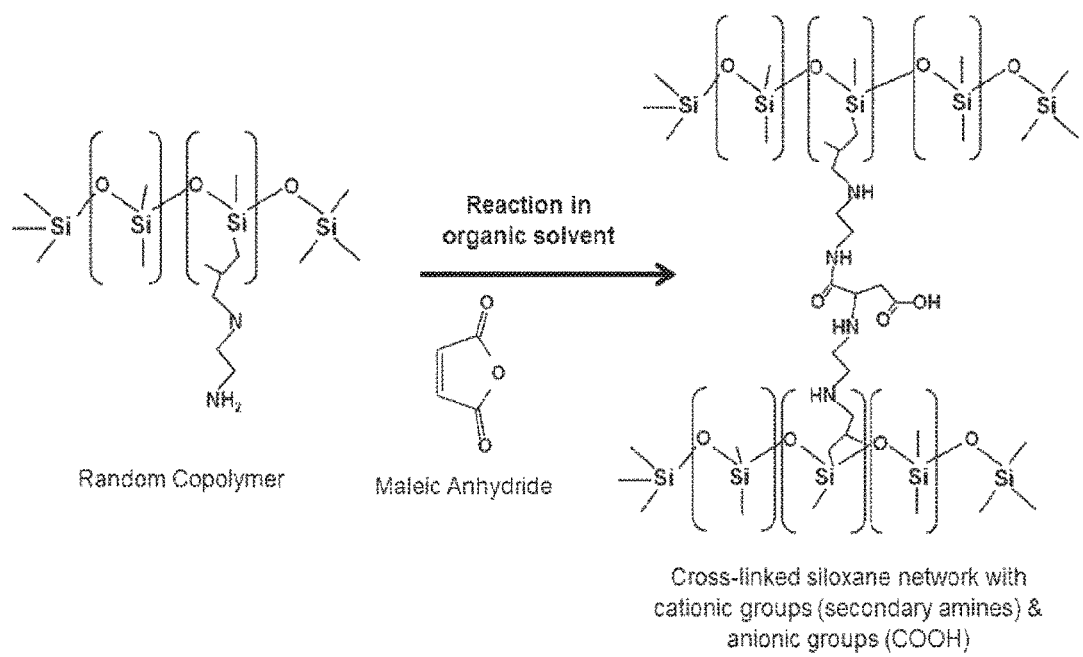
FIG. 2 is a general reaction scheme showing a non-limiting reaction of this disclosure utilizing an amino (or amine) functional polysiloxane and maleic anhydride to form a cross-linked aminosiloxane, with an organic solvent present during reaction.
Figure 3:
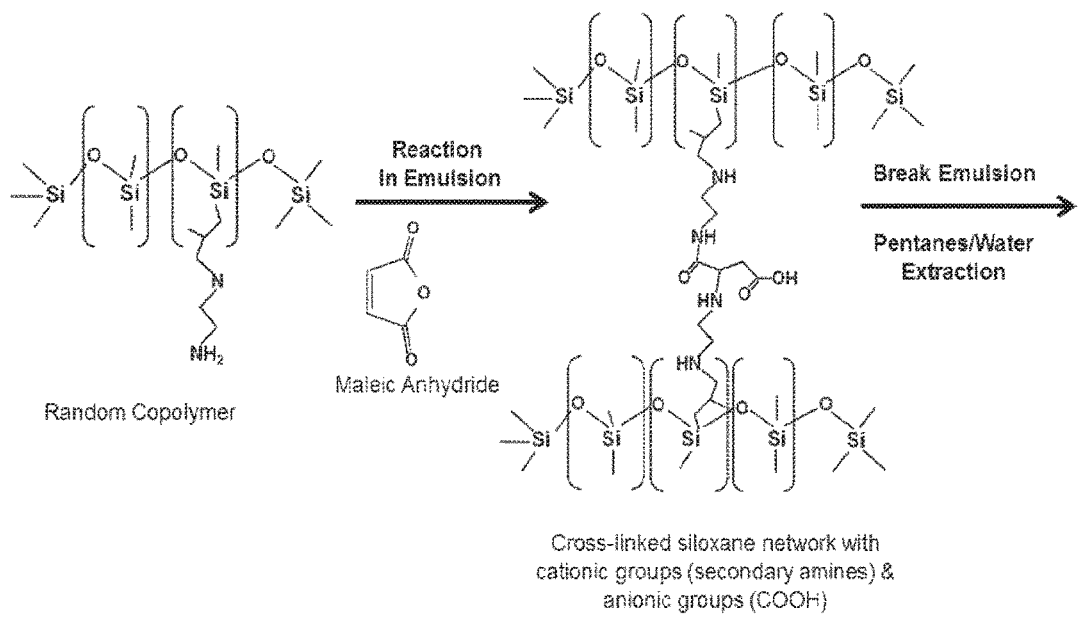
FIG. 3 is a general reaction scheme showing another non-limiting reaction of this disclosure utilizing an amino functional polysiloxane and maleic anhydride to form a cross-linked aminosiloxane, with an emulsion present during reaction.
Figure 4:
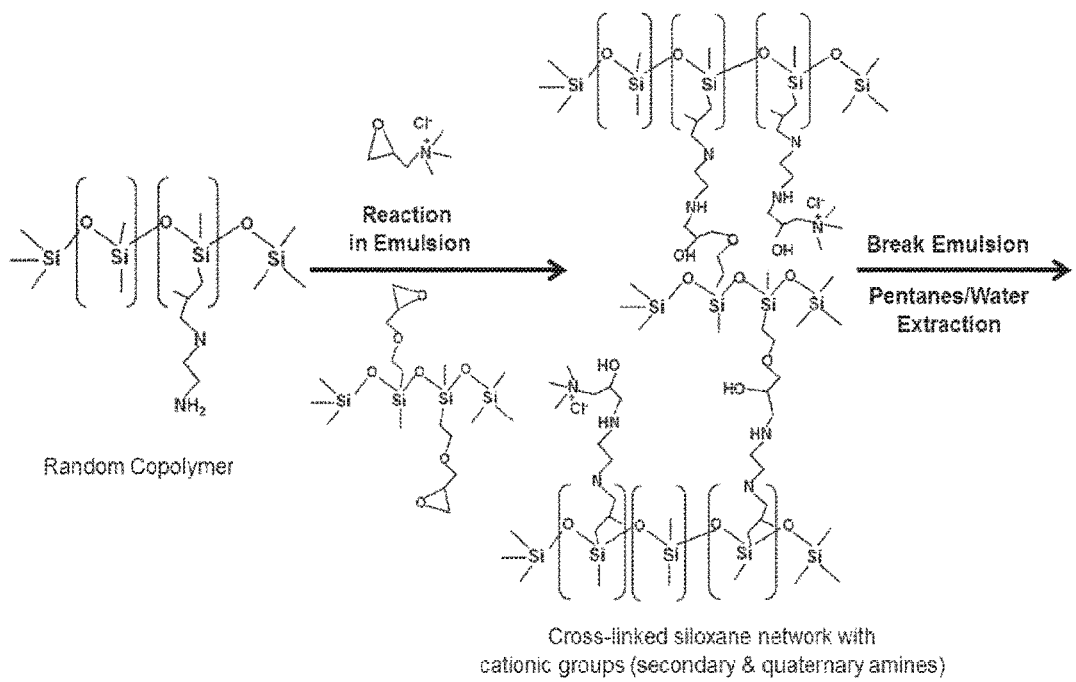
FIG. 4 is a general reaction scheme showing another non-limiting reaction of this disclosure utilizing an amino functional polysiloxane and epoxy (or epoxide) functional components to form a cross-linked aminosiloxane, with an emulsion present during reaction.

Example reaction schemes for forming cross-linked aminosiloxanes suitable for the composition of this disclosure are illustrated in FIGS. 2, 3 and 4. A specific example of a suitable cross-linked aminosiloxane is present in DOW CORNING® CE-7080 Smart Style (INCI Name: Silicone Quaternium-16/Glycidoxy Dimethicone Crosspolymer and Undeceth-11 and Undeceth-5).

In various embodiments, the polyorganosiloxane comprises siloxy units of the formula: $(R^1_3SiO_{1/2})_w(R^1R^2SiO_{2/2})_x(R^1_2SiO_{2/2})_y$, where each $R^1$ is an independently selected substituted or unsubstituted hydrocarbyl group; "w" is ≥2 or 2; "x" is ≥1, 1-1,000, 25-750, 50-500, or 100-250; "y" is ≥0, 0-1,000, 1-1,000, 25-750, 50-500, or 100-250; and (x+y) is ≥50, 50-2,000, 50-1,500, 50-1,000, 100-1,000, 100-750, or 200-500. It is contemplated that any and all values or ranges of values between those described above may also be utilized.

$R^1$ may be a substituted or unsubstituted aliphatic or aromatic hydrocarbyl. Monovalent unsubstituted aliphatic hydrocarbyls are exemplified by, but not limited to, alkyl groups, such as methyl, ethyl, propyl, pentyl, octyl, undecyl, and octadecyl; and cycloalkyl groups, such as cyclohexyl. Monovalent substituted aliphatic hydrocarbyls are exemplified by, but not limited to, halogenated alkyl groups, such as chloromethyl, 3-chloropropyl, and 3,3,3-trifluoropropyl. Aromatic hydrocarbyls are exemplified by, but not limited to, phenyl, tolyl, xylyl, benzyl, styryl, and 2-phenylethyl. In certain embodiments, each $R^1$ is an independently selected $C_1$-$C_6$ alkyl group, alternatively a methyl group.

Each $R^2$ is independently of the formula: —$R^3$—Z where $R^3$ is a divalent group and Z comprises at least nitrogen containing group. The cross-linker is reactive with the Z group of the polyorganosiloxane.

$R^3$ is a hydrocarbylene, a heterohydrocarbylene, or an organoheterylene group. Examples of $R^3$ include methylene, ethylene, propylene, hexamethylene, decamethylene, phenylene, naphthylene, —$CH_2CH(CH_3)CH_2$—, —$CH_2CH_2SCH_2CH_2$—, —$CH_2CH_2OCH_2$—, —$CH_2CH_2$—, —$OCH_2CH_2O$—, —$CH_2CH(CH_3)C(O)OCH_2$—, —$(CH_2)_3C(O)OCH_2CH_2$—, —$C_6H_4C_6H_4$—, —$C_6H_4CH_2C_6H_4$—, and —$(CH_2)_3C(O)SCH_2CH_2$—.

In various embodiments, Z is an organic amino functional radical containing ≥1 amino functionality. One possible formula for Z is: —$NH(CH_2)_zNH_2$ where "z" is ≥1. Another possible formula for Z: is —$N(CH_2)_z(CH_2)_{zz}NH$ where both "z" and "zz" are independently ≥1, this structure encompassing diamino ring structures, such as piperazinyl.

In certain embodiments, Z is of the formula: —$(NH)_z(CH_2)_{zz}NHR^4$ where "z" is 1 or 0; "zz" is 0, ≥1, ≥2, or 2; and $R^4$ is hydrogen or a substituted or unsubstituted hydrocarbyl group. In specific embodiments, $R^3$ is —$CH_2CH(CH_3)CH_2$—, "z" is 1, "zz" is 2, and $R^4$ is hydrogen. It is contemplated that any and all values or ranges of values between those described above may also be utilized.

Examples of suitable amino functional polyorganosiloxanes for forming the cross-linked aminosiloxane are illustrated in FIGS. 2, 3 and 4. A specific example of a suitable polyorganosiloxane for forming the cross-linked aminosiloxane is DOW CORNING® 2-8566 (INCI Name: Amodimethicone).

The cross-linker can be of various functionalities provided that it is reactive with the amino groups of the polyorganosiloxane. Suitable functionalities of the cross-linker include, but are not limited to, anhydride and epoxy functionality. Examples of suitable cross-linkers for forming the cross-linked aminosiloxane are illustrated in FIGS. 2, 3 and 4. A specific example of a suitable cross-linker is maleic anhydride.

In various embodiments, the cross-linker comprises siloxy units of the formula: $(R^1_3SiO_{1/2})_j(R^1R^5SiO_{2/2})_k(R^1_2SiO_{2/2})_l$ where each $R^1$ is an independently selected substituted or unsubstituted hydrocarbyl group; each $R^5$ independently comprises an epoxide group; "j" is ≥2 or 2, "k" is ≥2 or 2; and "l" is ≥0 or 0. Suitable hydrocarbyl group are described herein.

Components a) and b) can be used in various molar ratios to form the cross-linked aminosiloxane. Typically, components a) and b) are utilized in such amounts such that the residual amino content (imparted by $R^2$) is <2, <1, <0.5, <0.25, or 0, %.

In other embodiments, the cross-linked aminosiloxane is obtained by combining (i) an amine functional polysiloxane and (ii) an epoxy functional silicone containing at least two epoxy groups. The amine functional polysiloxane can have the formula:

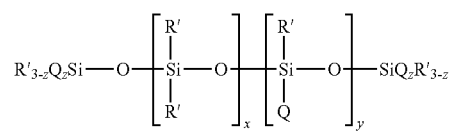

where R' denotes an alkyl group of 1-30 carbons, aryl group, aralkyl group, or alkaryl group, provided that at least 50% of the total number of R' groups are methyl; Q denotes an amine functional substituent of the formula: —R"Z where R" is a divalent alkylene radical of 3-6 carbon atoms. Z is a monovalent radical selected from the group of: —$NR_2'''$ and —$NR'''(CH_2)_bNR_2'''$; where R''' denotes hydrogen or an alkyl group of 1-4 carbons, "b" is 2-6; "z" is 0 or 1; "x" is 25-3,000, 25-2,000, or 25-1,000; and "y" is 0-3,000, 0-2,000, or 0-1,000 when "z" is 1 or is 1-3,000, 1-2,000, or 1-1,000 when "z" is 0.

Suitable R' groups are methyl, ethyl, propyl, isopropyl, butyl, isobutyl, phenyl, xenyl, benzyl, phenylethyl, and tolyl, with the proviso that at least 50% of the R' groups are methyl. The alkylene radicals represented by R" may include trimethylene, tetramethylene, pentamethylene, —$CH_2CH(CH_3)CH_2$—, and —$CH_2CH_2CH(CH_3)CH_2$—.

Alkyl groups of 1-4 carbon atoms as represented by R''' include methyl, ethyl, propyl, isopropyl, butyl, and isobutyl. Useful Z radicals include the unsubstituted amine radical —$NH_2$; alkyl substituted amine radicals, such as —$NHCH_3$, —$NHCH_2CH_2CH_2CH_3$, and —$N(CH_2CH_3)_2$; and aminoalkyl substituted amine radicals, such as —$NHCH_2CH_2NH_2$, —$NH(CH_2)_6NH_2$, and —$NHCH_2CH_2CH_2N(CH_3)_2$.

When "z" is 0, the amine functional polysiloxane has only pendent amine functional substituents in the polymer chain. When "z" is 1, the amine functional polysiloxane may have only terminal amine functional substituents or both terminal and pendent amine functional substituents in the polymer chain. Typically, "x" is 25-500, and y is 0-100 when "z" is 1 and 1-100 when "z" is 0. In general, x+y is about 50-1,000, 50-750, 50-500, or 50-250.

The amine content, i.e., the number of amine functional groups in the molecule of the amine functional polysiloxane, is generally expressed as mol percent amine, and this is determined according to the relationship y/DP×100, where "y" is in the above formula, and the Degree of Polymerization (DP) is (x+y+2) which indicates the chain length of the amine functional polysiloxane. Such amine functional polysiloxanes are well known in the art and available commercially, such as from Dow Corning Corporation.

When it is desirable to use an epoxy functional silicone containing at least two epoxy groups, a suitable epoxy functional silicone of the general structure shown below can be used, in which "x" is ≥1:

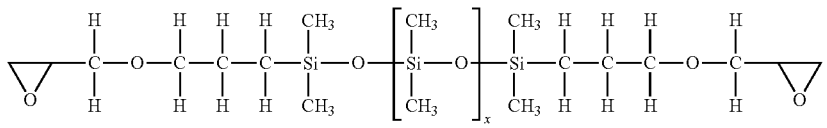

Such epoxy functional silicones are well known in the art and available commercially, such as from Dow Corning Corporation. Typically, such epoxy functional silicones have a viscosity ranging from about 1-200 mm²/s and molecular weights of about 300-6,000. Other suitable epoxy functional cross-linkers are illustrated in FIG. 4. If desired, organic epoxides and epoxy functional silicones containing a single epoxy group can be included as an additional component, in order to control the cross-link density and the overall molecular weight of the cross-linked aminosiloxane.

Other cross-linked siloxanes and/or components that may be used to form the compositions and/or personal care compositions of this disclosure are described in U.S. Pat. Nos. 3,046,250; 5,948,855; 6,180,117; 6,653,378; 6,803,399; 7,238,768; 7,781,505; 8,013,097; and 8,071,079; and US Pub Nos. 2002/0086935; 2006/0111452; 2006/0269506; 2009/0258058; 2010/0048795; 2010/0233104; 2011/0150818; and 2013/0030131; each of which is expressly incorporated herein by reference in one or more non-limiting embodiments.

Second Non-Limiting Example of a Suitable Cross-Linked Siloxane:

In certain embodiments, the cross-linked siloxane is a branched organopolysiloxane. The branched organopolysiloxane comprises the reaction product of a) a cyclic siloxane and b) a polyorganosiloxane, in the presence of a hydrosilylation catalyst. The branched organopolysiloxane may also be referred to herein as "component A)" or the "hydrosilylation reaction product". The hydrosilylation reaction product is generally formed from the hydrosilylation reaction of the cyclic siloxane and polyorganosiloxane.

One or more than one cyclic siloxane can be reacted with one or more than one polyorganosiloxane. Similarly, in various embodiments, one cyclic siloxane is reacted with two (or more) polyorganosiloxanes. Alternatively, two (or more) cyclic siloxanes may be reacted with one polyorganosiloxane. Thus, in various embodiments, wherever "cyclic siloxane" is used herein, two or more cyclic siloxanes can be used. In other embodiments, wherever "polyorganosiloxane" is used herein, two or more polyorganosiloxanes can be used.

The hydrosilylation reaction product typically includes alkenyl or Si—H functionality (e.g. as the result of the reaction of the cyclic siloxane and polyorganosiloxane). In various embodiments, the alkenyl or Si—H functionality may be observed on a parts per million (ppm) or parts per billion (ppb) level, based on a total weight of the hydrosilylation reaction product and/or composition. In other embodiments, the alkenyl or Si—H functionality is understood based on a molar ratio of alkenyl to Si—H functionality of the reactants (e.g. the cyclic siloxane and polyorganosiloxane) used to form the hydrosilylation reaction product. For example, the ratio of alkenyl to Si—H units used to form the hydrosilylation reaction product may be <1 or >1.

In various embodiments, this ratio is from 0.01 to <1, 0.1 to <1, 0.2-0.9, 0.3-0.8, 0.4-0.7, or 0.5-0.6. In other embodiments, this ratio is >1, from >1 to 100, >1 to 50, >1 to 25, >1 to 15, >1 to 10, or >1 to 5. Typically, the ratio of alkenyl to Si—H units is not exactly 1. However, a ratio of 1 is contemplated in one embodiment. It is contemplated that any and all values or ranges of values between those described above may also be utilized.

In various embodiments, the hydrosilylation reaction product is present in an amount of from about 0.1-50, 0.1-40, 1-37, 2-35, 3-30, 5-25, 5-20, 5-15, 5-10, 5-9, 6-9, or 7-8, wt % based on 100 parts by weight of the composition. This amount, in wt %, may also be described as a "percent solids" or "percent active(s)." It is contemplated that any and all values or ranges of values between those described above may also be utilized.

The hydrosilylation reaction product may be described as an elastomer, e.g. a loosely cross-linked elastomer. When combined with (and/or formed in the presence of) the carrier fluid (detailed below), the hydrosilylation reaction product is fairly soluble therein. The degree of polymerization of the hydrosilylation reaction product itself can depend on the degrees of polymerization of the cyclic siloxane and polyorganosiloxane. In various embodiments, a high degree of polymerization of both the cyclic siloxane and polyorganosiloxane imparts tight cross-linking to the hydrosilylation reaction product. In other embodiments, a high degree of polymerization of one or the other of the cyclic siloxane and polyorganosiloxane imparts a medium degree of cross-linking to the hydrosilylation reaction product. In still other embodiments, a low degree of polymerization of both the cyclic siloxane and polyorganosiloxane imparts a low, e.g. loose, degree of cross-linking to the hydrosilylation reaction product. In certain embodiments, the hydrosilylation reaction product is considered to be lightly cross-linked as understand by those skilled in the art.

Various types of cyclic siloxanes can be utilized to form the branched organopolysiloxane. The cyclic siloxane may also be referred to herein as "component a)". The cyclic siloxane has at least two silicon-bonded alkenyl groups per molecule. Suitable alkenyl groups are described herein.

In various embodiments, the cyclic siloxane has the formula: $[R^1R^2SiO]_g$ where each $R^1$ is an independently selected substituted or unsubstituted hydrocarbyl group; and "g" is ≥3, 3-10, 3-8, 3-6, or 4. It is contemplated that any and all values or ranges of values between those described above may also be utilized.

$R^1$ may be a substituted or unsubstituted aliphatic or aromatic hydrocarbyl. Monovalent unsubstituted aliphatic hydrocarbyls are exemplified by, but not limited to, alkyl groups, such as methyl, ethyl, propyl, pentyl, octyl, undecyl, and octadecyl; and cycloalkyl groups, such as cyclohexyl. Monovalent substituted aliphatic hydrocarbyls are exemplified by, but not limited to, halogenated alkyl groups, such as chloromethyl, 3-chloropropyl, and 3,3,3-trifluoropropyl. Aromatic hydrocarbyls are exemplified by, but not limited to, phenyl, tolyl, xylyl, benzyl, styryl, and 2-phenylethyl.

In various embodiments, each $R^1$ is a hydrocarbon group. Suitable hydrocarbon groups are described herein. In other embodiments, each $R^1$ is an independently selected alkyl group having from 1-8 carbon atoms, an aryl group, a carbinol group, or an amino group. Examples of such groups are described further below. In certain embodiments, each $R^1$ is an independently selected $C_1$-$C_6$ alkyl group, such as a methyl group. Alkenyl functional cyclic siloxanes are known, and there are many commercially available.

Each $R^2$ is $R^1$ or an alkenyl group, provided that at least two $R^2$ groups are alkenyl groups. In certain embodiments, each $R^2$ is an independently selected $C_2$-$C_{12}$ alkenyl group. Suitable alkenyl groups include vinyl, allyl, butenyl, pentenyl, hexenyl, and decenyl, groups. The alkenyl group is typically a vinyl or hexenyl group, more typically a vinyl group.

Various types of polyorganosiloxanes can be utilized to form the branched organopolysiloxane. The polyorganosiloxane may also be referred to herein as "component b)". The polyorganosiloxane has at least two silicon-bonded hydrogen atoms (or SiH groups) per molecule. The silicon-bonded hydrogen atoms of component b) are typically terminal.

In various embodiments, the polyorganosiloxane comprises siloxy units of the formula: $(R_2HSiO_{1/2})_v(R^2SiO_{2/2})_x$ where each R is independently selected substituted or unsubstituted hydrocarbyl group; "v" is ≥2 or 2; and "x" is ≥50 or ≥100, alternatively from 150-10,000, 200-7,500, 250-5,000, 300-2,500, 300-1,000, or 350-500. It is contemplated that any and all values or ranges of values between those described above may also be utilized.

Suitable substituted or unsubstituted hydrocarbyl groups for R include those described above for $R^1$. In certain embodiments, each R is an independently selected $C_1$-$C_6$ alkyl group, such as a methyl group.

The total number of siloxy units associated with subscript "x" may also be referred to as a degree of polymerization (DP) as understood in the art. The molecular weight, or the DP may vary provided that "x" is ≥50, otherwise the molecular weights are generally not limiting. However, when molecular weights become too high or if the polyorganosiloxane is a solid, it may be desirable to dilute component b) in a suitable solvent or lower molecular weight fluid, such as any of the carrier fluids described herein.

The polyorganosiloxane can be a homopolymer, a copolymer or a terpolymer containing such organic groups. Examples include copolymers comprising dimethylsiloxy units and phenylmethylsiloxy units, copolymers comprising dimethylsiloxy units and 3,3,3-trifluoropropylmethylsiloxy units, copolymers of dimethylsiloxy units and diphenylsiloxy units and interpolymers of dimethylsiloxy units, diphenylsiloxy units and phenylmethylsiloxy units, among others. The molecular structure is also not critical and is exemplified by straight-chain and partially branched straight-chain structures, the linear systems being the most typical. The polyorganosiloxane may be referred to as a SiH terminated polyorganosiloxane. SiH functional polyorganosiloxanes are known, and there are many commercially available.

The polyorganosiloxane may also contain other siloxy units, such as "T" units ($RSiO_{3/2}$) and "Q" siloxy units ($SiO_{4/2}$). In various embodiments, the polyorganosiloxane includes <1, <0.5, <0.1, or <0.01, weight percent of T and/or Q units. Alternatively, the polyorganosiloxane is free of T and/or Q units.

In one embodiment, the polydiorganosiloxane is selected from a SiH terminated polydiorganosiloxane gum. As used herein, polydiorganosiloxane gums include predominately D units. For example, the polydiorganosiloxane gum may itself have viscosity of at least 1,000,000, or at least 2,000,000, $mm^2/s$ at 25° C. Alternatively, the molecular weight may be sufficient to impart a Williams plasticity number of at least 40 as determined by the American Society for Testing and Materials (ASTM) test method 926 to the polydiorganosiloxane gum. Typically, the plasticity number is 40-200 or 50-150. Alternatively, the molecular weight of the polydiorganosiloxane gum is at least 600,000, at least 1,000,000, or at least 2,000,000, Daltons. It is contemplated that any and all values or ranges of values between those described above may also be utilized.

The cyclic siloxane and polyorganosiloxane typically react together to form the hydrosilylation reaction product. This reaction typically takes place in the presence of a hydrosilylation catalyst. The hydrosilylation catalyst may be any known in the art. For example, the hydrosilylation catalyst may be a platinum group metal-containing catalyst. By "platinum group" it is meant ruthenium, rhodium, palladium, osmium, iridium and platinum and complexes thereof. Non-limiting examples of platinum group metal-containing catalysts useful herein are the platinum complexes prepared as described in U.S. Pat. Nos. 3,419,593; 5,175,325; 3,989,668; 5,036,117; 3,159,601; 3,220,972; 3,296,291; 3,516,946; 3,814,730; and 3,928,629; each of which is expressly incorporated herein by reference in one or more non-limiting embodiments.

The hydrosilylation catalyst can be platinum metal, platinum metal deposited on a carrier, such as silica gel or powdered charcoal, or a compound or complex of a platinum group metal. Typical hydrosilylation catalysts include chloroplatinic acid, either in hexahydrate form or anhydrous form, and/or a platinum-containing catalyst which is obtained by a method comprising reacting chloroplatinic acid with an aliphatically unsaturated organosilicon compound, such as divinyltetramethyldisiloxane, or alkene-platinum-silyl complexes as described in U.S. Pat. No. 6,605,734, which is expressly incorporated herein by reference in one or more non-limiting embodiments. An example is $(COD)Pt(SiMeCl_2)_2$, where "COD" is 1,5-cyclooctadiene and "Me" is methyl. These alkene-platinum-silyl complexes may be prepared, e.g., by mixing 0.015 mole $(COD)PtCl_2$ with 0.045 mole COD and 0.0612 moles $HMeSiCl_2$.

The amount of hydrosilylation catalyst used typically depends upon the particular catalyst. The hydrosilylation catalyst is typically utilized in an amount sufficient to provide at least 2 ppm, more typically 4-200 ppm of platinum based on total wt % solids (all non-solvent ingredients), based on one million parts of the fluid composition. In various embodiments, the hydrosilylation catalyst is present in an amount sufficient to provide 1-150 weight ppm of platinum on the same basis. The hydrosilylation catalyst may be added as a single species or as a mixture of two or more different species. The hydrosilylation catalyst and amounts thereof can be utilized for various hydrosilylation reactions described herein.

The hydrosilylation reaction between components a) and b) is conducted such the molar ratio of silicon-bonded alkenyl groups of component a) to silicon-bonded hydrogen atoms of component b), prior to reaction to form component A), is from about 0.5/1 to about 2.5/1, alternatively about 0.9/1 to about 2.2/1, alternatively about 1.0/1 to about 1.5/1.

The hydrosilylation reaction between components a) and b) may be conducted neat, or in the presence of a suitable solvent. Typically, the hydrosilylation reaction solvent is selected from one of the carrier fluids described herein.

The stoichiometry of the cross-linking reaction can be controlled so as to produce network polymers where the cross-link density is low enough to produce fluids (where higher cross-link density would generally result in elastomeric solids).

In other related embodiments, functionality of the aforementioned cyclic siloxane and polyorganosiloxane are inversed. Said another way, the cyclic siloxane has at least two silicon-bonded hydrogen atoms per molecule (instead of silicon-bonded alkenyl groups) and the polyorganosiloxane has at least two silicon-bonded alkenyl groups per molecule (instead of silicon-bonded hydrogen atoms). Suitable compounds of this kind are described in US Pub. Nos. 2012/0220549; 2012/0156148; and 2014/0249106; each of which is expressly incorporated herein by reference in one or more non-limiting embodiments.

Third Non-Limiting Example of a Suitable Cross-Linked Siloxane:

In certain embodiments, the cross-linked siloxane is formed by reacting components having various functional groups. Two general embodiments are described below.

In a first general embodiment, the cross-linked siloxane comprises the reaction product of a1) a first siloxane having at least one pendant anhydride group, a2) a second siloxane having at least one pendant anhydride group, and b) a reactant having functional groups reactive with the anhydride groups of the first and second siloxanes.

The reactant is generally selected from the group of an organic polyol, an organic polyamine, a third siloxane (different from the first and second), or combinations thereof. The organic polyol has at least two hydroxyl groups. The organic polyamine has at least two amine groups. The third siloxane can have at least two hydroxyl groups or at least two amine groups. In a first embodiment, the reactant comprises the organic polyol. Other embodiments can use one or more of the other reactants in addition or alternate to the organic polyol.

Typically, the cross-linked siloxane is of the following general formula (I):

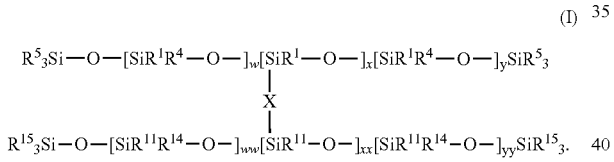

Each X is of the following general formula (i):

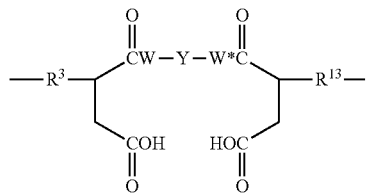

Each of W and W* is independently an oxygen atom (O) or N—R, with R independently being hydrogen atom (H) or $R^1$. Each Y is a divalent group. In various embodiments, each of W and W* is independently an O, and Y is an organic divalent group. Each of $R^1$, $R^{11}$, $R^4$, $R^{14}$, $R^5$, and $R^{15}$ is an independently selected substituted or unsubstituted hydrocarbyl group. Each of $R^3$ and $R^{13}$ is an independently selected divalent group. Each of "w" and "ww" is independently 0-1,000. Each of "x" and "xx" is independently 1-100. Each of "y" and "yy" is independently 0-1,000. Typically, "w" and "y" are not simultaneously 0, and "ww" and "yy" are not simultaneously 0. As shown in formula (i), the cross-linked composition generally has at least two carboxyl groups. Such carboxyl groups can be left free or used for further reaction, e.g. cross-linking or capping.

In a second general embodiment, the cross-linked siloxane comprises the reaction product of a1) a first reactant having at least one hydroxyl or amine group, a2) a second reactant having at least one hydroxyl or amine group, and b) a siloxane having at least two terminal anhydride groups reactive with the groups of the first and second reactants.

The first reactant is selected from the group of a first siloxane different from the siloxane and having at least one hydroxyl group, a first siloxane different from the siloxane and having at least one amine group, a first organic alcohol having at least one hydroxyl group, a first organic amine having at least one amine group, or combinations thereof.

The second reactant is selected from the group of a second siloxane different from the siloxane and having at least one hydroxyl group, a second siloxane different from the siloxane and having at least one amine group, a second organic alcohol having at least one hydroxyl group, a second organic amine having at least one amine group, or combinations thereof.

In a first embodiment, the first reactant comprises the first siloxane having at least one hydroxyl group and the second reactant comprises the second siloxane having at least one hydroxyl group, i.e., the reactants are hydroxyl functional siloxanes. In a second embodiment, the first reactant comprises the first siloxane having at least one amine group and the second reactant comprises the second siloxane having at least one amine group, i.e., the reactants are amine functional siloxanes.

In a third embodiment, the first reactant comprises the first organic alcohol and the second reactant comprises the second organic alcohol, i.e., the reactants are organic alcohols. In a fourth embodiment, the first reactant comprises the first organic amine and the second reactant comprises the second organic amine, i.e., the reactants are organic amines.

In the first and second embodiments, the cross-linked siloxane is typically of the following general formula (I):

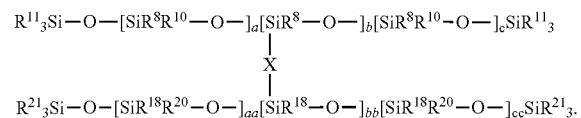

Each X is of the following general formula (i):

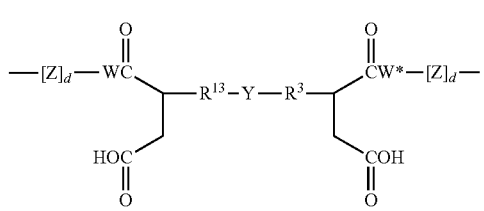

Each Y is of the following formula (ii):

Each of W and W* is independently an O or N—R, with R independently being an H or $R^1$. Each of Z, $R^3$, and $R^{13}$ is an independently selected divalent group. Each of $R^1$, $R^2$, $R^4$, $R^5$, $R^8$, $R^{18}$, $R^{10}$, $R^{20}$, $R^{11}$, and $R^{21}$ is an independently selected substituted or unsubstituted hydrocarbyl group. Each of "a" and "aa" is independently 0-1,000. Each of "b" and "bb" is independently 1-200. Each of "c" and "cc" is independently 0-1,000. Each "d" is independently 0 or 1. Further, "w" is 0-1,000, "x" is 0-100, and "y" is 0-1,000.

In the third and fourth embodiments, the cross-linked siloxane is typically of the following general formula (II):

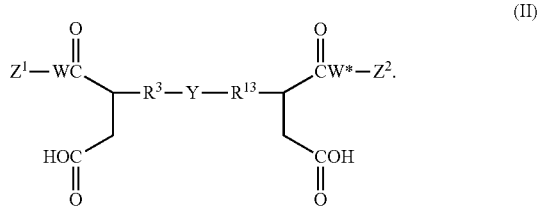

(II)

Each Y is of the following formula (ii):

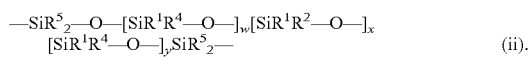

(ii).

Each of $Z^1$ and $Z^2$ is independently attributable to the organic alcohol or the organic amine. Each of W, W*, $R^3$, $R^{13}$, $R^1$, $R^2$, $R^4$, $R^5$, "w", "x", and "y" is as above.

The aforementioned cross-linked siloxanes and/or other components that may be used to form the composition and/or personal care composition of this disclosure are described in PCT/US2014/062873 and PCT/US2014/062877, each of which is expressly incorporated herein by reference in one or more non-limiting embodiments. Such components include the cross-linked compositions, siloxanes, e.g. allyl succinic anhydride (ASA) siloxanes, and examples described therein.

Fourth Non-Limiting Example of a Suitable Cross-Linked Siloxane:

In certain embodiments, the cross-linked siloxane is formed by reacting components having substantially linear structures. The cross-linked siloxane is the hydrosilylation reaction product of first and second linear organopolysiloxanes. In various embodiments, the terminology "linear" describes that the first linear organopolysiloxane, second linear organopolysiloxane, and/or cross-linked siloxane itself include <1, <0.5, <0.1, or <0.01, weight percent of T and Q units, i.e., siloxy units having the formulae (substituent-$SiO_{3/2}$) and ($SiO_{4/2}$), respectively. In other embodiments, the terminology "linear" describes that the first linear organopolysiloxane, second linear organopolysiloxane, and/or cross-linked siloxane itself, is not branched or is not highly branched. In still other embodiments, the backbone of the first linear organopolysiloxane, second linear organopolysiloxane, and/or cross-linked siloxane is described as being linear, e.g. not branched or highly branched. For example, while the backbone of the first linear organopolysiloxane, second linear organopolysiloxane, and/or cross-linked siloxane itself is typically linear, the backbone may have one or more cyclic, aromatic, or otherwise non-linear substituents attached thereto. In such a scenario, the backbone of, and the first linear organopolysiloxane, second linear organopolysiloxane, and/or cross-linked siloxane themselves, would still be considered "linear" as used herein. Moreover, the terms "branched" and "highly branched" used above are used as understood by those of skill in the art.

One or more than one first linear organopolysiloxane can be reacted with one or more than one second linear organopolysiloxane. Similarly, in various embodiments, one first linear organopolysiloxane is reacted with two (or more) second linear organopolysiloxanes. Alternatively, two (or more) first linear organopolysiloxanes may be reacted with one second linear organopolysiloxane. Thus, in various embodiments, wherever "first linear organopolysiloxane" is used herein, two or more first linear organopolysiloxanes can be used. In other embodiments, wherever "second linear organopolysiloxane" is used herein, two or more second linear organopolysiloxanes can be used.

The cross-linked siloxane includes alkenyl or Si—H functionality (e.g. as the result of the reaction of the first and second linear organopolysiloxanes). In various embodiments, the alkenyl or Si—H functionality may be observed on a parts per million (ppm) or parts per billion (ppb) level, based on a total weight of the cross-linked siloxane. In other embodiments, the alkenyl or Si—H functionality is understood based on a molar ratio of alkenyl to Si—H functionality of the reactants (e.g. the first and second linear organopolysiloxanes) used to form the cross-linked siloxane. For example, the ratio of alkenyl to Si—H units used to form the cross-linked siloxane (e.g. from the first and second linear organopolysiloxanes) may be <1 or >1. In various embodiments, this ratio is from 0.01 to <1, 0.1 to <1, 0.2 to 0.9, 0.3 to 0.8, 0.4 to 0.7, or 0.5 to 0.6. In other embodiments, this ratio is >1, from >1 to 100, >1 to 50, >1 to 25, >1 to 15, >1 to 10, or >1 to 5. Typically, the ratio of alkenyl to Si—H units is not exactly 1. However, a ratio of 1 is contemplated in one embodiment. It is contemplated that any and all values or ranges of values between those described above may also be utilized.

In various embodiments, the cross-linked siloxane is present in an amount of from 3-30, 5-25, 5-20, 5-15, 5-10, 5-9, 6-9, or 7-8, parts by weight per 100 parts by weight of the composition. This amount, in parts by weight, may also be described as a "percent solids" or "percent active(s)." It is contemplated that any and all values or ranges of values between those described above may also be utilized.

The first linear organopolysiloxane includes ($R^1R^2R^3SiO_{1/2}$) and ($R^4R^5SiO_{2/2}$) units, also known as M and D units, respectively. Each of $R^1$-$R^5$ is independently a hydrocarbon group so long as at least one of $R^1$-$R^5$ is an alkenyl group. The hydrocarbon group may be an alkyl group having 1-20, 2-15, 3-10, 5-10, etc., carbon atoms, such as methyl, ethyl, propyl, butyl, pentyl and hexyl; cycloalkyl groups, such as cyclohexyl and cycloheptyl; aryl groups having 6-12 carbon atoms, such as phenyl, tolyl and xylyl; or aralkyl groups having 7-20 carbon atoms, such as benzyl and phenylethyl. The hydrocarbon group may also be an alkenyl group having 2-20 carbon atoms, such as vinyl, allyl, butenyl, pentenyl, hexenyl and decenyl, typically vinyl or hexenyl, groups. Alternatively, the hydrocarbon group may include one or more halogen atoms. It is contemplated that any and all values or ranges of values between those described above may also be utilized.

The first linear organopolysiloxane can be a homopolymer, a copolymer or a terpolymer. Non-limiting examples include copolymers including dimethylsiloxy units and phenylmethylsiloxy units, copolymers including dimethylsiloxy units and 3,3,3-trifluoropropylmethylsiloxy units, copolymers of dimethylsiloxy units and diphenylsiloxy units and interpolymers of dimethylsiloxy units, diphenylsiloxy units and phenylmethylsiloxy units, among others. The first linear organopolysiloxane typically has a linear backbone but may include non-linear substituents attached to the backbone.

In various embodiments, the first linear organopolysiloxane includes <1, <0.5, <0.1, or <0.01, weight percent of T and/or Q units. Alternatively, the first linear organopolysiloxane is free of T and/or Q units. In other embodiments, the first linear organopolysiloxane has a degree of polymerization (DP) of from 100-15,000, 500-15,000, 2,000-15,000, 5,000-15,000, 7,500-15,000, 8,000-15,000, 10,000-12,000, or about 10,000. It is contemplated that any and all values or ranges of values between those described above may also be utilized.

In one embodiment, the first linear organopolysiloxane is a polydiorganosiloxane gum. As used herein, polydiorganosiloxane gums include predominately D units. For example, the polydiorganosiloxane gum may itself have viscosity of at least 1,000,000, or at least 2,000,000, mm$^2$/s at 25° C. Alternatively, the molecular weight may be sufficient to impart a Williams plasticity number of at least 40 as determined by the American Society for Testing and Materials (ASTM) test method 926 to the polydiorganosiloxane gum. Typically, the plasticity number is 40-200 or 50-150. Alternatively, the molecular weight of the polydiorganosiloxane gum is at least 600,000, at least 1,000,000, or at least 2,000,000, Daltons. It is contemplated that any and all values or ranges of values between those described above may also be utilized.

Specific non-limiting illustrations of polydiorganosiloxane gums include: trimethylsiloxy-endblocked dimethylsiloxane, trimethylsiloxy-endblocked dimethylsiloxane-methylvinylsiloxane copolymers; trimethylsiloxy-endblocked methylphenylsiloxane-dimethylsiloxane-methylvinylsiloxane copolymers; trimethylsiloxy-endblocked 3,3,3-trifluoropropylmethyl siloxane copolymers; trimethylsiloxy-endblocked 3,3,3-trifluoropropylmethyl-methylvinylsiloxane copolymers; dimethylvinylsiloxy-endblocked dimethylpolysiloxanes; dimethylvinylsiloxy-endblocked dimethylsiloxane-methylvinylsiloxane copolymers; dimethylvinylsiloxy-endblocked methylphenylpolysiloxanes; dimethylvinylsiloxy-endblocked methylphenylsiloxane-dimethylsiloxane-methylvinylsiloxane copolymers; and similar copolymers wherein at least one end group is dimethylhydroxysiloxy. The polydiorganosiloxane gum may also be or include a combination of two or more organopolysiloxanes. Methods for preparing polydiorganosiloxane gums are well known and many are commercially available.

In other embodiments, the first linear organopolysiloxane is a fluid. For example, the fluid may have a viscosity of from 1,000-100,000, 25,000-100,000, 25,000-75,000, 50,000-75,000, 50,000-65,000, or 55,000-60,000, mm$^2$/s at 25° C. The fluid may alternatively have a molecular weight of from 7,500-700,000, 50,000-500,000, or 100,000-250,000, Daltons. In other embodiments, DOW CORNING® ("DC") fluids; 4-2764, 2-7891, 2-7754, 2-7891, and 2-7463, SFD-117, SFD-119, SFD-120, SFD-128, SFD-129, 5-8709, LV, 2-7038, 2-7892, 2-7287, 2-7463, dihexenyl terminal 7692, 7697, along with 2-7063 and 2-7748, and combinations thereof, can be used. It is contemplated that any and all values or ranges of values between those described above may also be utilized.

The second linear organopolysiloxane includes (R$^6$R$^7$R$^8$SiO$_{1/2}$) and (R$^9$R$^{10}$SiO$_{2/2}$) units. Each of R$^6$-R$^{10}$ is independently a hydrocarbon group so long as at least one of R$^6$—R$^{10}$ is a hydrogen atom. The hydrocarbon group may be any described above.

In various embodiments, the second linear organopolysiloxane includes <1, <0.5, <0.1, or <0.01, weight percent of T and/or Q units. Alternatively, the second linear organopolysiloxane may be entirely free of T and/or Q units. In other embodiments, the second linear organopolysiloxane has a degree of polymerization of from 4-1,000, 8-500, 25-400, 50-300, 75-200, or 75-100, alternatively 100-500, 100-400, 100-300, 100-200, 75-150, 75-125, or about 100. It is contemplated that any and all values or ranges of values between those described above may also be utilized.

The second linear organopolysiloxane may be a gum or a fluid, as described above. Non-limiting examples of the second linear organopolysiloxane are DC fluids; 5-0210, 6-3570, 1-8114, 1-3502, OFX-5057, OFX-5084, OFX-5625, MHX-1107, and combinations thereof. These are all commercially available products that represent SiH pendant, SiH terminal, or SiH homopolymers.

The first and second linear organopolysiloxanes typically react together to form the cross-linked siloxane. This reaction typically takes place in the presence of a hydrosilylation catalyst. The hydrosilylation catalyst may be any known in the art. Suitable catalysts and amounts thereof are as described above, e.g. platinum group metal-containing catalysts.

Other cross-linked siloxanes and/or components that may be used to form the compositions and/or personal care compositions of this disclosure are described in PCT/US15/024905 and PCT/US15/024886, each of which is expressly incorporated herein by reference in one or more non-limiting embodiments.

Non-Limiting Examples of Suitable Silicone Polyether Copolymers:

In certain embodiments, the copolymer of the first component comprises a silicone polyether copolymer. Various types of silicone polyether copolymers can be used. Reaction schemes of different types can be utilized to obtain silicone polyether copolymers, and many are commercially available (e.g. from Dow Corning Corporation).

Certain silicone polyether copolymers can also be referred to as polyoxyalkylene siloxane copolymers or polyoxyalkylene-substituted silicones (e.g. rake or (AB)$_n$ types). The polyoxyalkylene group of the copolymer may comprise oxyethylene units (C$_2$H$_4$O), oxypropylene units (C$_3$H$_6$O), oxybutylene units (C$_4$H$_8$O), or mixtures thereof. Examples of suitable silicone polyether copolymer for forming the composition follow below.

First Non-Limiting Example of a Suitable Silicone Polyether Copolymer:

In certain embodiments, the silicone polyether copolymer is an (AB)$_n$ silicone polyether copolymer. In a specific embodiment, the (AB)$_n$ silicone polyether copolymer is represented by the general formula: —[—(R$^2$SiO)$_a$R$_2$SiYO(C$_n$H$_{2n}$O)$_b$Y—]$_c$— where each R is an independently selected hydrogen or monovalent group; each Y is an independently selected divalent group; "a" is ≥4; "b" is ≥4; "c" is ≥2; and "n" is 2-4.

Examples of R independently include hydrogen; a monovalent hydrocarbon group, such as methyl, ethyl, propyl, butyl, pentyl, hexyl, heptyl, octyl, nonyl, decyl, dodecyl, octadecyl, eicosyl, phenyl, naphthyl, benzyl, phenylethyl, tolyl, xylyl, cyclohexyl, polycaprolactone, trifluoropropyl, and chloropropyl, groups; organic reactive groups, such as epoxy, amino, hydroxyl, carboxyl, acyl, mercapto, methacrylo, isocyanate, ureido, vinyl, amide, imide, imino, aldehyde, nitro, nitrile, oxime, azo, and hydrazone, groups; an inorganic reactive group, such as methoxy, ethoxy, trimethoxysilyl ethyl, triethoxysilylethyl, and methyldimethoxysilyl ethyl; and hydrophilic groups, such as polyether and glucose groups. In specific embodiments, each R is methyl.

Y is bonded between the adjacent silicon and oxygen atoms. Examples of Y independently include the following groups: —R'—, —R'CO—, —R'NHCO—, —R'N-

HCONHR"NHCO— or —R'OOCNHR"NHCO— where R' is a divalent alkylene group, such as ethylene, propylene, butylene, or the like; and R" is a divalent alkylene group, such as R' or a divalent arylene group, such as —$C_6H_4$—, —$C_6H_4C_6H_4$—, —$C_6H_4CH_2C_6H_4$—, —$C_6H_4CH(CH_3)$ $C_6H_4$—, or like.

Specific examples of groups for Y include the following: —$CH_2CH_2$—, —$CH_2CH_2CH_2$—, —$CH_2CH(CH_3)CH_2$—, —$CH_2CH_2CH_2CH_2$—, —$(CH_2)_2CO$—, —$(CH_2)_3NHCO$—, —$(CH_2)_3NHCONHC_6H_4NHCO$—, and —$(CH_2)_3$ $OOCNHC_6H_4NHCO$—.

Second Non-Limiting Example of a Suitable Silicone Polyether Copolymer:

In certain embodiments, the silicone polyether copolymer is a polyethylene glycol polypropylene glycol (PEG/PPG) polydimethylsiloxane (PDMS) copolymer. Typically, the PEG and PPG is grafted onto the PDMS backbone (e.g. rake) by methods understood in the art.

The silicone polyether copolymer can have various amounts of PEG and PPG, and each of the PEG and PPG can be individually present in the same or differing amounts. In certain embodiments, each of the PEG and PPG is individually present in an amount of from about 1-50, 1-40, 5-30, 5-25, 10-20, 12-18, 14-18, 16-18, or 18, moieties per PDMS molecule/backbone.

The silicone polyether copolymer can be of various degrees of polymerization. Typically, the silicone polyether copolymer has a DP of from about 10-1,000, 50-1,000, 100-1,000, 100-750, 100-500, 200-500, 300-500, or 400. A specific example of a suitable silicone polyether copolymer is DOW CORNING® 5225C Formulation Aid: (INCI Name: Cyclopentasiloxane (and) PEG/PPG-18/18 Dimethicone)

Some of the aforementioned silicone polyether copolymers, other silicone polyether copolymers, and/or other components that may be used to form the compositions and/or personal care compositions of this disclosure are described in U.S. Pat. Nos. 4,122,029; 4,218,250; 4,311,695; 5,302,382; 5,811,487; 5,891,954; 6,133,370; 6,987,157; 7,887,834; 7,790,827; 8,008,407; 8,013,097; and 8,734,767; US Pub Nos. 2007/0243241; 2007/0166263; 2010/0184935; and 2011/0189248; and WO2005/103117; each of which is expressly incorporated herein by reference in one or more non-limiting embodiments.

Non-Limiting Examples of Suitable Saccharide Siloxane Copolymers:

In certain embodiments, the copolymer of the first component comprises a saccharide siloxane copolymer. Such copolymers may also be referred to as sugar siloxanes. Various types of saccharide siloxane copolymers can be used. Reaction schemes of different types can be utilized to obtain saccharide siloxane copolymers. Examples of suitable saccharide siloxane copolymer for forming the composition follow below.

In a specific embodiment, the saccharide siloxane copolymer is represented by the general formula: $R^2_a R^1_{(3-a)} SiO [(SiR^2R^1O)_m(SiR^1_2O)n]_y SiR^1_{(3-a)} R^2_a$ where each $R^1$ is an independently selected hydrogen, alkyl group, organic group, or $R^3$-Q group, with Q comprising an epoxy, cycloalkylepoxy, primary or secondary amino, ethylenediamine, carboxy, halogen, vinyl, allyl, anhydride, or mercapto functionality; each of "m" and "n" is independently 0-10,000; each "a" is independently 0-3; "y" is an integer such that the saccharide siloxane copolymer has a molecular weight <1 million; each $R^2$ independently has the formula: $Z(G^1)_b(G^2)_c$ where $G^1$ is a saccharide component having 5-12 carbon atoms, with a proviso that there is at least one $R^2$ per molecule; each of "b" and "c" is independently 0-10, with a proviso that (b+c) is 1-10; $G^2$ is a saccharide component having 5-12 carbon atoms additionally substituted with organic or organosilicon radicals; each Z is independently selected from the group of; —$R^3N(R^8)C(O)R^4$—, —$R^3CH(OH)CH_2N(R^8)R^4$—, and —$R^3CH(N(R^4)(R^8))$ $CH_2OH$; each of $R^3$ and $R^4$ is independently of the formula: $(R^5)_r(R^6)_s(R^7)_t$ where at least one of "r", "s" and "t" is 1; each of $R^5$ and $R^7$ is independently an alkylene group having 1-12 carbon atoms or a group of formula: $(R^9O)_p$ where each $R^9$ is independently a divalent organic group and "p" is 1-50; each $R^6$ is independently —$N(R^8)$— where $R^8$ is selected from $R^3$, a group of formula Z—X, an unsaturated hydrocarbon group, or a reaction product of —N(H)— with an epoxy functional group, a cycloalkylepoxy functional group, a glycidyl ether functional group, an acid anhydride functional group, or a lactone; and each X is independently a divalent carboxylic acid, phosphate, sulfate, sulfonate or quaternary ammonium radical; with a proviso that at least one of $R^3$ and $R^4$ is present in Z.

The aforementioned saccharide siloxane copolymer, other saccharide siloxane copolymers, and/or other components that may be used to form the compositions and/or personal care compositions of this disclosure are described in U.S. Pat. Nos. 7,834,087; 8,853,372; 8,877,216; and 8,907,026; and US Pub Nos. 2013/0149259; 2013/0149260; 2013/0149261; and 2014/0357884; each of which is expressly incorporated herein by reference in one or more non-limiting embodiments.

Second Component:

The second component comprises an organopolysiloxane resin, an acrylate copolymer, or a combination thereof. Various types of organopolysiloxane resins can be utilized to form the composition. Likewise, various types of acrylate copolymers can be utilized to form the composition; however, suitable acrylate copolymers generally include silicon-containing moieties, more typically siloxy-containing moieties.

The second component can be utilized in the composition in various amounts. Typically, the second component is present in an amount of from about 0.1-99.9, 1-99, 5-95, 10-90, 20-80, 30-70, 40-60, 45-55, or 50, wt % based on 100 parts by weight of the composition.

The first and second components can be present in the composition in various weight ratios relative to one another. In various embodiments, first and second components are present in a weight ratio of from about 10:1 to about 1:10, 9:1 to 1:9; 8:1 to 1:8, 7:1 to 1:7, 6:1 to 1:6, 5:1 to 1:5, 4:1 to 1:4, 3:1 to 1:3, 2:1 to 1:2, or 1:1. It is contemplated that any and all values or ranges of values between those described above may also be utilized.

Non-Limiting Examples of Suitable Organopolysiloxane Resins:

In various embodiments, the composition includes an MQ resin. MQ resins are macromolecular polymers consisting essentially of $R_3SiO_{1/2}$ and $SiO_{4/2}$ units (the M and Q units, respectively) where R is a functional or nonfunctional organic group. Those skilled in the art appreciate that MQ resins may also include a limited number of D and T units. Specifically, the MQ resin may contain D and T units, provided that 280, or 290, mole % of the total siloxane units are M and Q units. Alternatively, the MQ resin may be free of D and/or T units.

The MQ resin can be an organosiloxane resin comprising siloxy units of the formula: $(R^1_3SiO_{1/2})_m(SiO_{4/2})_n$ where each $R^1$ is an independently selected substituted or unsubstituted hydrocarbyl group, "m" is ≥4, and "n" is ≥1. The ratio of m/n can vary, but is typically about 1.5-1, 0.6-1, or 0.9-1.

Suitable hydrocarbyl groups are described above. In certain embodiments, each $R^1$ is an independently selected alkyl group having from 1-8 carbon atoms, an aryl group, a carbinol group, or an amino group. The alkyl groups are generally illustrated by methyl, ethyl, propyl, butyl, pentyl, hexyl, and octyl, with the alkyl group typically being methyl. The aryl groups are generally illustrated by phenyl, naphthyl, benzyl, tolyl, xylyl, xenyl, methylphenyl, 2-phenylethyl, 2-phenyl-2-methylethyl, chlorophenyl, bromophenyl and fluorophenyl, with the aryl group typically being phenyl.

A "carbinol group" is generally any group containing at least one carbon-bonded hydroxyl (COH) radical. Thus, the carbinol group may contain more than one COH radical, such as e.g.:

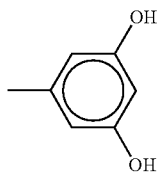

If free of aryl groups, the carbinol group typically has ≥3 carbon atoms. Such carbinol groups are generally illustrated by the formula: $R^4OH$ where $R^4$ is a divalent hydrocarbon or hydrocarbonoxy radical having ≥3 carbon atoms. $R^4$ is illustrated by alkylene radicals, such as by the formula: —$(CH_2)_x$— where x is 3-10; or by the formula: —$CH_2CH(CH_3)$—, —$CH_2CH(CH_3)CH_2$—, —$CH_2CH_2CH(CH_2CH_3)CH_2CH_2CH_2$—, or —$OCH(CH_3)(CH_2)_x$—, where x is 1-10.

An aryl-containing carbinol group typically has ≥6 carbon atoms. Such carbinol groups are generally illustrated by the formula: $R^5OH$ where $R^5$ is an arylene radical having from 6-14 carbon atoms. $R^5$ is illustrated by arylene radicals, such as by the formula: —$(CH_2)_xC_6H_4$— where x is 0-10; —$CH_2CH(CH_3)(CH_2)_xC_6H_4$— where x is 0-10; or —$(CH_2)_x C_6H_4(CH_2)_x$— where x is 1-10.

The amino group is illustrated by the formula: —$R^6NH_2$ or —$R^6NHR^7NH_2$ where each of $R^6$ and $R^7$ is independently a divalent hydrocarbon radical having ≥2 carbon atoms, typically each of $R^6$ and $R^7$ is independently an alkylene radical having from 2-20 carbon atoms. Each of $R^6$ and $R^7$ are independently illustrated by ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene. Typical amino groups include: —$CH_2CH_2CH_2NH_2$, —$CH_2(CH_3)CHCH_2(H)NCH_3$, —$CH_2CH_2NHCH_2CH_2NH_2$, —$CH_2CH_2NH_2$, —$CH_2CH_2NHCH_3$, —$CH_2CH_2CH_2CH_2NH_2$, —$(CH_2CH_2NH)_3H$, and —$CH_2CH_2NHCH_2CH_2NHC_4H_9$.

The MQ resin may also contain hydroxy groups. In various embodiments, the MQ resin has a total wt % hydroxy content of from 0-15, 1-12, 2-10, or 2-5, wt %. The MQ resin can also be further "capped" where residual hydroxy groups are reacted with additional M units.

MQ resins and methods for their preparation are known in the art. For example, U.S. Pat. No. 2,814,601 discloses that MQ resins can be prepared by converting a water-soluble silicate into a silicic acid monomer or silicic acid oligomer using an acid. When adequate polymerization has been achieved, the resin is end-capped with trimethylchlorosilane to yield the MQ resin. Another method for preparing MQ resins is described in U.S. Pat. No. 2,857,356, which discloses a method for the preparation of an MQ resin by the co-hydrolysis of a mixture of an alkyl silicate and a hydrolyzable trialkylsilane organopolysiloxane with water.

Other suitable MQ resins and their methods of preparation are disclosed by U.S. Pat. Nos. 6,075,087, 7,452,849, 7,803,358, 8,012,544, and 8,017,712; and in WO2010065712 and WO2013117490. The aforementioned patents and publications are expressly incorporated herein by reference in one or more non-limiting embodiments. Suitable MQ resins are commercially available, such as DOW CORNING® MQ-1600 solid resin, MQ-1601 solid resin, MQ-1640 flake resin, 217 flake, and 5-7104.

If utilized, the MQ resin can be included in the composition in various amounts. In certain embodiments, the MQ resin is present in an amount of from about 0-99, 10-90, 30-90, or 40-80, parts by weight based on 100 parts by weight of the composition. Two or more different MQ resins may be utilized.

Non-Limiting Examples of Suitable Acrylate Copolymers:

In various embodiments, the composition includes an acrylate copolymer. Suitable acrylate copolymers are commercially available, such as DOW CORNING® FA 4001 CM silicone acrylate and DOW CORNING® FA 4002 ID silicone acrylate.

The acrylate copolymer can be formed by the reaction of a radically polymerizable organic monomer, which can be exemplified by: the esters of unsaturated carboxylic acids, such as methyl acrylate, ethyl acrylate, propyl acrylate, n-butyl acrylate, isobutyl acrylate, amyl acrylate, hexyl acrylate, 2-ethylhexyl acrylate, cyclohexyl acrylate, n-octyl acrylate, glycidyl acrylate, 2-hydroxyethyl acrylate, 2-hydroxypropyl acrylate, 2,2,3,3-tetrafluoropropyl acrylate, octafluoropentyl acrylate, methyl methacrylate, ethyl methacrylate, n-butyl methacrylate, isobutyl methacrylate, 2-ethylhexyl methacrylate, lauryl methacrylate, tridecyl methacrylate, benzyl methacrylate, cyclohexyl methacrylate, tetrahydrofurfuryl methacrylate, 2-hydroxyethyl methacrylate, 2-hydroxypropyl methacrylate, glycidyl methacrylate, 2-methoxyethyl methacrylate, 2-ethoxyethyl methacrylate, and octafluoropentyl methacrylate; unsaturated aliphatic carboxylic acids, such as methacrylic acid and acrylic acid; the amides of unsaturated aliphatic carboxylic acids, such as acrylamide, methacrylamide, and N-methylolacrylamide; unsaturated aliphatic nitriles, such as acrylonitrile and methacrylonitrile; unsaturated aliphatic compounds, such as vinyl acetate, vinyl propionate, and vinyl versatate; unsaturated carboxylic acid anhydrides, such as maleic anhydride and 4-methacryloxyethyltrimellitic anhydride (4-META); vinyl halides, such as vinyl chloride and vinyl fluoride; aromatic vinyl compounds, such as styrene, methylstyrene, vinyltoluene and vinylpyridine; and aliphatic dienes, such as butadiene and isoprene.

The copolymer may be a carbosiloxane dendrimer, such as those described and prepared in U.S. Pat. No. 6,306,992, which is expressly incorporated herein by reference in one or more non-limiting embodiments. Examples of suitable carbosiloxane dendrimers include those represented by the general formula:

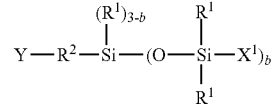

where each $R^1$ is independently a 1-10 carbon alkyl or aryl group; $R^2$ is a divalent organic group excluding 1-10 carbon alkylene groups; "b" is 1-3; and $X^1$ is a silylalkyl group represented b the following general formula (when "i"=1):

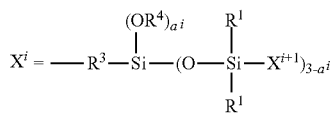

where $R^1$ is defined as above; $R^3$ is a 2-10 carbon alkylene group; $R^4$ is a 1-10 carbon alkyl group; $X^{i+1}$ is selected from hydrogen, a 1-10 carbon alkyl group, an aryl group, and the $X^1$ silylalkyl group; "i" indicates a generation number of the $X^1$ silylalkyl group above and is 1-10; $a^i$ is 0-3; and Y is a radically-polymerizable group. The radically-polymerizable group is typically selected from: a 2-10 carbon alkenyl group; groups with the following general formula:

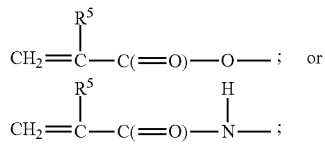

or groups with the following formula:

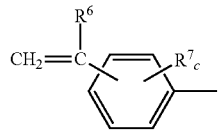

where each of $R^5$ and $R^6$ is independently hydrogen or Me; $R^7$ is a 1-10 carbon alkyl group; and "c" is 0-4.

The copolymer may be a branched siloxane-silalkylene copolymer, such as those described and prepared in U.S. Pat. No. 6,420,504, which is expressly incorporated herein by reference in one or more non-limiting embodiments. Examples of suitable branched siloxane-silalkylene copolymers include those represented by the general formula:

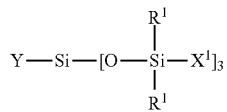

where $R^1$ is defined as above; and $X^1$ is a silylalkyl group represented by the following general formula (when "i"=1):

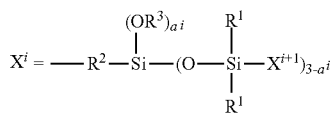

where $R^1$ is defined as above; $R^2$ is a 2-10 carbon alkylene group; $R^3$ is a 1-10 carbon alkyl group; and $X^{i+1}$ is selected from hydrogen, a 1-10 carbon alkyl group, an aryl group, and the $X^1$ silylalkyl group above; "i" indicates a generation number of the $X^1$ silylalkyl group above and is 1-10; and $a^i$ is from 0-3. Y is a radical-polymerizable group. The radically-polymerizable group is typically selected from: a 2-10 carbon alkenyl group; a (meth)-acryl group-containing organic group represented by the following general formula:

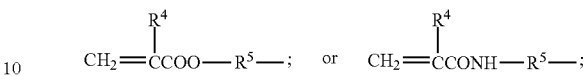

a styryl group-containing organic group represented by the following general formula:

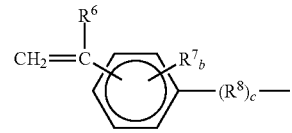

where each of $R^4$ and $R^6$ is independently hydrogen or Me; each of $R^5$ and $R^8$ is independently a 1-10 carbon alkylene group; $R^7$ is a 1-10 carbon alkyl group; "b" is 0-4; and "c" is 0 or 1.

If utilized, the copolymer can be included in the composition in various amounts. In certain embodiments, the copolymer in present in an amount of from about 0-99, 10-90, 30-90, or 40-80, parts by weight based on 100 parts by weight of the composition. Two or more different copolymers may be utilized.

Optional Carrier Fluid:

In certain embodiments, the composition further comprises a carrier fluid. Various types of carrier fluids can be utilized to form the composition. The carrier fluid is typically selected from the group of silicones, organic solvents, organic oils, and combinations thereof. Various reaction products described herein can be formed in the presence of the carrier fluid and/or the carrier fluid can be used as a diluent for the composition. If used for both purposes, the same or a different carrier fluid can be used for each.

Suitable carrier fluids include silicones, both linear and cyclic, organic oils, organic solvents and combinations of these. Specific examples of solvents may be found in U.S. Pat. No. 6,200,581, which is hereby expressly incorporated by reference in various non-limiting embodiments relative to these solvents. In one embodiment, the carrier fluid is a polydimethylsiloxane. In various other embodiments, the carrier fluid is a low viscosity silicone or a volatile methyl siloxane or a volatile ethyl siloxane or a volatile methyl ethyl siloxane having a viscosity from 1-1,000 mm²/s measured at 25° C., such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadecamethylheptasiloxane, heptamethyl-3-{(trimethylsilyl)oxy)}trisiloxane, hexamethyl-3,3,bis{(trimethylsilyl)oxy}trisiloxane, and pentamethyl{(trimethylsilyl)oxy}cyclotrisiloxane, as well as polydimethylsiloxanes, polyethylsiloxanes, polymethylethylsiloxanes, polymethylphenylsiloxanes, polydiphenylsiloxanes, and combinations thereof. Examples of suitable carrier fluids include DOW CORNING® 200 Fluids, e.g. 2 cSt and 5 cSt; and DOW CORNING® FZ-3196.

The organic solvent may include, but is not limited to, aromatic hydrocarbons, aliphatic hydrocarbons, alcohols, aldehydes, ketones, amines, esters, ethers, glycols, glycol ethers, alkyl halides, aromatic halides, and combinations thereof. Hydrocarbons including isododecane, isohexadecane, Isopar L ($C_{11}$-$C_{13}$), Isopar H ($C_{11}$-$C_{12}$), hydrogenated polydecene, and combinations thereof, may also be used. Ethers and esters including isodecyl neopentanoate, neopentylglycol heptanoate, glycol distearate, dicaprylyl carbonate, diethylhexyl carbonate, propylene glycol n-butyl ether (PnB), ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, octyl palmitate, and combinations thereof, may also be used. Organic fats, oils, fatty acids, fatty alcohols, and combinations thereof, may also be used.

The carrier fluid typically has a viscosity of from 1-1,000, 2-50, or 5-50, alternatively 2-20, 2-15, 2-10, or 2-5, mm$^2$/s measured at 25° C. It is contemplated that any and all values or ranges of values between those described above may also be utilized.

If utilized, the carrier fluid is typically present in the composition in an amount of from about 50-99.9, 60-99.9, 70-99.9, or 80-99.99, alternatively about 70-97, 75-95, 80-95, 85-95, 90-95, 93-95, 91-95, 92-94, or 92-93, wt % based on 100 parts by weight of the composition. It is contemplated that any and all values or ranges of values between those described above may also be utilized.

The combination of the carrier fluid and the first and second components provide the composition with a viscosity, measured in Pascal seconds (Pa·s) and collected relative to the shear rate in sec$^{-1}$, of from about 0.1-75, 0.3-15, 0.5-5, or 1-3, Pa·s. These viscosity values are typically measured using a controlled stress rheometer, such as the TA Instruments AR 1000-N. In various embodiments, the term "fluid", as used herein, describes a liquid whose component particles can move past one another, that is flow, when a force is applied, such as gravity. In this embodiment, "fluids" do not encompass "gels", which do not flow. In other embodiments, the composition has a viscosity of ≥100, ≥200, or ≥300, mPa·s at 23° C., each with a maximum of one of the values described above. It is contemplated that any and all values or ranges of values between those described above may also be utilized.

Optional Compound(s):

The composition may also include one or more optional compounds. Non-limiting examples of such optional compounds include a compound or mixture of compounds having a mono terminal aliphatic unsaturated hydrocarbon group. For example, this optional compound may be or include a hydrocarbon containing 6-30 carbon atoms having one terminal unsaturated aliphatic hydrocarbon group, and/or a polyoxyalkylene having one terminal unsaturated aliphatic group.

Use of this optional compound can alter the resulting chemical and physical properties of the composition. For example, the optional compound may add hydrocarbon groups to the first and/or second components, thus adding more hydrophobic character to the composition. Conversely, if the optional compound is, e.g. a polyoxyalkylene having a majority of ethylene oxide units, use may result in increased hydrophilicity of the composition.

The unsaturated aliphatic hydrocarbon group(s) in the optional compound can be an alkenyl or alkynyl group. Representative, non-limiting examples of alkenyl groups are shown by the following structures; $H_2C=CH-$, $H_2C=CHCH_2-$, $H_2C=C(CH_3)CH_2-$, $H_2C=CHCH_2CH_2-$, $H_2C=CHCH_2CH_2CH_2-$, and $H_2C=CHCH_2CH_2CH_2CH_2-$. Representative, non-limiting examples of alkynyl groups are shown by the following structures; $HC\equiv C-$, $HC\equiv CCH_2-$, $HC\equiv CC\underline{H}(CH_3)-$, $HC\equiv CC(CH_3)_2-$, and $HC\equiv CC(CH_3)_2CH_2-$.

In other embodiments, the hydrocarbon containing 6-30 carbons having one terminal unsaturated aliphatic group may be selected from α-olefins, such as 1-hexene, 1-octene, 1-decene, 1-undecene, 1-decadecene, and similar homologs. Alternatively, the optional compound may also be selected from aryl containing hydrocarbons, such as α-methyl styrene.

Still further, the optional compound may be selected from those polyoxyalkylenes having the average formula: R'O—[$(C_2H_4O)_{c'}(C_3H_6O)_{d'}(C_4H_8O)_{e'}$]—R" where R' is a monovalent unsaturated aliphatic hydrocarbon group containing 2-12 carbon atoms, c' is from 0-100, d' is from 0-100, and "e" is from 0-100, provided the sum of c', d', and e is >0. R" is hydrogen, an acyl group, or a monovalent hydrocarbon group containing 1-8 carbons.

Representative, non-limiting examples of polyoxyalkylenes, useful as the optional compound include; $H_2C=CHCH_2O(C_2H_4O)_{c'}H$; $H_2C=CHCH_2O(C_2H_4O)_{c'}CH_3$; $H_2C=CHCH_2O(C_2H_4O)_{c'}C(O)CH_3$; $H_2C=CHCH_2O(C_2H_4O)_{c'}(C_3H_6O)_{d'}H$; $H_2C=CHCH_2O(C_2H_4O)_{c'}(C_3H_6O)_{d'}CH_3$; $H_2C=CHCH_2O(C_2H_4O)_{c'}C(O)CH_3$; $H_2C=C(CH_3)CH_2O(C_2H_4O)_{c'}H$; $H_2C=C\underline{H}C(CH_3)_2O(C_2H_4O)_{c'}H$; $H_2C=C(CH_3)CH_2O(C_2H_4O)_{c'}CH_3$; $H_2C=C(CH_3)CH_2O(C_2H_4O)_{c'}C(O)CH_3$; $H_2C=C(CH_3)CH_2O(C_2H_4O)_{c'}(C_3H_6O)_{d'}H$; $H_2C=C(CH_3)CH_2O(C_2H_4O)_{c'}(C_3H_6O)_{d'}CH_3$; $HC\equiv CCH_2O(C_2H_4O)_{c'}H$; $HC\equiv CCH_2O(C_2H_4O)_{c'}CH_3$; $HC\equiv CCH_2O(C_2H_4O)_{c'}(C_3H_6O)_{d'}H$; $HC\equiv CCH_2O(C_2H_4O)_{c'}(C_3H_6O)_{d'}CH_3$; and $HC\equiv CCH_2O(C_2H_4O)_{c'}C(O)CH_3$; wherein c' and d' are as described above.

In still other embodiments, the optional compound is a linear or branched siloxane with one unsaturated aliphatic group. Alternatively, the optional compound may be a polyol having one unsaturated aliphatic group (e.g. allyl xylitol or allyl glycerin).

Optional Silicone Elastomer(s):

The composition may also include a silicone elastomer that is different from each of the first and second components. The silicone elastomer is not particularly limited and may be any known in the art, as understood by those of skill in the art. Addition of the silicone elastomer allows the physical properties and sensory characteristics of the composition to be customized; however, it is to be appreciated that the silicone elastomer is optional. If the silicone elastomer is utilized, the composition may be referred to herein as the "silicone elastomer composition" or "elastomer composition".

Silicone Elastomer Composition:

The silicone elastomer composition can exhibit unique rheological, optical, and sensorial properties over wide concentrations. The chemical, and therefore physical, properties of such elastomer compositions can be modified such that the silicone elastomer compositions display hydrophilic or hydrophobic behavior, organic compatibility or incompatibility, and/or varying visual properties when disposed on skin. For example, specific silicone elastomer compositions can impart desirable properties which are more significant than the cumulative effects of their constituents. Choice of the fluid composition and silicone elastomer can modify rheology, improve sensory perceptions, change optical effects, and may increase the substantivity of the silicone elastomer compositions.

In one embodiment, "mismatched" carrier fluids are utilized to provide a dual sensory effect when the silicone elastomer compositions are applied to skin. For example, a blend of the silicone elastomer in volatile organic carrier fluid with the fluid composition in a nonvolatile silicone carrier fluid can exhibit a changing sensorial effect. Upon application, the effects of the volatile organic carrier fluid are easily discernible. However, after a period of time, the volatile organic carrier fluid can evaporate thereby showcasing the effects of the nonvolatile silicone carrier fluid.

Choice of components can add to substantivity of an elastomer/skin interaction and can improve durability. Choice of the fluid composition can modify the rheology of the silicone elastomer composition and can be customized for use in dual (or multi) sensory/texture products.

If utilized, the silicone elastomer is typically present in the silicone elastomer composition in an amount of from about 1-50, 2-40, 3-30, 3-25, 4-25, 5-25, 5-20, 5-15, 5-10, 5-9, 6-9, or 7-8, wt % based on 100 parts by weight of the silicone elastomer composition. It is contemplated that any and all values or ranges of values between those described above may also be utilized.

First Non-Limiting Example of a Suitable Silicone Elastomer:

A suitable silicone elastomer can be prepared by a cross-linking reaction between (A) ≡Si—H containing polysiloxanes and (B) an α,ω-diene in the presence of a platinum catalyst and (C) a low molecular weight linear or cyclic polysiloxane. The silicone elastomers can be swollen with the low molecular weight polysiloxane under a shear force. Elastomers containing 65-98 wt % of the low molecular weight polysiloxane are stable and form uniform silicone pastes with a wide viscosity range.

The silicone pastes tend to have excellent properties including clarity, thixotropy, shear thinning, and spread smoothly on the skin. They can be applied in cosmetic and medical products as the base oil. The silicone elastomers are capable of being crumbled to form a silicone powder. The silicone powder has the unique property of being easily rubbed-in on the skin, and silicone resins can be incorporated therein to improve the substantivity of formulations applied to the skin. These materials are ideal for use in solid cosmetics, such as antiperspirants and deodorants.

Component (A) is represented by compounds of the formula: $R_3SiO(R'_2SiO)_a(R''HSiO)_bSiR_3$ designated herein as type $A^1$, and compounds of the formula: $HR_2SiO(R'_2SiO)_cSiR_2H$ or formula: $HR_2SiO(R'_2SiO)_a(R''HSiO)_bSiR_2H$ designated herein as type $A^2$. In these formulas, R, R', and R", are alkyl groups with 1-6 carbon atoms; "a" is 0-250; "b" is 1-250; and "c" is 0-250. The molar ratio of compounds $A^2:A^1$ is 0-20 or 0-5. Compounds of types $A^1$ and $A^2$ can be used in the reaction; however, it is possible to successfully conduct the reaction using only compounds of type $A^1$.

Component (B) is a compound of the formula: $CH_2$=CH$(CH_2)_xCH$=$CH_2$ where x is 1-20. Examples of suitable α,ω-dienes are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

The addition and crosslinking reaction requires a catalyst to effect the reaction between components (A) and (B). Suitable catalysts are Group VIII transition metals, i.e., the noble metals. Such noble metal catalysts are described in U.S. Pat. No. 3,923,705, which is expressly incorporated herein by reference in one or more non-limiting embodiments to show platinum catalysts. Other suitable catalysts and amounts thereof are as described above, e.g. platinum group metal-containing catalysts.

One platinum catalyst type is Karstedt's catalyst, which is described in Karstedt's U.S. Pat. Nos. 3,715,334 and 3,814,730, which are each expressly incorporated herein by reference in one or more non-limiting embodiments. Karstedt's catalyst is a platinum divinyl tetramethyl disiloxane complex typically containing about one wt % of platinum in a solvent, such as toluene. Another platinum catalyst type is a reaction product of chloroplatinic acid and an organosilicon compound containing terminal aliphatic unsaturation. It is described in U.S. Pat. No. 3,419,593, which is expressly incorporated herein by reference in one or more non-limiting embodiments. The noble metal catalysts are used in amounts from 0.00001-0.5, 0.00001-0.02, or 0.00001-0.002, parts per 100 weight parts of component (A).

The phrase "low molecular weight silicone oil (C)" is intended to include (i) low molecular weight linear and cyclic volatile methyl siloxanes, (ii) low molecular weight linear and cyclic volatile and non-volatile alkyl and aryl siloxanes, and (iii) low molecular weight linear and cyclic functional siloxanes. Most preferred, however, are low molecular weight linear and cyclic volatile methyl siloxanes (VMS).

VMS compounds correspond to the average unit formula: $(CH_3)_aSiO_{(4-a)/2}$ in which "a" has an average value of 2-3. The VMS compounds contain siloxane units joined by ≡Si—O—Si≡ bonds. Representative siloxane units are $(CH_3)_3SiO_{1/2}$, $(CH_3)_2SiO_{2/2}$, $CH_3SiO_{3/2}$, and $SiO_{4/2}$, with inclusion of the latter two siloxane units resulting in the formation of branched linear or cyclic VMS.

Linear VMS have the formula: $(CH_3)_3SiO\{(CH_3)_2SiO\}_ySi(CH_3)_3$ where y is 0-5. Cyclic VMS have the formula: $\{(CH_3)_2SiO\}_z$ where z is 3-6. Typically, these VMS have boiling points less than about 250° C. and viscosities of about 0.65-5.0 mm²/s.

These VMS can be represented by the following structures wherein x and y are 0-5:

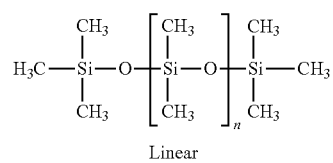

Linear

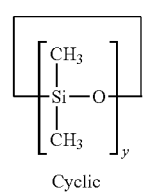

Cyclic

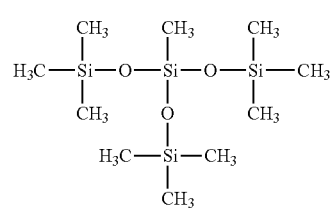

Branched Linear

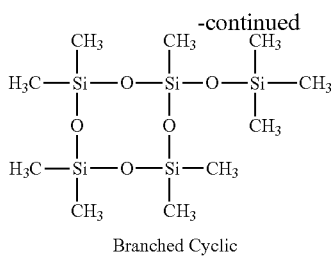

Branched Cyclic

Representative linear VMS (I) are hexamethyldisiloxane (MM) with a boiling point of 100° C., viscosity of 0.65 mm²/s, and formula Me₃SiOSiMe₃; octamethyltrisiloxane (MDM) with a boiling point of 152° C., viscosity of 1.04 mm²/s, and formula Me₃SiOMe₂SiOSiMe₃; decamethyltetrasiloxane (MD₂M) with a boiling point of 194° C., viscosity of 1.53 mm²/s, and formula Me₃SiO(Me₂SiO)₂SiMe₃; dodecamethylpentasiloxane (MD₃M) with a boiling point of 229° C., viscosity of 2.06 mm²/s, and formula Me₃SiO(Me₂SiO)₃SiMe₃; tetradecamethylhexasiloxane (MD₄M) with a boiling point of 245° C., viscosity of 2.63 mm²/s, and formula Me₃SiO(Me₂SiO)₄SiMe₃; and hexadecamethylheptasiloxane (MD₅M) with a boiling point of 270° C., viscosity of 3.24 mm²/s, and formula Me₃SiO(Me₂SiO)₅SiMe₃.

Representative cyclic VMS (11) are hexamethylcyclotrisiloxane (D₃) a solid with a boiling point of 134° C. and formula {(Me₂)SiO}₃; octamethylcyclotetrasiloxane (D₄) with a boiling point of 176° C., viscosity of 2.3 mm²/s, and formula {(Me₂)SiO}₄; decamethylcyclopentasiloxane (D₅) with a boiling point of 210 cc, viscosity of 3.87 mm²/s, and formula {(Me₂)SiO}₅; and dodecamethylcyclohexasiloxane (D₆) with a boiling point of 245° C., viscosity of 6.62 mm²/s, and formula {(Me₂)SiO}₆.

Representative branched VMS (III) and (IV) are heptamethyl-3-{(trimethylsilyl)oxy}trisiloxane (M₃T) with a boiling point of 192° C., viscosity of 1.57 mm²/s, and formula C₁₀H₃₀O₃Si₄; hexamethyl-3,3,bis{(trimethylsilyl)oxy}trisiloxane (M₄Q) with a boiling point of 222° C., viscosity of 2.86 mm²/s, and formula C₁₂H₃₆O₄Si₅; and pentamethyl {(trimethylsilyl)oxy}cyclotrisiloxane (MD₃) with the formula C₈H₂₄O₄Si₄.

Representative linear polysiloxanes are compounds of the formula $R_3SiO(R^2SiO)_ySiR_3$, and representative cyclic polysiloxanes are compounds of the formula $(R^2SiO)_z$. R is an alkyl group of 1-6 carbon atoms or an aryl group, such as phenyl. The value of "y" is 0-80 or 0-20. The value of "z" is 0-9 or 4-6. These polysiloxanes have viscosities generally in the range of about 1-100 mm²/s. The aforementioned viscosities are generally at 25° C. unless otherwise indicated.

Other representative low molecular weight non-volatile polysiloxanes have the general structure:

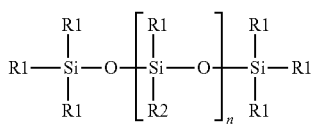

where "n" has a value to provide polymers with a viscosity in the range of about 100-1,000 centistokes. R1 and R2 are independently alkyl radicals of 1-20 carbon atoms or an aryl group, such as phenyl. Typically, the value of "n" is about 80-375. Illustrative polysiloxanes are polydimethylsiloxane, polydiethylsiloxane, polymethylethylsiloxane, polymethylphenylsiloxane, and polydiphenylsiloxane.

Low molecular weight functional polysiloxanes can be represented by acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

The ≡SiH containing polysiloxane(s), α,ω-diene, low molecular weight silicone oil or other solvent, and catalyst can be combined and mixed at room temperature until a gel is formed. Higher temperatures to speed up the process can be used, if desired. Additional amounts of the low molecular weight silicone oil or solvent are then added to the gel, and the resulting mixture is subjected to shear force to form the paste. Any type of mixing and shearing equipment may be used to perform these steps, such as a batch mixer, planetary mixer, single or multiple screw extruder, dynamic or static mixer, colloid mill, homogenizer, sonolator, or a combination thereof.

Typically, ~1:1 molar ratio of ≡Si—H containing polysiloxane and α,ω-diene is used. Materials may also be prepared by carrying out the process with an excess of either the —Si—H containing polysiloxane or the α,ω-diene, but this would be considered a less efficient use of the materials. The remainder of the composition comprises the low molecular weight silicone oil or other solvent in amounts generally within the range of about 65-98, or about 80-98, percent by weight of the composition.

Second Non-Limiting Example of a Suitable Silicone Elastomer:

Another suitable silicone elastomer can be obtained as hydrosilylation reaction products of an organohydrogensiloxane, an α,ω-unsaturated polyoxyalkylene, and a hydrosilylation catalyst, components (A), (B), and (C) respectively. The term "hydrosilylation" means the addition of an organosilicon compound containing silicon-bonded hydrogen, (such as component (A)) to a compound containing aliphatic unsaturation (such as component (B)), in the presence of a catalyst (such as component (C)). Hydrosilylation reactions are known in the art, and any such known methods or techniques may be used to effect the hydrosilylation reaction of components (A), (B), and (C) to prepare the silicone organic elastomers.

The silicone organic elastomer may also contain pendant, non-crosslinking moieties, independently selected from hydrocarbon groups containing 2-30 carbons, polyoxyalkylene groups, and mixtures thereof. Such pendant groups result from the optional addition of component (D') a hydrocarbon containing 2-30 carbons having one terminal unsaturated aliphatic group, and/or component (D") a polyoxyalkylene having one terminal unsaturated aliphatic group to the silicone organic elastomer via a hydrosilylation reaction.

The hydrosilylation reaction to prepare the silicone organic elastomer may be conducted in the presence of a solvent, and the solvent subsequently removed by known techniques. Alternatively, the hydrosilylation may be conducted in a solvent, where the solvent is the same as the carrier fluid described herein.

Component (A) is a linear or branched organohydrogensiloxane having an average, per molecule, of at least two SiH units. As used herein, an organohydrogensiloxane is any organopolysiloxane containing a silicon-bonded hydrogen atom (SiH). Organopolysiloxanes are polymers containing siloxy units independently selected from $(R_3SiO_{0.5})$, $(R^2SiO)$, $(RSiO_{1.5})$, or $(SiO_2)$ siloxy units, where R may be any organic group, e.g. a methyl group. These siloxy units can be combined in various manners to form cyclic, linear, or branched structures. The chemical and physical properties of the resulting polymeric structures can vary. For example organopolysiloxanes can be volatile or low viscosity fluids, high viscosity fluids/gums, elastomers or rubbers, and resins.

Organohydrogensiloxanes are organopolysiloxanes having at least one SiH containing siloxy unit, that is at least one siloxy unit in the organopolysiloxane has the formula: $(R_2HSiO_{0.5})$, $(RHSiO)$, or $(HSiO_{1.5})$. Thus, the organohydrogensiloxanes useful herein may comprise any number of $(R_3SiO_{0.5})$, $(R^2SiO)$, $(RSiO_{1.5})$, $(R_2HSiO_{0.5})$, $(RHSiO)$, $(HSiO_{1.5})$ or $(SiO_2)$ siloxy units, provided there are on average at least two SiH siloxy units in the molecule, and the organohydrogensiloxane is linear or branched. As used herein, "linear or branched" organohydrogensiloxane excludes cyclic organohydrogensiloxane structures. Component (A) can be a single linear or branched organohydrogensiloxane or a combination comprising two or more linear or branched organohydrogensiloxanes that differ in at least one of the following properties; structure, viscosity, average molecular weight, siloxane units, and sequence.

The organohydrogensiloxane may have the average formula: $(R^1_3SiO_{0.5})_v(R^2_2SiO)_x(R^2HSiO)_y$ where $R^1$ is hydrogen or $R^2$; $R^2$ is a monovalent hydrocarbyl; v is ≥2; x is ≥0, 1-500, or 1-200; and y is ≥2, 2-200, or 2-100.

$R^2$ may be a substituted or unsubstituted aliphatic or aromatic hydrocarbyl. Monovalent unsubstituted aliphatic hydrocarbyls are exemplified by, but not limited to alkyl groups, such as methyl, ethyl, propyl, pentyl, octyl, undecyl, and octadecyl and cycloalkyl groups, such as cyclohexyl. Monovalent substituted aliphatic hydrocarbyls are exemplified by, but not limited to halogenated alkyl groups, such as chloromethyl, 3-chloropropyl, and 3,3,3-trifluoropropyl. The aromatic hydrocarbon group is exemplified by, but not limited to, phenyl, tolyl, xylyl, benzyl, styryl, and 2-phenylethyl.

In one embodiment, the organohydrogensiloxane may contain additional siloxy units and have the average formula: $(R^1_3SiO_{0.5})_v(R^2_2SiO)_x(R^2HSiO)_y(R^2SiO_{1.5})_z$, $(R^1_3SiO_{0.5})_v(R^2_2SiO)_x(R^2HSiO)_y(SiO_2)_w$, $(R^1_3SiO_{0.5})_v(R^2_2SiO)_x(R^2HSiO)_y(SiO_2)_w(R^2SiO_{1.5})_z$, or any mixture thereof, where $R^1$ is hydrogen or $R^2$, $R^2$ is a monovalent hydrocarbyl, and v is ≥2, w is ≥0, x is ≥0, y is ≥2, and z is ≥0.

In one embodiment, the organohydrogensiloxane is selected from a dimethyl, methyl-hydrogen polysiloxane having the average formula: $(CH_3)_3SiO[(CH_3)_2SiO]_x[(CH_3)HSiO]_ySi(CH_3)_3$ where x is ≥0, 1-500, or 1-200; and y is ≥2, 2-200, or 2-100.

In one embodiment, the organohydrogensiloxane is mixture of dimethyl, methyl-hydrogen polysiloxane having the average formula: $(CH_3)_3SiO[(CH_3)_2SiO]_x[(CH_3)HSiO]_ySi(CH_3)_3$ and SiH terminal dimethyl polysiloxane having the average formula: $H(CH_3)_2SiO[(CH_3)_2SiO]_xSi(CH_3)_2H$ where x and y are as defined above. The amount of each organohydrogensiloxane in the mixture may vary, or alternatively may be such that in the mixture 0-85, 10-70, 20-60, or 30-50, wt % of the total SiH in the mixture is from the SiH content of the SiH terminal dimethyl polysiloxane. Methods for preparing organohydrogensiloxanes are well known, and many are sold commercially.

Component (B) is a polyoxyalkylene having an average formula: $R^3O—[(C_2H_4O)_c(C_3H_6O)_d(C_4H_8O)_e]—R^3$ where $R^3$ is a monovalent unsaturated aliphatic hydrocarbon group containing 2-12 carbon atoms; "c" is 0-50, 0-10, or <2; "d" is 0-100, 1-100, or 5-50; and "e" is 0-100, 0-50, or 0-30; with a proviso the ratio of (d+e)/(c+d+e) is >0.5, >0.8, or >0.95.

The polyoxyalkylene useful as component (B) can be any polyoxyalkylene that is terminated at each molecular chain end (i.e. a and w positions) with an unsaturated aliphatic hydrocarbon group containing 2-12 carbon atoms. The polyoxyalkylene may result from the polymerization of ethylene oxide, propylene oxide, butylene oxide, 1,2-epoxyhexane, 1,2-epoxyoctane, cyclic epoxides, such as cyclohexene oxide or exo-2,3-epoxynorbornane. The polyoxyalkylene group may comprise oxyethylene units $(C_2H_4O)$, oxypropylene units $(C_3H_6O)$, oxybutylene units $(C_4H_8O)$, or mixtures thereof. Typically, the polyoxyalkylene group comprises a majority of oxypropylene or oxybutylene units, as defined on a molar basis and indicated in the above formula by the "c", "d", and "e" subscripts. The unsaturated aliphatic hydrocarbon group can be an alkenyl or alkynyl group. Representative, non-limiting examples of the alkenyl and alkynyl groups are shown by the structures above.

In one embodiment, the polyoxyalkylene is selected from $H_2C=CHCH_2O[C_3H_6O]_dCH_2CH=CH_2$, $H_2C=C(CH_3)CH_2O[C_3H_6O]_dCH_2C(CH_3)=CH_2$, $HC≡CCH_2O[C_3H_6O]_dCH_2C≡CH$, and $HC≡CC(CH_3)_2O[C_3H_6O]_dC(CH_3)_2C≡CH$, where "d" is as defined above.

Polyoxyalkylenes having an unsaturated aliphatic hydrocarbon group at each molecular terminal are known in the art, and many are commercially available. Polyoxyalkylenes having an unsaturated aliphatic hydrocarbon group at each molecular terminal are commercially available from NOF (Nippon Oil and Fat, Tokyo, Japan) and Clariant Corp. (Charlottesville, N.C.).

The amounts of components (A) and (B) used in the hydrosilylation reaction may vary. Typically, the molar ratio of the SiH units of component (A) to the aliphatic unsaturated groups of component (B) ranges from 10/1 to 1/10, 5/1 to 1/5, or 2/1 to 1/2. In one embodiment, the molar ratio of the unsaturated aliphatic hydrocarbon groups in (B) to the SiH units in (A) is >1.

Component (C) comprises any catalyst typically employed for hydrosilylation reactions. Suitable catalysts and amounts thereof are as described above, e.g. platinum group metal-containing catalysts.

The silicone organic elastomer may also contain pendant, non-crosslinking moieties, independently selected from hydrocarbon groups containing 2-30 carbons, polyoxyalkylene groups, and mixtures thereof. These groups are formed on the silicone organic elastomer via a hydrosilylation reaction by the addition of component (D) an organic compound having one terminal unsaturated aliphatic hydrocarbon group. Component (D) may be selected from (D') a hydrocarbon containing 6-30 carbons having one terminal unsaturated aliphatic hydrocarbon group, and/or component (D") a polyoxyalkylene having one terminal unsaturated aliphatic group.

The addition of component (D) can alter the resulting chemical and physical properties of the silicone organic elastomer. For example, selecting (D') will result in the addition of hydrocarbon groups to the silicone organic elastomer, thus adding more hydrophobic character to the silicone organic elastomer. Conversely, selecting a polyoxyalkylene having a majority of ethylene oxide units will result in a silicone organic elastomer having increased hydrophilicity, which can subsequently incorporate water or hydrophilic components with the silicone organic elastomer to form dispersions or pastes.

The unsaturated aliphatic hydrocarbon group in (D') or (D") can be an alkenyl or alkynyl group. Representative, non-limiting examples of the alkenyl and alkynyl groups are shown by the structures above.

Component (D'), the hydrocarbon containing 6-30 carbons having one terminal unsaturated aliphatic group, may be selected from α-olefins, such as 1-hexene, 1-octene, 1-decene, 1-undecene, 1-decadecene, and similar homologs. Component (D') may also be selected from aryl containing hydrocarbons, such as α-methyl styrene.

Component (D") may be selected from those polyoxyalkylenes having the average formula: $R^3O—[(C_2H_4O)_{c'}(C_3H_6O)_{d'}(C_4H_8O)_{e'}]—R^4$ where $R^3$ is a monovalent unsaturated aliphatic hydrocarbon group containing 2-12 carbon atoms, c' is from 0-100, d' is from 0-100, and "e" is from 0-100, provided the sum of c', d', and e is >0. $R^4$ is hydrogen, an acyl group, or a monovalent hydrocarbon group containing 1-8 carbons. Representative, non-limiting examples of polyoxyalkylenes, useful as component (D") include: $H_2C=CHCH_2O(C_2H_4O)_{c'}H$; $H_2C=CHCH_2O(C_2H_4O)_{c'}CH_3$; $H_2C=CHCH_2O(C_2H_4O)_{c'}C(O)CH_3$; $H_2C=CHCH_2O(C_2H_4O)_{c'}(C_3H_6O)_{d'}H$; $H_2C=CHCH_2O(C_2H_4O)_{c'}(C_3H_6O)_{d'}CH_3$; $H_2C=CHCH_2O(C_2H_4O)_{c'}C(O)CH_3$; $H_2C=C(CH_3)CH_2O(C_2H_4O)_{c'}H$; $H_2C=CHC(CH_3)_2O(C_2H_4O)_{c'}H$; $H_2C=C(CH_3)CH_2O(C_2H_4O)_{c'}CH_3$; $H_2C=C(CH_3)CH_2O(C_2H_4O)_{c'}C(O)CH_3$; $H_2C=C(CH_3)CH_2O(C_2H_4O)_{c'}(C_3H_6O)_{d'}H$; $H_2C=C(CH_3)CH_2O(C_2H_4O)_{c'}(C_3H_6O)_{d'}CH_3$; $H_2C=C(CH_3)CH_2O(C_2H_4O)_{c'}C(O)CH_3$; $HC≡CCH_2O(C_2H_4O)_{c'}H$; $HC≡CCH_2O(C_2H_4O)_{c'}CH_3$; $HC≡CCH_2O(C_2H_4O)_{c'}C(O)CH_3$; $HC≡CCH_2O(C_2H_4O)_{c'}(C_3H_6O)_{d'}H$; $HC≡CCH_2O(C_2H_4O)_{c'}(C_3H_6O)_{d'}CH_3$; and $HC≡CCH_2O(C_2H_4O)_{c'}C(O)CH_3$; where c' and d' are as defined above.

The polyether may also be selected from those as described in U.S. Pat. No. 6,987,157, which is expressly incorporated herein by reference in one or more non-limiting embodiments for its teaching of polyethers.

Components (D') or (D") may be added to the silicone organic elastomer either during formation (i.e. simultaneously reacting components (A), (B), (C) and (D), in a first reaction (for example reacting a partial quantity of SiH groups of component (A) with (C) and (D)), followed by further reaction with (B) or subsequently added to a formed silicone organic elastomer having SiH content (for example, from unreacted SiH units present on the silicone organic elastomer).

The amount of component (D') or (D") used in the hydrosilylation reaction may vary, provided the molar quantity of the total aliphatic unsaturated groups present in the reaction from components (B) and (D) is such that the molar ratio of the SiH units of component (A) to the aliphatic unsaturated groups of components (B) and (D) ranges from 10/1 to 1/10.

Third Non-Limiting Example of a Suitable Silicone Elastomer:

Another suitable silicone elastomer can be obtained by reacting; (A) an organohydrogensiloxane comprising siloxy units of average formula: $(R^1_3SiO_{0.5})_v(R^2_2SiO)_x(R^2HSiO)_y$ where $R^1$ is hydrogen or $R^2$, $R^2$ is a monovalent hydrocarbyl, v is ≥2, x is ≥0, and y is ≥2; (B) a first polyoxyalkylene having the average formula: $R^3O—[(C_2H_4O)_c(C_3H_6O)_d(C_4H_8O)_e]—R^3$ where $R^3$ is a monovalent unsaturated aliphatic hydrocarbon group containing 2-12 carbon atoms, "c" is from 0-50, "d" is from 0-100, and "e" is from 0-100, with a proviso the ratio of (d+e)/(c+d+e) is >0.5; (C) a hydrosilylation catalyst; (D) a second polyoxyalkylene having the average formula: $R^3O—[(C_2H_4O)_{c'}(C_3H_6O)_{d'}(C_4H_8O)_{e'}]—R^4$ where $R^3$ is a monovalent unsaturated aliphatic hydrocarbon group containing 2-12 carbon atoms, c' is >4, d' and "e" may vary from 0-100, and $R^4$ is hydrogen, an acyl group, or a monovalent hydrocarbon group containing 1-8 carbons; in the presence of a hydrophobic carrier fluid.

Component (A) is a linear or branched organohydrogensiloxane having the average formula: $(R^1_3SiO_{0.5})_v(R^2_2SiO)_x(R^2HSiO)_y$ where $R^1$ is hydrogen or $R^2$; $R^2$ is a monovalent hydrocarbyl; v is ≥2; x is ≥0, 1-500, or 1-200; and y is ≥2, 2-200, or 2-100.

$R^2$ may be a substituted or unsubstituted aliphatic or aromatic hydrocarbyl. Monovalent unsubstituted aliphatic hydrocarbyls are exemplified by, but not limited to, alkyl groups, such as methyl, ethyl, propyl, pentyl, octyl, undecyl, and octadecyl and cycloalkyl groups, such as cyclohexyl. Monovalent substituted aliphatic hydrocarbyls are exemplified by, but not limited to, halogenated alkyl groups, such as chloromethyl, 3-chloropropyl, and 3,3,3-trifluoropropyl. The aromatic hydrocarbon group is exemplified by, but not limited to, phenyl, tolyl, xylyl, benzyl, styryl, and 2-phenylethyl.

In one embodiment, the organohydrogensiloxane may contain additional siloxy units and have the average formula: $(R^1_3SiO_{0.5})_v(R^2_2SiO)_x(R^2HSiO)_y(R^2SiO_{1.5})_z$, $(R^1_3SiO_{0.5})_v(R^2_2SiO)_x(R^2HSiO)_y(SiO_2)_w$, $(R^1_3SiO_{0.5})_v(R^2_2SiO)_x(R^2HSiO)_y(SiO_2)_w(R^2SiO_{0.5})_z$, or any mixture thereof, where $R^1$ is hydrogen or $R^2$, $R^2$ is a monovalent hydrocarbyl, and v is ≥2, w is ≥0, x is ≥0, y is ≥2, and z is ≥0.

In one embodiment, the organohydrogensiloxane is selected from a dimethyl, methyl-hydrogen polysiloxane having the average formula: $(CH_3)_3SiO[(CH_3)_2SiO]_x[(CH_3)HSiO]_ySi(CH_3)_3$ where x is ≥0, 1-500, or 1-200; and y is ≥2, 2-200, or 2-100. Methods for preparing organohydrogensiloxanes are well known, and many are sold commercially.

Component (B) is a polyoxyalkylene having the average formula: $R^3O—[(C_2H_4O)_c(C_3H_6O)_d(C_4H_8O)_e]—R^3$ where $R^3$ is a monovalent unsaturated aliphatic hydrocarbon group containing 2-12 carbon atoms; "c" is 0-50, 0-10, or ≥2; "d" is 0-100, 1-100, or 5-50; and "e" is 0-100, 0-50, or 0-30, with a proviso the ratio of (d+e)/(c+d+e) is >0.5, >0.8, or >0.95.

The polyoxyalkylene useful as component (B) is a polyoxyalkylene that is terminated at each molecular chain end (i.e. a and w positions) with an unsaturated aliphatic hydrocarbon group containing 2-12 carbon atoms. The polyoxyalkylene may result from the polymerization of ethylene oxide, propylene oxide, butylene oxide, 1,2-epoxyhexane, 1,2-epoxyoctane, cyclic epoxides, such as cyclohexene oxide or exo-2,3-epoxynorbornane. The polyoxyalkylene group may comprise oxyethylene units, oxypropylene units, oxybutylene units, or mixtures thereof. Typically, the polyoxyalkylene group comprises a majority of oxypropylene or oxybutylene units, as defined on a molar basis and indicated in the above formula by the "c", "d", and "e" subscripts. The unsaturated aliphatic hydrocarbon group can be an alkenyl or alkynyl group. Representative, non-limiting examples of the alkenyl and alkynyl groups are shown by the structures above.

In one embodiment, the polyoxyalkylene is selected from $H_2C=CHCH_2O[C_3H_6O]_dCH_2CH=CH_2$, $H_2C=C(CH_3)CH_2O[C_3H_6O]_dCH_2C(CH_3)=CH_2$, $HC≡CCH_2O[C_3H_6O]_dCH_2C≡CH$, and $HC≡CC(CH_3)_2O[C_3H_6O]_dC(CH_3)_2C≡CH$ where "d" is as defined above.

Polyoxyalkylenes having an unsaturated aliphatic hydrocarbon group at each molecular terminal are known in the art, and many are commercially available. Polyoxyalkylenes having an unsaturated aliphatic hydrocarbon group at each molecular terminal are commercially available from NOF (Nippon Oil and Fat, Tokyo, Japan) and Clariant Corp. (Charlottesville, N.C.).

Component (C) comprises any catalyst typically employed for hydrosilylation reactions. Suitable catalysts and amounts thereof are as described above, e.g. platinum group metal-containing catalysts.

This silicone organic elastomer contains pendant, non-crosslinking polyoxyalkylene groups. These groups are formed on the silicone organic elastomer via a hydrosilylation reaction by the addition of component (D) a second polyoxyalkylene having the average formula: $R^3O—[(C_2H_4O)_{c'}(C_3H_6O)_{d'}(C_4H_8O)_{e'}]—R^4$ where $R^3$ is a monovalent unsaturated aliphatic hydrocarbon group containing 2-12 carbon atoms, c' is >4, d' and e' may vary from 0-100, and $R^4$ is hydrogen, an acyl group, or a monovalent hydrocarbon group containing 1-8 carbons.

The unsaturated aliphatic hydrocarbon group in (D) can be an alkenyl or alkynyl group. Representative, non-limiting examples of the alkenyl and alkynyl groups are shown by the structures above. Representative, non-limiting examples of polyoxyalkylenes, useful as component (D), include the structures provided above for (D") where c' and d' are also as defined above.

The polyether may also be selected from those as described in U.S. Pat. No. 6,987,157, which is expressly incorporated herein by reference in one or more non-limiting embodiments for its teaching of polyethers.

Component (D) may be added to the silicone organic elastomer either during formation (i.e. simultaneously reacting components (A), (B), (C) and (D)), in a first reaction (for example reacting a partial quantity of SiH groups of component (A) with (C) and (D), followed by further reaction with (B) or subsequently added to a formed silicone organic elastomer having SiH content (for example, from unreacted SiH units present on the silicone organic elastomer).

The amount of components (A), (B), and (D) used in the hydrosilylation reaction may vary, provided the molar quantity of the total aliphatic unsaturated groups present in the reaction from components (B) and (D) is such that the molar ratio of the SiH units of component (A) to the aliphatic unsaturated groups of components (B) and (D) ranges from 10/1 to 1/10. However, typically the molar ratio of the unsaturated aliphatic hydrocarbon groups in (B) and (D) to the SiH units in (A) is >1 to ensure complete consumption of SiH.

The amounts and structures of (B) and (D) used in the hydrosilylation reaction may also vary. However, the amounts used and structures of (B) and (D) are such so as to provide a silicone organic elastomer having an ethylene oxide content of 2-25, 3-20, or 4-18, wt %. As used herein, ethylene oxide content refers to the average amount of "EO" groups (that is —$CH_2CH_2O$—) present on the silicone organic elastomer structure.

In one embodiment, the silicone organic elastomer is cross-linked with a polyoxypropylene chain and the silicone organic elastomer further contains pendant polyoxyethylene units. In this embodiment, component (B) is selected to contain only propylene oxide as the polyoxyalkylene groups and component (D) contains only ethylene oxide as the polyoxyalkylene groups. Thus, in this embodiment, component (B) has the formula: $R^3O—[(C_3H_6O)_{d'}]—R^3$ where $R^3$ is the same as defined above, and d' is >0, 4-50, or 10-30. Sufficient amounts of component (B) are used to provide the silicone elastomer with a propylene oxide content of 5-50 wt %. In this embodiment, component (D) has the formula: $R^3O—[(C_2H_4O)_{c'}]—R^4$ where $R^3$ and $R^4$ are the same as defined above, and c' is >4, 4-50, or 10-30. Sufficient amounts of component (D) are used to provide the silicone elastomer with an ethylene oxide content of 2-25 wt %.

The order of addition of components (A), (B), (C) and (D) may vary. However, in one embodiment, the reaction to prepare the silicone elastomer proceeds in two steps. The first reacts components (A), (C), and (D) to form an organohydrogensiloxane polyoxyethylene copolymer, the second reacts the organohydrogensiloxane polyoxyethylene copolymer with component (B) and additional quantities of (C).

In still additional embodiments, the silicone elastomer is a cross-linked silicone elastomer, e.g. cross-linked as a solution in a solvent or oil or carrier fluid. In one embodiment, cross-linked silicone elastomers include a solvent which serves to suspend and swell the elastomer particles to provide an elastic, gel-like network or matrix. The solvent is liquid under ambient conditions and preferably has a low viscosity for spreading on the skin. The liquid carriers may be organic, silicone-containing, or fluorine-containing, volatile or non-volatile, polar or non-polar or combinations of any of these.

In other embodiments, the silicone elastomer is a hydrophobic or non-emulsifying cross-linked silicone elastomer. Typically, these are the reaction product of SiH containing polysiloxanes (or resins) and $\alpha,\omega$-dienes in the presence of a platinum catalyst and carrier fluid. The $\alpha,\omega$-dienes are typically organopolysiloxanes (alkenyl functional polysiloxanes or resins) and/or hydrocarbons but usually do not contain polyoxyalkylene groups (either as crosslinking species or pendant side chains). These elastomers may also have pendant branches of silicone or organic (hydrocarbon, phenyl, etc.) side chains.

In still other embodiments, the silicone elastomer is an organic compatible hydrophobic or non-emulsifying cross-linked silicone elastomer. These elastomers tend to have increased compatibility with organic ingredients by either/or: attaching more or longer organic pendant side chains or crosslinking groups (hydrocarbon or polyoxypropylene dienes) and/or use of organic solvents. These elastomers may also have pendant branches of silicone or organic (hydrocarbon, phenyl, etc.) side chains. Typically, no pendant or crosslinking moieties based on polyoxyalkylene or polyglycerol species are present.

In further embodiments, the silicone elastomer is a hydrophilic or emulsifying cross-linked silicone elastomer. These elastomers tend to be differentiated from those above by having at least one polyoxyalkylene (polyoxyethylene (EO) or polyoxypropylene (PO) or polyglycerol), or other hydroxyl groups or other moieties which instill hydrophilicity to produce a material that is primarily hydrophobic in character, but is still sufficiently hydrophilic in order to be compatible with water and other polar solvents/ingredients. These polyoxyalkylene species can be either crosslinking components, pendant side chains or both. In addition, these elastomers may also have pendant branches of silicone or organic (hydrocarbon, phenyl, etc.) side chains. Specific examples of suitable silicone elastomers for the composition include those in DOW CORNING® EL-7040, EL-8040, and EL-9240.

Optional Emulsion:

The composition may be provided as an emulsion. As used herein, "emulsion" describes water continuous emulsions (for example an oil in water emulsion, or a silicone in water emulsion), oil or silicone continuous emulsions (water in oil emulsions or water in silicone emulsions), or multiple emulsions (water/oil/water, oil/water/oil types, water/silicone/water, or silicone/water/silicone). The composition may be provided as an emulsion using any techniques of the art, such as stirring, homogenizing, and sonalating, e.g. a batch, semi-continuous, or continuous process.

The amount of the composition used to form the emulsion can vary and is not limited. However, the amount typically may be from a vesicle/emulsion weight ratio of 0.1/99 to 99/0.1 or 1/99 to 99/1.

The emulsion may be w/o, w/s, or a multiple phase emulsion, as known in the art, e.g. using silicone emulsifiers. Typically a water-in-silicone emulsifier is utilized in such a formulation, is typically non-ionic, and is typically chosen from polyoxyalkylene-substituted silicones, silicone alkanolamides, silicone esters, silicone glycosides, and combinations thereof. Silicone-based surfactants may be used to form such emulsions, such as those described in U.S. Pat. Nos. 4,122,029, 5,387,417, and 5,811,487, each of which is expressly incorporated herein by reference in one or more non-limiting embodiments. Thickening agents may also be utilized, such as DOW CORNING® RM 2051.

In one embodiment, the emulsion is an oil in water emulsion and may include nonionic surfactants, such as polyoxyethylene alkyl ethers, polyoxyethylene alkylphenol ethers, polyoxyethylene lauryl ethers, polyoxyethylene sorbitan monooleates, polyoxyethylene alkyl esters, polyoxyethylene sorbitan alkyl esters, polyethylene glycol, polypropylene glycol, diethylene glycol, ethoxylated trimethylnonanols, polyoxyalkylene glycol modified polysiloxane surfactants, and combinations thereof.

Personal Care Composition:

This disclosure also provides a personal care composition, which may also be referred to herein as a "personal care product". The personal care composition includes the fluid composition described above. The personal care composition may be in the form of a cream, a gel, a powder, a paste, or a freely pourable liquid. Generally, such personal care compositions can generally be prepared at room temperature if no solid materials at room temperature are present in the personal care compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care composition can be used in or for a variety of personal, household, and healthcare applications. In particular, the fluid composition and/or personal care composition of the present disclosure may be used in the personal care products as described in U.S. Pat. Nos. 6,051,216, 5,919,441, 5,981,680; WO2004/060271 and WO2004/060101; in sunscreen compositions as described in WO2004/060276; in cosmetic compositions also containing film-forming resins, as described in WO03/105801; in the cosmetic compositions as described in US Pub. Nos. 2003/0235553, 2003/0072730 and 2003/0170188, in EP Pat. Nos. 1,266,647, 1,266,648, and 1,266,653, in WO03/105789, WO2004/000247 and WO03/106614; as additional agents to those described in WO2004/054523; in long wearing cosmetic compositions as described in US Pub. No. 2004/0180032; and/or in transparent or translucent care and/or make up compositions as described in WO2004/054524; all of which are expressly incorporated herein by reference in various non-limiting embodiments.

The personal care products may be functional with respect to the portion of the body to which they are applied, cosmetic, therapeutic, or some combination thereof. Conventional examples of such personal care products include, but are not limited to: antiperspirants and deodorants; skin care creams, skin care lotions, moisturizers, and facial treatments, such as acne or wrinkle removers; personal and facial cleansers; bath oils; perfumes and colognes; sachets; sunscreens; pre-shave and after-shave lotions; shaving soaps, and shaving lathers; hair shampoos, hair conditioners, hair colorants, hair relaxants, hair sprays, mousses, gels, permanents, depilatories, and cuticle coats; make-ups, color cosmetics, foundations, concealers, blushes, lipsticks, eyeliners, mascara, oil removers, color cosmetic removers, and powders; and medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

Personal care compositions for personal care may alternatively be referred to as cosmetic compositions and include those that are intended to be placed in contact with external portions of the human body (skin, hair, nails, mucosa, etc., also referred to as "keratinous substrates") or with the teeth and the mucous membranes of the oral cavity with a view exclusively or mainly to cleaning them, perfuming them, changing their appearance, protecting them, keeping them in good condition or modifying odors. In some instances, personal care compositions also include health care compositions. Cosmetic applications, and in some instances health care applications, include skin care, sun care, hair care, or nail care applications.

Personal care ingredients are those components used in personal care or cosmetic applications. A wide review of such components may be found in the CTFA cosmetic component handbook. Exemplary personal care ingredients are described in further detail below. These personal care ingredients may alternative be referred to as cosmetic components, health care components, etc. depending on the typical use thereof. When the personal care ingredient is the cosmetic component, the personal care composition is referred to as a cosmetic composition; when the personal care ingredient is the health care component, the personal care composition is referred to as a health care composition, etc.

Cosmetic components include emollients, waxes, moisturizers, surface active materials (such as surfactants or detergents or emulsifiers), thickeners, water phase stabilizing agents, pH controlling agents, preservatives and cosmetic biocides, sebum absorbants or sebum control agents, vegetable or botanical extracts, vitamins, proteins or aminoacids and their derivatives, pigments, colorants, fillers, silicone conditioning agents, cationic conditioning agents, hydrophobic conditioning agents, UV absorbers, sunscreen agents, antidandruff agents, antiperspirant agents, deodorant agents, skin protectants, hair dyes, nail care components, fragrances or perfume, antioxidants, oxidizing agents, reducing agents, propellant gases, and mixtures thereof. Additional components that may be used in the cosmetic compositions include fatty alcohols, color care additives, anticellulites, pearlising agents, chelating agents, film formers, styling agents, ceramides, suspending agents and others.

Health care components include antiacne agents, antibacterial agents, antifungal agents, therapeutic active agents, external analgesics, skin bleaching agents, anti-cancer agents, diuretics, agents for treating gastric and duodenal ulcers, proteolytic enzymes, antihistamine or H1 histamine blockers, sedatives, bronchodilators, diluents, and others. Additional components that may be used in the health care compositions include antibiotics, antiseptics, antibacterial agents, anti-inflammatory agents, astringents, hormones, smoking cessation compositions, cardiovascular agents, antiarrhythmic agents, alpha-I blockers, beta blockers, ACE inhibitors, antiaggregants, non-steroidal anti-inflammatory agents (NSAIDs; such as diclofenac), antipsoriasis agents (such as clobetasol propionate), antidermatitis agents, tranquilizer, anticonvulsants, anticoagulant agents, healing factors, cell growth nutrients, peptides, corticosteroidal drugs, antipruritic agents and others.

Cosmetic components may be used in health care compositions, such as waxes, and others; and health care components may be used in cosmetic compositions, such as anti-acne agents, and others.

Examples of emollients include volatile or non-volatile silicone oils; silicone resins, such as polypropylsilsesquioxane and phenyl trimethicone; silicone elastomers, such as dimethicone cross-polymers; alkylmethylsiloxanes, such as $C_{30-45}$ alkyl methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa-decane; branched $C_8$-$C_{16}$ esters; isohexyl neopentanoate; ester oils, such as isononyl isononanoate, cetostearyl octanoate, isopropyl myristate, palmitate derivatives, stearates derivatives, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; triglycerides of caprylic/capric acids; higher fatty acids, such as oleic acid, linoleic acid or linolenic acid; and mixtures thereof.

Examples of waxes include hydrocarbon waxes, such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, $C_{30}$-$C_{45}$ allyldimethylsilyl polypropylsilsesquioxane), and mixtures thereof Examples of moisturizers include lower molecular weight aliphatic diols, such as propylene glycol and butylene glycol; polyols, such as glycerine and sorbitol; and polyoxyethylene polymers, such as polyethylene glycol 200; hyaluronic acid and its derivative; and mixtures thereof.

Examples of surface active materials may be anionic, cationic or nonionic, and include organomodified silicones, such as dimethicone copolyol; oxyethylenated and/or oxypropylenated ethers of glycerol; oxyethylenated and/or oxypropylenated ethers of fatty alcohols, such as ceteareth-30, $C_{12}$-$C_{15}$ pareth-7; fatty acid esters of polyethylene glycol, such as PEG-50 stearate and PEG-40 monostearate; saccharide esters and ethers, such as sucrose stearate, sucrose cocoate and sorbitan stearate, and mixtures thereof; phosphoric esters and salts thereof, such as DEA oleth-10 phosphate; sulphosuccinates, such as disodium PEG-5 citrate lauryl sulphosuccinate and disodium ricinoleamido MEA sulphosuccinate; alkyl ether sulphates, such as sodium lauryl ether sulphate; isethionates; betaine derivatives; and mixtures thereof.

Further examples of nonionic surfactants include polyoxyethylene alkyl ethers, polyoxyethylene alkylphenol ethers, polyoxyethylene lauryl ethers, polyoxyethylene sorbitan monooleates, polyoxyethylene alkyl esters, polyoxyethylene sorbitan alkyl esters, polyethylene glycol, polypropylene glycol, diethylene glycol, ethoxylated trimethylnonanols, polyoxyalkylene-substituted silicones (rake or ABn types), silicone alkanolamides, silicone esters, silicone glycosides, and mixtures thereof.

Nonionic surfactants include dimethicone copolyols, fatty acid esters of polyols, for instance sorbitol or glyceryl mono-, di-, tri- or sesqui-oleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl)ethers.

Anionic surfactants include carboxylates (sodium 2-(2-hydroxyalkyloxy)acetate)), amino acid derivatives (N-acylglutamates, N-acylgly-cinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof.

Amphoteric and zwitterionic surfactants include betaines, N-alkylamidobetaines and derivatives thereof, proteins and derivatives thereof, glycine derivatives, sultaines, alkyl polyaminocarboxylates and alkylamphoacetates, and mixtures thereof.

Examples of thickeners include acrylamide copolymers, acrylate copolymers and salts thereof (such as sodium polyacrylate), xanthan gum and derivatives, cellulose gum and cellulose derivatives (such as methylcellulose, methylhydroxypropylcellulose, hydroxypropylcellulose, polypropylhydroxyethylcellulose), starch and starch derivatives (such as hydroxyethylamylose and starch amylase), polyoxyethylene, carbomer, sodium alginate, arabic gum, cassia gum, guar gum and guar gum derivatives, cocamide derivatives, alkyl alcohols, gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate), polyols (glycerine, propylene glycol, butylene glycol, and sorbitol), alcohols (such as ethyl alcohol), hydrocolloids, and mixtures thereof.

Examples of pH controlling agents include any water soluble acid, such as a carboxylic acid or a mineral acid, such as hydrochloric acid, sulphuric acid, and phosphoric acid, monocarboxylic acid, such as acetic acid and lactic acid, and polycarboxylic acids, such as succinic acid, adipic acid, citric acid, and mixtures thereof.

Example of preservatives and cosmetic biocides include paraben derivatives, hydantoin derivatives, chlorhexidine and its derivatives, imidazolidinyl urea, phenoxyethanol, silver derivatives, salicylate derivatives, triclosan, ciclopirox olamine, hexamidine, oxyquinoline and its derivatives, PVP-iodine, zinc salts and derivatives, such as zinc pyrithione, and mixtures thereof.

Examples of sebum absorbants or sebum control agents include silica silylate, silica dimethyl silylate, dimethicone/vinyl dimethicone cross-polymer, polymethyl methacrylate, cross-linked methylmethacrylate, aluminum starch octenylsuccinate, and mixtures thereof.

Examples of vegetable or botanical extracts are derived from plants (herbs, roots, flowers, fruits, or seeds) in oil or water soluble form, such as coconut, green tea, white tea, black tea, horsetail, Ginkgo biloba, sunflower, wheat germ, seaweed, olive, grape, pomegranate, aloe, apricot kernel, apricot, carrot, tomato, tobacco, bean, potato, actzuki bean, catechu, orange, cucumber, avocado, watermelon, banana, lemon, palm, or mixtures thereof. Examples of herbal extracts include dill, horseradish, oats, neem, beet, broccoli, tea, pumpkin, soybean, barley, walnut, flax, ginseng, poppy, avocado, pea, sesame, and mixtures thereof.

Examples of vitamins include a variety of different organic compounds, such as alcohols, acids, sterols, and quinones. They may be classified into two solubility groups: lipid-soluble vitamins and water-soluble vitamins. Lipid-soluble vitamins that have utility in personal care compositions include retinol (vitamin A), ergocalciferol (vitamin D2), cholecalciferol (vitamin D3), phytonadione (vitamin K1), and tocopherol (vitamin E). Water-soluble vitamins that have utility in personal care compositions include ascorbic acid (vitamin C), thiamin (vitamin B1), niacin (nicotinic acid), niacinamide (vitamin B3), riboflavin (vitamin B2), pantothenic acid (vitamin B5), biotin, folic acid, pyridoxine (vitamin B6), and cyanocobalamin (vitamin B12). Additional examples of vitamins include derivatives of vitamins, such as retinyl palmitate (vitamin A palmitate), retinyl acetate (vitamin A acetate), retinyl linoleate (vitamin A linoleate), retinyl propionate (vitamin A propionate), tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxylated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), sodium tocopheryl phosphate, ascorbyl palmitate, ascorbyl dipalmitate, ascorbyl glucoside, ascorbyl tetraisopalmitate, tetrahexadecyl ascorbate, ascorbyl tocopheryl maleate, potassium ascorbyl tocopheryl phosphate, tocopheryl nicotinate, and mixtures thereof.

Examples of proteins or amino-acids and their derivatives include those extracted from wheat, soy, rice, corn, keratin, elastin or silk. Proteins may be in the hydrolyzed form and they may also be quaternized, such as hydrolyzed elastin, hydrolyzed wheat powder, hydrolyzed silk. Examples of protein include enzymes, such as hydrolases, cutinases, oxidases, transferases, reductases, hemicellulases, esterases, isomerases, pectinases, lactases, peroxidases, laccases, catalases, and mixtures thereof. Examples of hydrolases include proteases (bacterial, fungal, acid, neutral or alkaline), amylases (alpha or beta), lipases, mannanases, cellulases, collagenases, lisozymes, superoxide dismutase, catalase, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc., and mixtures thereof. Surface treatments include those treatments based on lecithin, silicone, silanes, fluoro compounds, and mixtures thereof.

Examples of fillers include talc, micas, kaolin, zinc or titanium oxides, calcium or magnesium carbonates, silica, silica silylate, titanium dioxide, glass or ceramic beads, polymethylmethacrylate beads, boron nitride, aluminum silicate, aluminum starch octenylsuccinate, bentonite, magnesium aluminum silicate, nylon, silk powder metal soaps derived from carboxylic acids having 8-22 carbon atoms, non-expanded synthetic polymer powders, expanded powders and powders from natural organic compounds, such as cereal starches, which may or may not be cross-linked, copolymer microspheres, polytrap, silicone resin microbeads, and mixtures thereof. The fillers may be surface treated to modify affinity or compatibility with remaining components.

Examples of silicone conditioning agents include silicone oils, such as dimethicone; silicone gums, such as dimethiconol; silicone resins, such as trimethylsiloxy silicate, and polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone cross-polymer, and silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives, such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23. Other categories of conditioners include cationic surfactants, such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)]

aminobenzoate, glyceryl aminobenzoate, homosalate, lawsone with dihydroxyacetone, menthyl anthranilate, octocrylene, ethyl hexyl methoxycinnamate, octyl salicylate, oxybenzone, padimate O, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic Acid, benzyl salicylate, bornelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, triPABA panthenol, urocanic acid, VA/crotonates/methacryloxybenzophenone-1 copolymer, and mixtures thereof.

Examples of antidandruff agents include pyridinethione salts, selenium compounds, such as selenium disulfide, and soluble antidandruff agents, and mixtures thereof.

Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, zinc ricinoleate, and mixtures thereof.

Examples of skin protectants include allantoin, aluminum acetate, aluminum hydroxide, aluminum sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of hair dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2-methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl)methyl)-1H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; *Haematoxylon brasiletto* wood extract; HC dyes; *Lawsonia inermis* (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl $C_{21}$-$C_{22}$ isoalkyl acidate; isatin; *Isatis tinctoria* leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; and 1,2,4-trihydroxybenzene.

Examples of nail care components include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; *Cetraria islandica* extract; *Chondrus crispus*; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

Examples of fragrances or perfume include hexyl cinnamic aldehyde; anisaldehyde; methyl-2-n-hexyl-3-oxo-cyclopentane carboxylate; dodecalactone gamma; methylphenylcarbinyl acetate; 4-acetyl-6-tert-butyl-1,1-dimethyl indane; patchouli; olibanum resinoid; labdanum; vetivert; copaiba balsam; fir balsam; 4-(4-hydroxy-4-methyl pentyl)-3-cyclohexene-1-carboxaldehyde; methyl anthranilate; geraniol; geranyl acetate; linalool; citronellol; terpinyl acetate; benzyl salicylate; 2-methyl-3-(p-isopropylphenyl)-propanal; phenoxyethyl isobutyrate; cedryl acetal; aubepine; musk fragrances; macrocyclic ketones; macrolactone musk fragrances; ethylene brassylate; and mixtures thereof. Further perfume components are described in detail in standard textbook references, such as Perfume and Flavour Chemicals, 1969, S. Arctander, Montclair, N.J.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, *Camellia sinensis* oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (*Melaleuca aftemifolia*) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Examples of oxidizing agents are ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof.

Examples of reducing agents are ammonium bisufite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioproprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of propellant gases include carbon dioxide, nitrogen, nitrous oxide, volatile hydrocarbons such as butane, isobutane, or propane, and chlorinated or fluorinated hydrocarbons such as dichlorodifluoromethane and dichlorotetrafluoroethane or dimethylether; and mixtures thereof.

Examples of antiacne agents include salicylic acid, sulfur benzoyl, peroxide, tretinoin, and mixtures thereof.

Examples of antibacterial agents include chlorohexadiene gluconate, alcohol, benzalkonium chloride, benzethonium chloride, hydrogen peroxide, methylbenzethonium chloride, phenol, poloxamer 188, povidone-iodine, and mixtures thereof.

Examples of antifungal agents include miconazole nitrate, calcium undecylenate, undecylenic acid, zinc undecylenate, and mixtures thereof.

Examples of therapeutic active agents include penicillins, cephalosporins, tetracyclines, macrolides, epinephrine, amphetamines, aspirin, acetominophen, barbiturates, catecholamines, benzodiazepine, thiopental, codeine, morphine, procaine, lidocaine, benzocaine, sulphonamides, ticonazole, perbuterol, furosamide, prazosin, hormones, prostaglandins, carbenicillin, salbutamol, haloperidol, suramin, indomethicane, diclofenac, glafenine, dipyridamole, theophylline, hydrocortisone, steroids, scopolamine, and mixtures thereof.

Examples of external analgesics are benzyl alcohol, *capsicum* oleoresin (*Capsicum frutescens* oleoresin), methyl salicylate, camphor, phenol, capsaicin, juniper tar (*Juniperus oxycedrus* tar), phenolate sodium (sodium phenoxide), *capsicum* (*Capsicum frutescens*), menthol, resorcinol, methyl nicotinate, turpentine oil (turpentine), and mixtures thereof. An example of a skin bleaching agent is hydroquinone.

Examples of diluents include silicon containing diluents, such as hexamethyldisiloxane, octamethyltrisiloxane, and other short chain linear siloxanes, such as octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, cyclic siloxanes, such as hexamethylcyclotrisiloxane, octamethylcyclotetrasiloxane, decamethylcyclopentasiloxane, dodecamethylcyclohexasiloxane; organic diluents, such as butyl acetate, alkanes, alcohols, ketones, esters, ethers, glycols, glycol ethers, and hydrofluorocarbons. Hydrocarbons include isododecane, isohexadecane, Isopar L ($C_{11}$-$C_{13}$), Isopar H ($C_{11}$-$C_{12}$), and hydrogenated polydecene. Ethers and esters include isodecyl neopentanoate, neopentylglycol heptanoate, glycol distearate, dicaprylyl carbonate, diethylhexyl carbonate, propylene glycol n-butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic diluents include fats, oils, fatty acids, and fatty alcohols.

The amount of the fluid composition in the personal care compositions described above may vary from about 0.1-95, 0.2-50, or 0.5-25, wt % based on 100 parts by weight of the personal care composition. The personal care ingredient is present in an amount of from about 0.01-99.99 wt % based on 100 parts by weight of the personal care composition. Combinations of different personal care ingredients may be utilized. It is contemplated that any and all values or ranges of values between those described above may also be utilized.

The personal care compositions may be in the form of a cream, a gel, a powder (free flowing powder or pressed), a paste, a solid, freely pourable liquid, or an aerosol. The personal care compositions may be in the form of mono-phasic systems; biphasic or alternate multi phasic systems; emulsions, e.g. oil-in-water, water-in-oil, silicone-in-water, water-in-silicone; multiple emulsions, e.g. oil-in-water-in-oil, polyol-in-silicone-in-water, oil-in-water-in-silicone.

Skin care compositions include shower gels; soaps; hydrogels; creams; lotions and balms; antiperspirants and deodorants, such as sticks, soft solid, roll on, aerosol, and pumpsprays; skin creams; skin care lotions; moisturizers; facial treatments, such as wrinkle control or diminishment treatments; exfoliates; body and facial cleansers; bath oils; perfumes; colognes; sachets; sunscreens; mousses; patches; pre-shave and after-shave lotions; shaving soaps; shaving lathers; depilatories; make-ups; color cosmetics; foundations; concealers; blushes; lipsticks; eyeliners; mascaras; oil removers; color cosmetic removers, powders, and kits thereof.

Hair care compositions include shampoos, rinse-off conditioners, leave-in conditioners and styling aids, gels, sprays, pomades, mousses, waxes, hair colorants, hair relaxants, hair straighteners, permanents, and kits thereof.

Nail care compositions include color coats, base coats, cuticle coats, nail hardeners, and kits thereof.

Health care compositions may be in the form of ointments, creams, gels, mousses, pastes, patches, spray on bandages, foams and/or aerosols or the like, medicament creams, pastes or sprays including anti-acne, dental hygienic, antibiotic, healing promotive, which may be preventative and/or therapeutic medicaments, and kits thereof.

The personal care compositions may be used by standard methods, such as applying them to the human or animal body, e.g. skin or hair, using applicators, brushes, applying by hand, pouring them and/or optionally rubbing or massaging the composition onto or into the body.

The personal care compositions can be applied topically to the desired area of the skin or hair in an amount sufficient to provide a satisfactory cleansing or conditioning of the skin or hair. The personal care compositions may be diluted with water prior to, during, or after topical application, and then subsequently rinsed or wiped off of the applied surface, for example rinsed off of the applied surface using water or a water-insoluble substrate in combination with water.

The personal care compositions may be used on hair in a conventional manner. An effective amount of the composition for washing or conditioning hair is applied to the hair, with the effective amount typically ranging from about 1-50 grams. Application to the hair typically includes working the personal care composition through the hair such that most or all of the hair is contacted with the personal care composition. These steps can be repeated as many times as desired to achieve the desired benefit.

Benefits obtained from using the personal care compositions on hair include one or more of the following benefits: color retention, improvement in coloration process, hair conditioning, softness, detangling ease, silicone deposition, anti-static, anti-frizz, lubricity, shine, strengthening, viscosity, tactile, wet combing, dry combing, straightening, heat protection, styling, and curl retention.

The personal care compositions may be used on skin in a conventional manner. An effective amount of the personal care composition for the purpose is applied to the skin, with the effective amount typically ranging from about 1-3 mg/cm$^2$. Application to the skin typically includes working the personal care composition into the skin as many times as desired to achieve the desired benefit.

Benefits obtained from using the personal care compositions on skin include one or more of the following benefits: stability in various formulations (o/w, w/o, anhydrous), utility as an emulsifier, level of hydrophobicity, organic compatibility, substantivity/durability, wash off resistance, interactions with sebum, performance with pigments, pH stability, skin softness, suppleness, moisturization, skin feel, long lasting, long wear, long lasting color uniformity, color enhancement, foam generation, optical effects (soft focus), and stabilization of actives.

The personal care composition may be used to care for keratinous substrates, to cleanse, to condition, to refresh, to make up, to remove make up, or to fix hair.

Optional Additional Component(s):

The personal care composition and/or the composition may also include a solvent, such as (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols, such as methanol, ethanol, 1-propanol, cyclohexanol, benzyl alcohol, 2-octanol, ethylene glycol, propylene glycol, and glycerol; aliphatic hydrocarbons, such as pentane, cyclohexane, heptane, VM&P solvent, and mineral spirits; alkyl halides, such as chloroform, carbon tetrachloride, perchloroethylene, ethyl chloride, and chlorobenzene; amines, such as isopropylamine, cyclohexylamine, ethanolamine, and diethanolamine; aromatic hydrocarbons, such as benzene, toluene, ethylbenzene, and xylene; esters, such as ethyl acetate, isopropyl acetate, ethyl acetoacetate, amyl acetate, isobutyl isobutyrate, and benzyl acetate; ethers, such as ethyl ether, n-butyl ether, tetrahydrofuran, and 1,4-dioxane; glycol ethers, such as ethylene glycol monomethyl ether, ethylene glycol monomethyl ether acetate, diethylene glycol monobutyl ether, and propylene glycol monophenyl ether; ketones, such as acetone, methyl ethyl ketone, cyclohexanone, diacetone alcohol, methyl amyl ketone, and diisobutyl ketone; petroleum hydrocarbons, such as mineral oil, gasoline, naphtha, kerosene, gas oil, heavy oil, and crude oil; lubricating oils, such as spindle oil and turbine oil; and fatty oils, such as corn oil, soybean oil, olive oil, rape seed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

Solvents may also include volatile flavoring agents, such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils, such as lemon, orange, lime, and grapefruit; fruit essences, such as apple, pear, peach, grape, strawberry, raspberry, cherry, plum, pineapple, and apricot; and other useful flavoring agents including aldehydes and esters, such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

Moreover, solvents may include volatile fragrances, such as natural products and perfume oils. Some representative natural products and perfume oils are ambergris, benzoin, civet, clove, leaf oil, jasmine, mate, mimosa, musk, myrrh, orris, sandalwood oil, and vetivert oil; aroma chemicals, such as amyl salicylate, amyl cinnamic aldehyde, benzyl acetate, citronellol, coumarin, geraniol, isobornyl acetate, ambrette, and terpinyl acetate; and the various classic family perfume oils, such as the floral bouquet family, oriental family, chypre family, woody family, citrus family, canoe family, leather family, spice family, and herbal family.

Other components that may be used to form the compositions and/or personal care compositions of this disclosure are described in U.S. Pat. Nos. 5,505,937; 6,071,503; 6,074,654; 6,139,823; 6,180,117; 6,967,024; 6,991,782; 7,871,633; 8,557,230; 8,586,013; 8,673,282; 8,603,444; 8,673,283; 8,673,284; 8,758,739; and 8,778,323; US Pub Nos. 2003/0235552; 2009/0036615; and 2012/0171137; JP Pat. App. Nos. 61-161211 and 61-158913; JP Pat. No. 61-18708; EP Pat. No. 0709083; and WO2010/149493 and WO2013/103832; each of which is expressly incorporated herein by reference in one or more non-limiting embodiments.

Method of Forming the Personal Care Composition:

This disclosure also provides a method of forming the personal care composition. The method includes combining a personal care product or any other similar compound, as described above, with the composition. It is contemplated that the personal care product may be present before, during, and/or the first and second components, and optionally the carrier fluid, are combined. In one embodiment, the composition is prepared individually and then combined later with the personal care composition ingredients. It is possible to include some personal care ingredients at a fluid reaction step (i.e., formation of a hydrosilylation reaction product, if utilized) but various factors may need to be controlled, such as reaction inhibition, temperature sensitivity of the ingredients, etc. Techniques known in the art for formation of personal care formulations, including but not limited to, mixing techniques, cold blends or application of heat to facilitate forming the personal care composition, can be used. The order of addition used herein can be any known in the art.

EXAMPLES

The following examples, illustrating the fluid composition of this disclosure, are intended to illustrate and not to limit the invention.

Rheological behaviors that distinguish pituitous fluids generally include "stringing" behavior whereby the fluids form long strings when, e.g., a small amount of the fluid is held between the fingers and the fingers are moved apart. This produces a string of fluid that can be stretched to very long distances before breaking and it is this type of behavior that led to initial use of the term "pituitous" (the term refers to materials that resemble mucus or phlegm).

Another rheological behavior of pituitous fluids is the generation of a normal force when these fluids are subjected to shear stress. The normal force is a force generated in a direction which is perpendicular to the direction of the shear stress. This behavior is illustrated FIG. 1.

FIG. 1 is a line graph illustrating normal stress as a function of shear rate of a first pituitous fluid composition and a first polydimethylsiloxane ("PDMS"). This data was generated by a controlled-stress rheometer in which the fluid was held between a flat disc (attached to the rheometer) and a stationary plate equipped with a load cell. A controlled amount of force (torque) was applied to shaft attached to the disc sample thus subjecting it to a shear stress. The torque was increased during the experiment and the disc rotates at an increasing rate which is recorded as the shear rate. As the fluid sample is being subjected to the shear stress, the normal force is recorded by the load cell.

This data clearly shows the difference between the PDMS (1,000 cSt) and the pituitous fluid (15% of pituitous fluid dispersed in $D_5$). The pituitous fluid develops a significant normal force when subjected to an increasing amount of shear stress whereas the PDMS does not.

It is thought that this rheological behavior is related to the extreme lubrication effect observed when these pituitous fluids are rubbed onto skin. The rubbing action subjects the fluid film to high levels of shear stress and this generates a normal force that resists the tendency of the fluid film to thin out as it is rubbed. The thicker film produces a stronger lubricating effect.

Abrasion Test Setup and Procedure:

Various example formulations of the fluid composition are prepared. The formulations include different ratios of the first and second components. The formulations also include carrier fluid and many formulations also include pigment. Test procedures are described below.

Abrasion Procedure:

The test method is briefly described as the following steps: 1) Hydrated collagen films are secured tightly on 3×2.5 inch polycarbonate blocks. 2) ~0.15-0.2 grams of each sample material/formulation is spread by finger on respective hydrated collagen films. The coated films are allowed to dry overnight. 3) For examples evaluated for sebum resistance, 0.04 grams of synthetic sebum is dropped onto each dried film to treat them with sebum. The sebum is gently spread using a small roller (~1 inch). The treated films are left at ambient condition for 3-4 hours before abrasion testing. 4) Abrasion testing on all the treated films is conducted by using a modified Gardner Abrasion Tester. Up to 100 abrasion cycles may be applied to each sample. L*a*b values of both sample and rubbing cloth can be recorded throughout abrasion cycles. 5) After abrasion, the visual appearance of both sample and rubbing cloth can be recorded using a digital camera.

Copolymer and Organopolysiloxane Resin:

Various formulations are prepared according to Table I below.

TABLE I

| Component | wt % |
| --- | --- |
| Carrier Fluid | 67.5 |
| Fluid Composition | 27.6 |
| Pigment | 4.9 |

Depending on the example, the Carrier Fluid can be isododecane or 2 cSt PDMS. The Pigment is Unipure Red LC381AS-EM Sensient. The pigment is utilized to ease visual and colorimeter inspection of the abrasion results.

The Fluid Composition includes various ratios of the first and second components as further detailed below. The 27.6 wt % is based on non-volatile content (NVC) of the fluid composition. For example, if an example has a 1:1 (or 50:50) blend ratio, the formulation would have 13.8 wt % of each of the first and second components, with the remainder being the carrier fluid and pigment. Likewise, if an example has a 3:1 (or 75:25) blend ratio, the formulation would have 20.7 wt % of the first component and 6.9 wt % of the second component, with the remainder being the carrier fluid and pigment. FIGS. 5 through 8 illustrate abrasion results of various blends of components according to the amounts in Table I.

Figure 5:
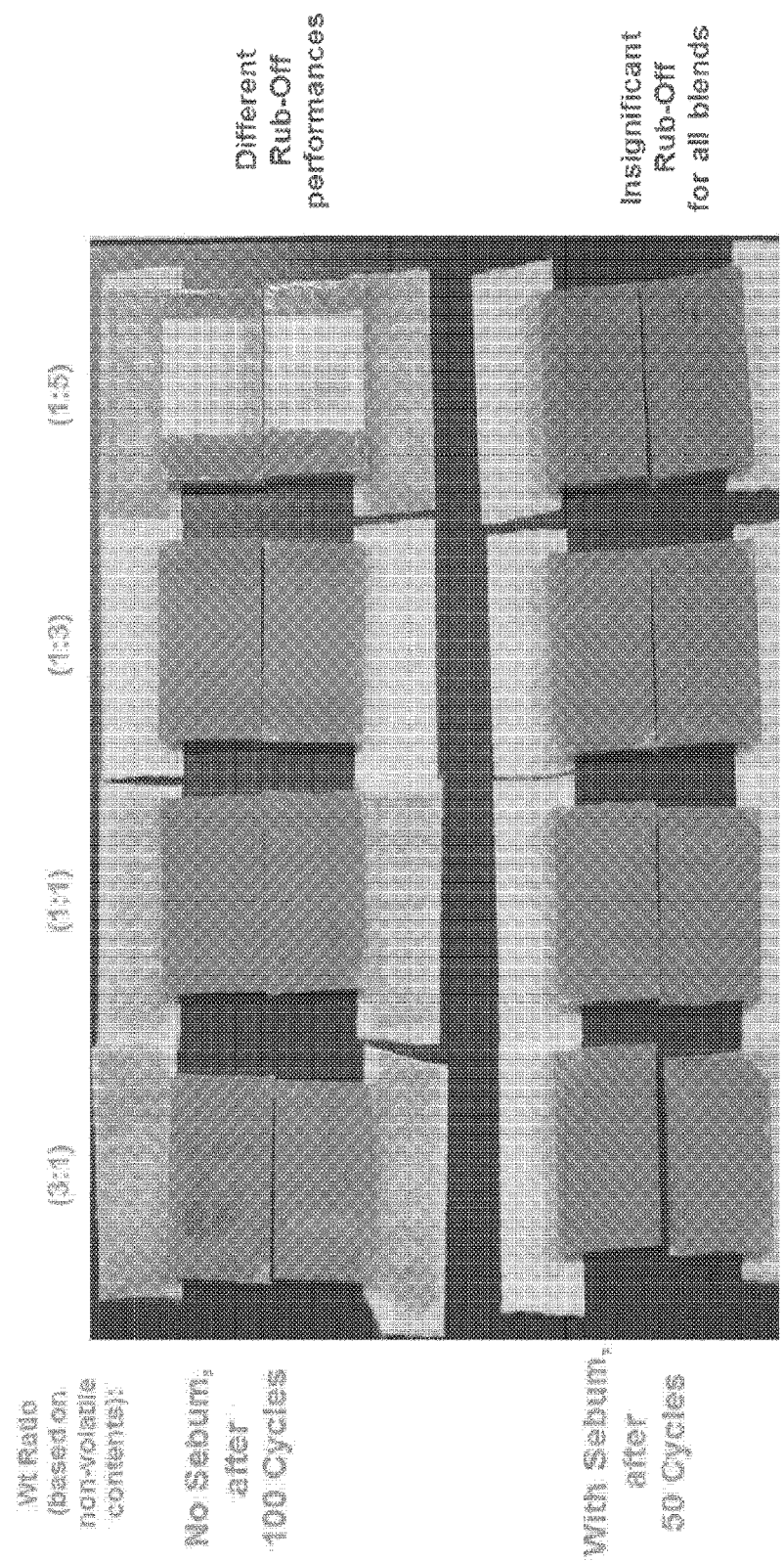
FIG. 5 is a photograph of abrasion test results of the Examples.

FIG. 5 depicts treated film abrasion results of different blends of a cross-linked aminosiloxane (Silicone Quaternium-16/Glycidoxy Dimethicone Crosspolymer) and an organopolysiloxane resin (100% trimethylsiloxysilicate resin). The cross-linked aminosiloxane can be prepared according to the general reaction scheme depicted in FIG. 4. From left to right, the blend ratios are 3:1, 1:1, 1:3, and 1:5, wt % of the cross-linked aminosiloxane and organopolysiloxane resin, respectively.

Figure 6A:
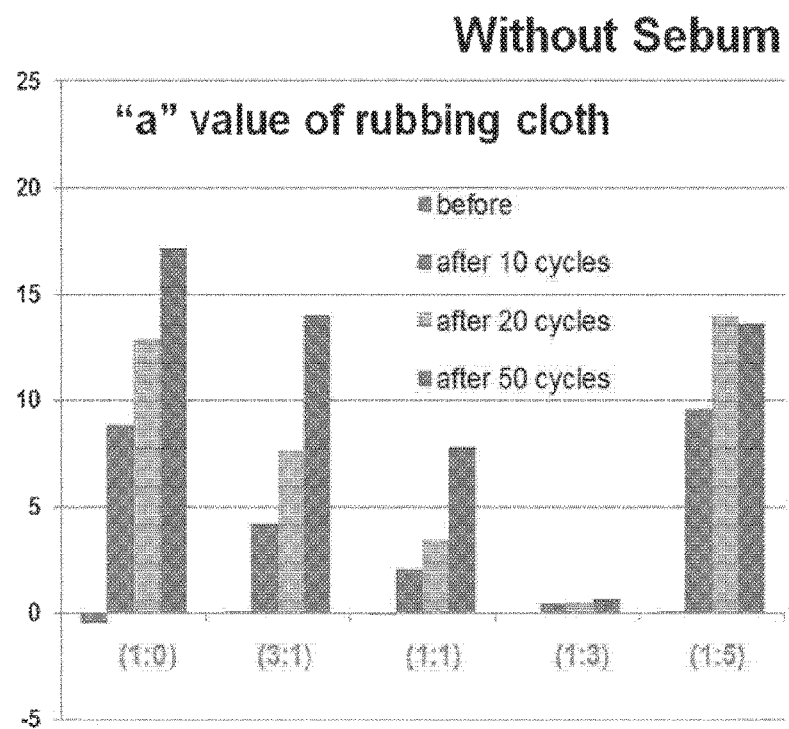
FIG. 6A is a bar graph illustrating abrasion test results of the Examples.
Figure 6B:
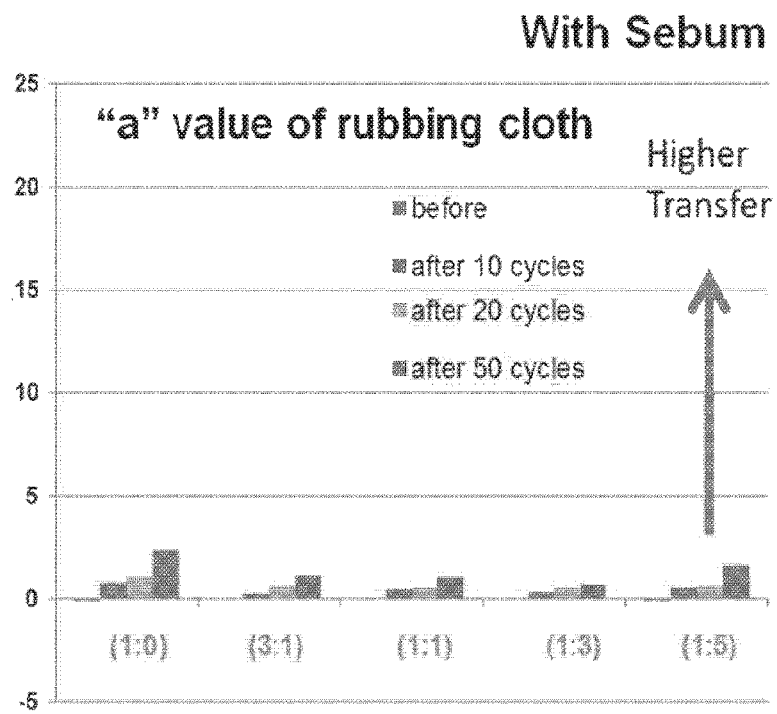
FIG. 6B is another bar graph illustrating abrasion test results of the Examples.

FIGS. 6A and 6B each depict colorimeter readings on the rubbing clothes used for the examples illustrated in FIG. 5. As understood in the art, "a" values of L*a*b are associated with the color red, and is most useful for determining the amount of transfer from a treated film to a rubbing cloth. Likewise, "a" values would also be useful if green pigment were to be used in place of red pigment, whereas "b" values would be useful if blue pigment or yellow pigment were to be used. Suitable colorimeters are available from numerous sources, e.g. BYK Gardner.

Figure 7:
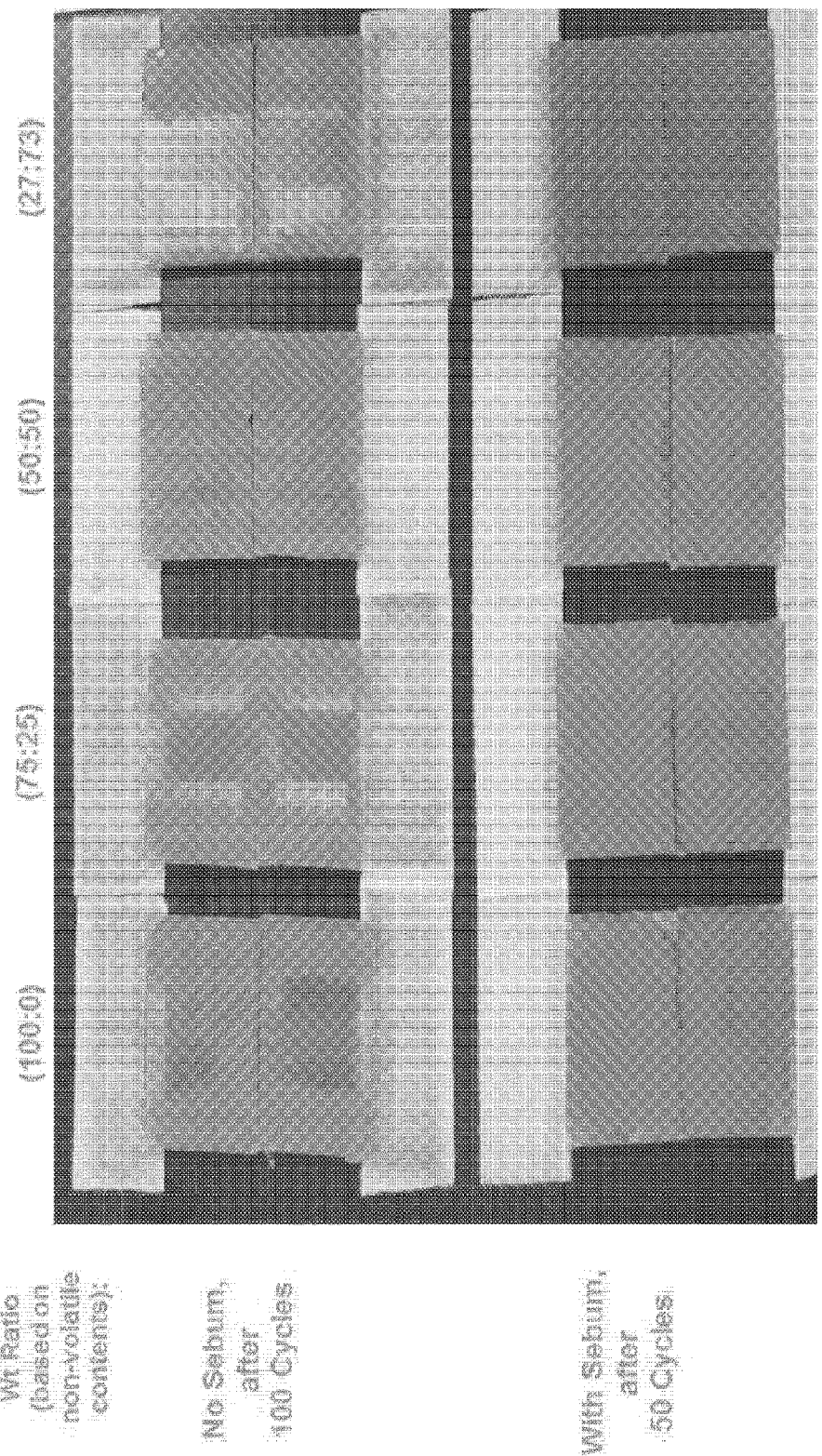
FIG. 7 is another photograph of abrasion test results of the Examples.

FIG. 7 depicts treated film abrasion results of different blends of another cross-linked aminosiloxane (an amino-functional PDMS having a viscosity of 3,500 cSt that is cross-linked with maleic anhydride) and the organopolysiloxane resin. The cross-linked aminosiloxane can be prepared according to the general reaction scheme depicted in FIG. 3. From left to right, the blend ratios are 100:0 (comparative example), 75:25, 50:50, and 27:73, wt % of the cross-linked aminosiloxane and organopolysiloxane resin, respectively.

Figure 8:
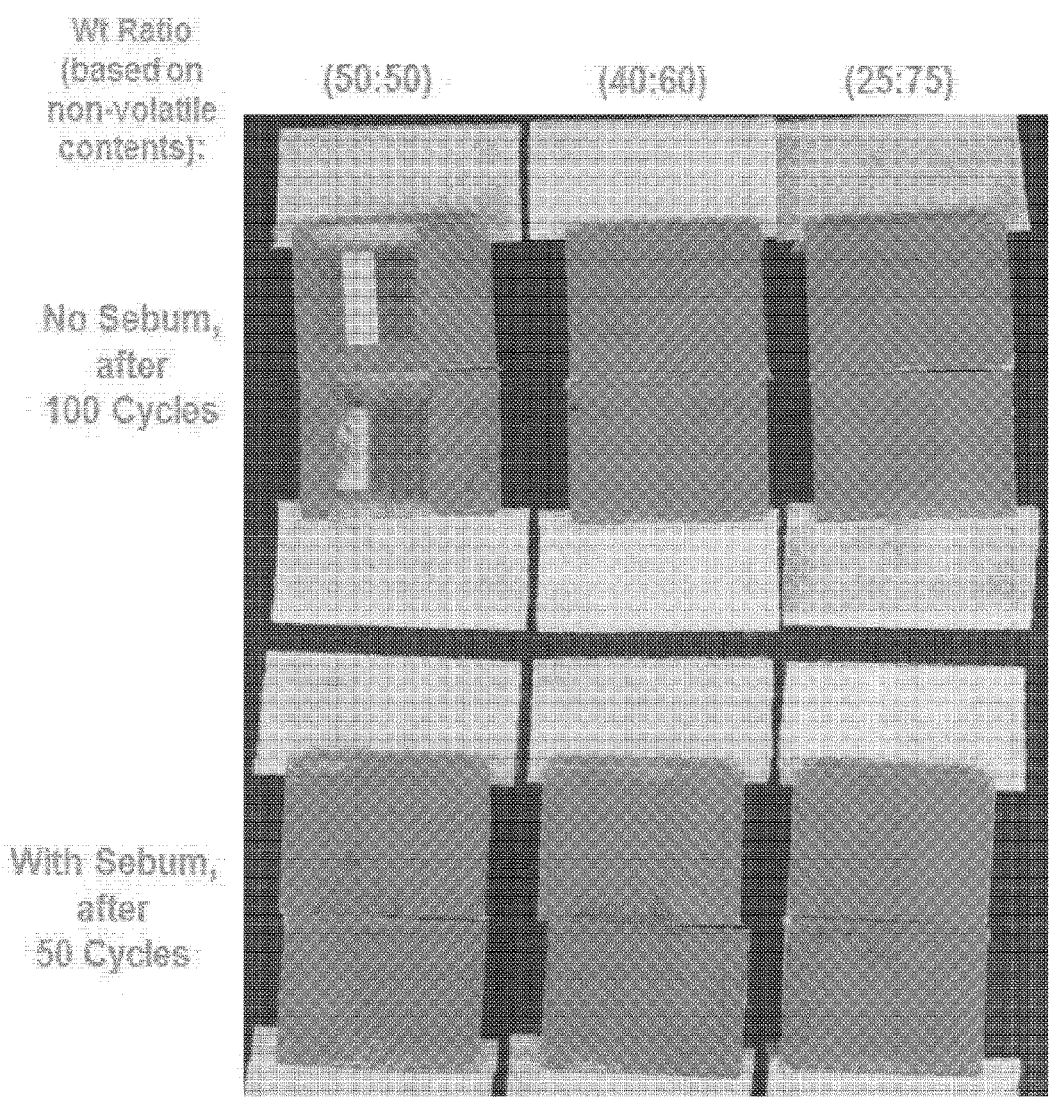
FIG. 8 is another photograph of abrasion test results of the Examples.

FIG. 8 depicts treated film abrasion results of different blends of the amino functional PDMS having a viscosity of 3,500 cSt and the organopolysiloxane resin. From left to right, the blend ratios are 50:50, 40:60, and 25:75, wt % of the amino functional PDMS and organopolysiloxane resin, respectively. These are comparative examples.

Copolymer and Acrylate Copolymer:

Various formulations are prepared according to Table II below.

TABLE II

| Component | wt % |
| --- | --- |
| Carrier Fluid | 67.5 |
| Fluid Composition | 27.6 |
| Pigment | 4.9 |

Depending on the example, the Carrier Fluid can be isododecane or 2 cSt PDMS. The Pigment is Unipure Red LC381AS-EM Sensient.

The Fluid Composition includes various ratios of the first and second components. The 27.6 wt % is based on NVC of the fluid composition. In all of the following formulations, the first component is a silicone polyether copolymer (PEG/PPG-18/18 Dimethicone) and the second component is an acrylate copolymer (Acrylates/Polytrimethylsiloxymethacrylate Copolymer).

Mixtures of the first and second components at different blend ratios were applied to glass slides (sans pigment). The treated glass slides were allowed to dry. After drying, transparent films were formed in all cases. Tack of the transparent films was tested and determined to be as follows (based on blend ratio of first and second components, respectively): 8:2="sticky"; 7:3="strong tack"; 6:4="light tack"; and "no tack" for each of 5:5, 4:6, and 3:7.

Mixtures of the first and second components at different blend ratios were applied to stainless steel (sans pigment). The treated stainless steel was allowed to dry. After drying, freestanding films can be peeled from the stainless steel surface, particularly for a 1:1 NVC wt % ratio of the first and second components.

Figure 9:
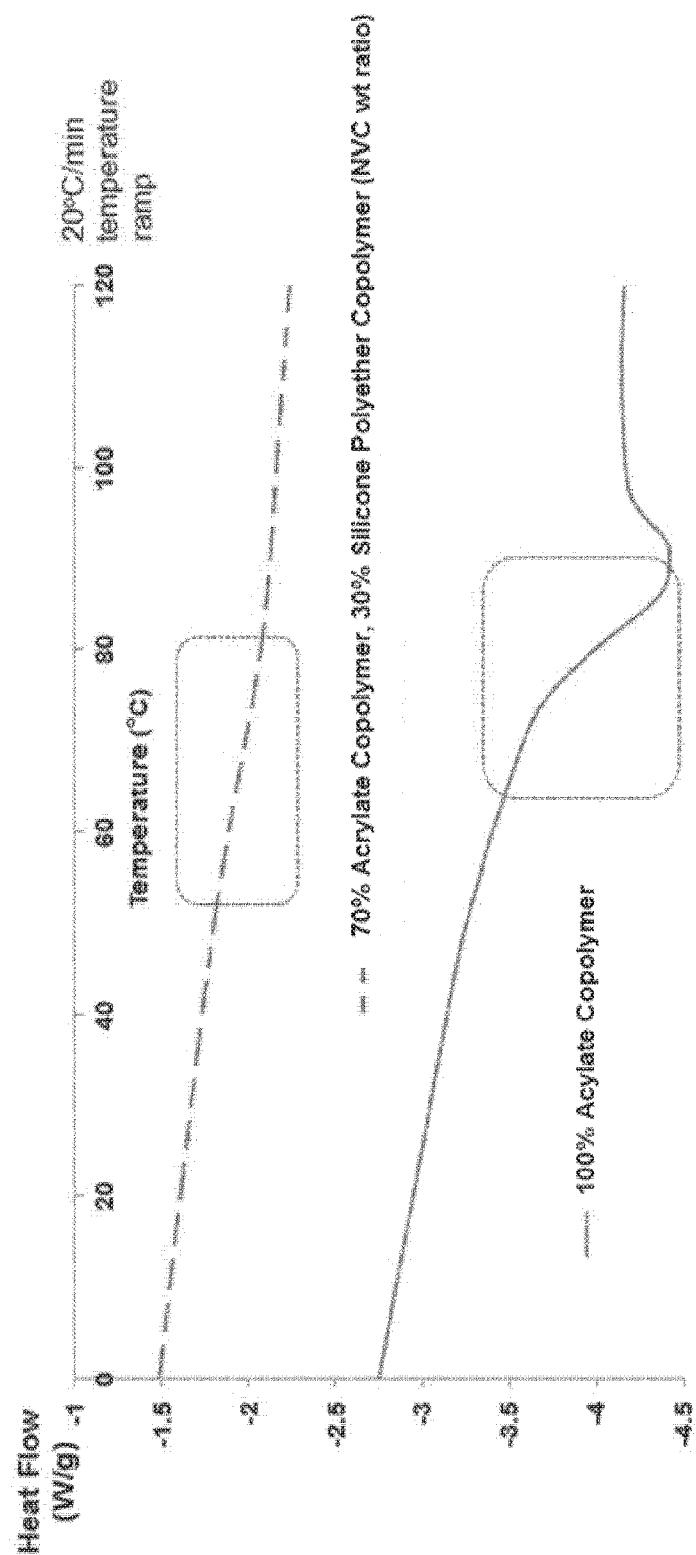
FIG. 9 is a line graph illustrating plasticization test results of the Examples.

Referring back to the Figures, FIG. 9 depicts the results of a differential scanning calorimetry (DSC) study. Depending on temperature ramping speed, the acrylate copolymer shows a distinct glass transition around 80° C. Adding the silicone polyether copolymer to the acrylate copolymer results in blends that have lower glass transition temperature (Tg) and broader (less distinct) glass transitions.

A blend of the acrylate copolymer: the silicone polyether copolymer at a 7:3 NVC wt % ratio has a less distinguishable glass transition around 65° C. The acrylate copolymer: the silicone polyether copolymer at a 6:4 NVC wt % ratio has even less distinguishable glass transition around ~59° C.

Figure 10:
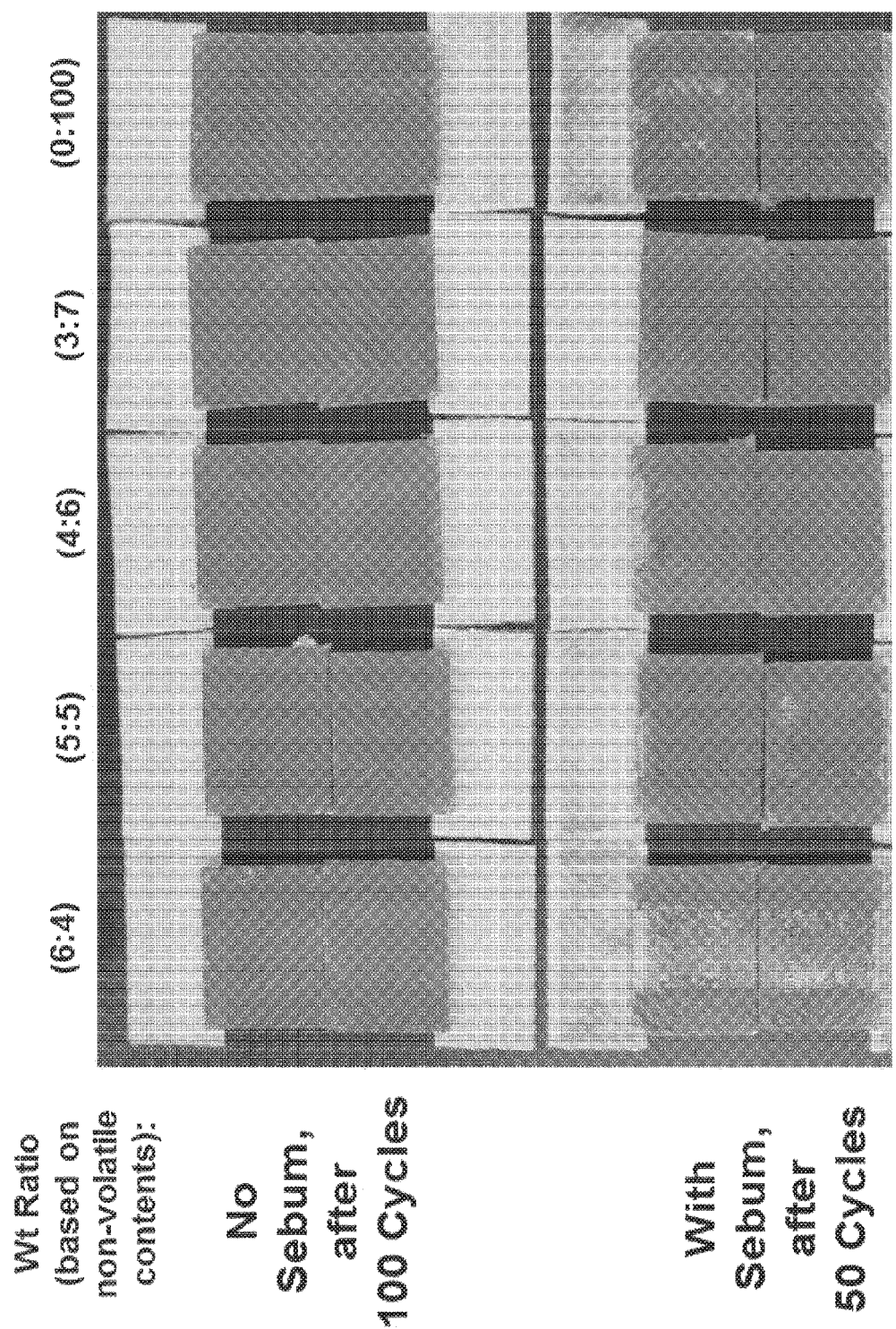
FIG. 10 is another photograph of abrasion test results of the Examples.

FIG. 10 depicts treated film abrasion results of different blends of the silicone polyether copolymer and the acrylate copolymer. From left to right, the blend ratios are 6:4, 5:5, 4:6, 3:7; and 0:100 (comparative example), wt % of the first and second components, respectively.

Figure 11:
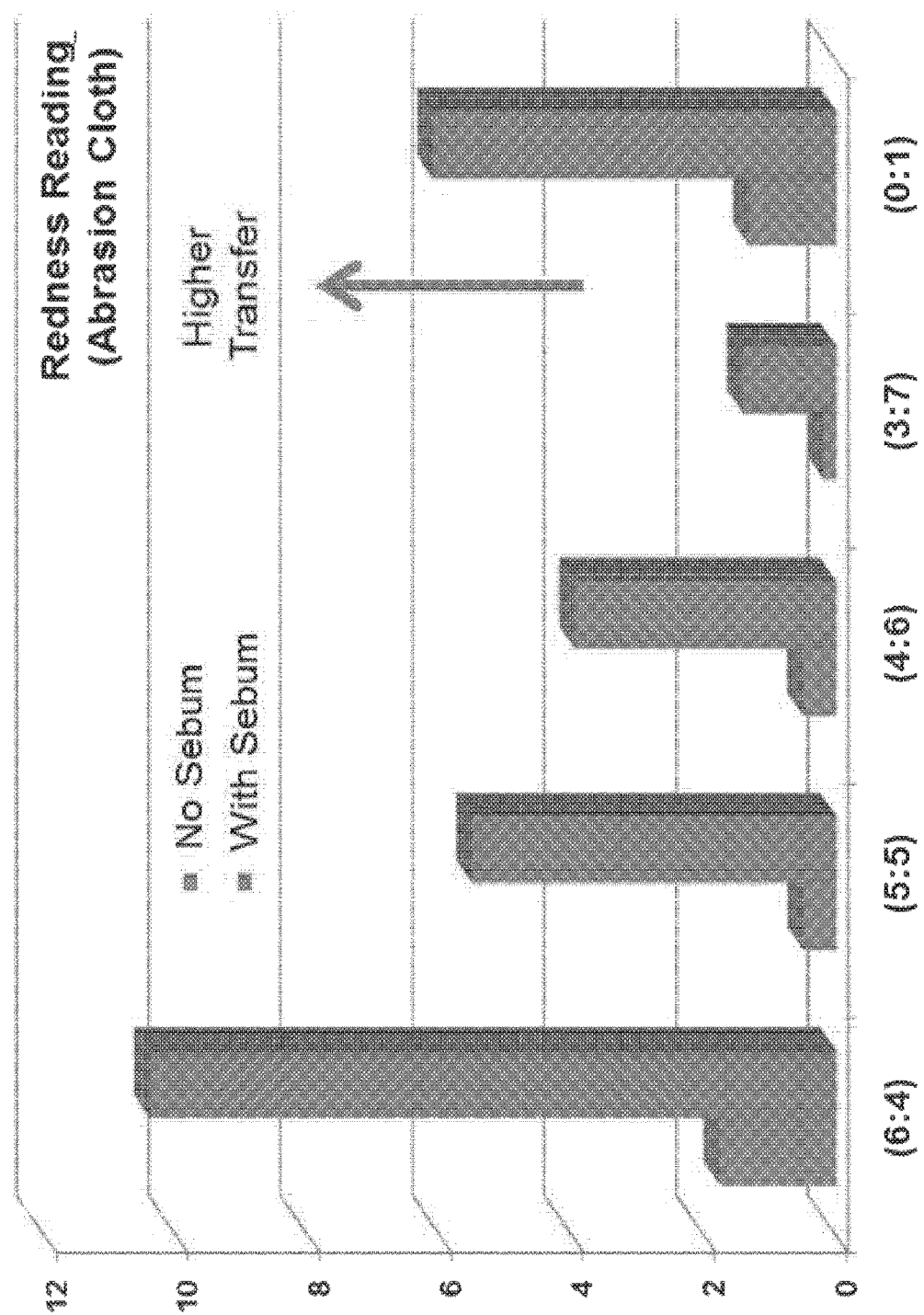
FIG. 11 is another bar graph illustrating abrasion test results of the Examples.

FIG. 11 depicts colorimeter readings on the rubbing clothes used for the examples illustrated in FIG. 10. The "a" value of L*a*b, which is associated with the color red, is most useful for determining the amount of transfer from a treated film to a rubbing cloth.

Figure 12:
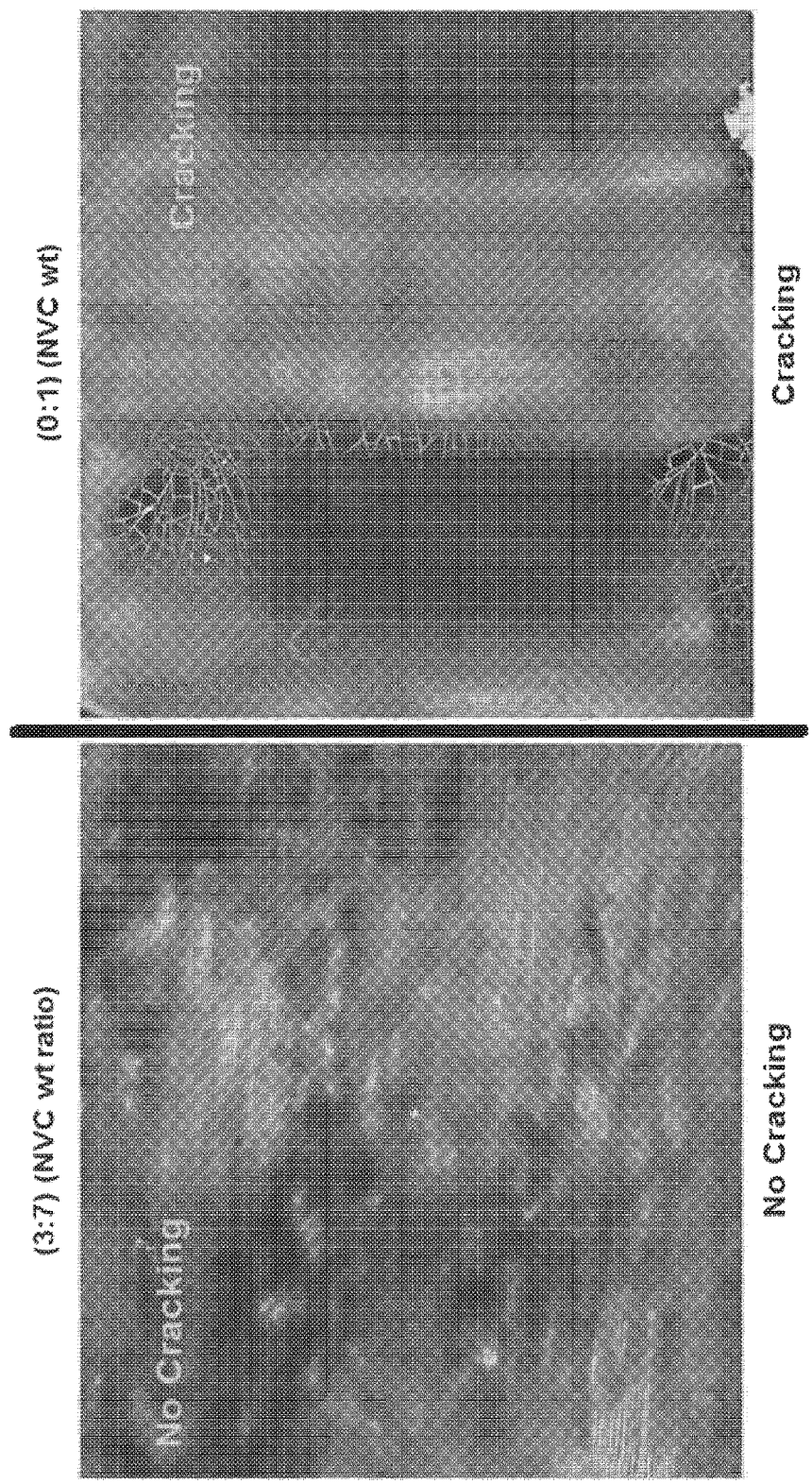
FIG. 12 is a photograph illustrating drying and cracking test results of the Examples.

FIG. 12 depicts drying and cracking test results. A 3:7 blend ratio of the silicone polyether copolymer and the acrylate copolymer is spread by finger on a collagen film (associated with left photograph). The acrylate copolymer (sans silicone polyether copolymer) is spread by finger on another collagen film (associated with right photograph). The treated films are allowed to dry and observed for cracking. As shown in FIG. 12, inclusion of the silicone polyether copolymer prevents the acrylate copolymer from cracking.

Figure 13:
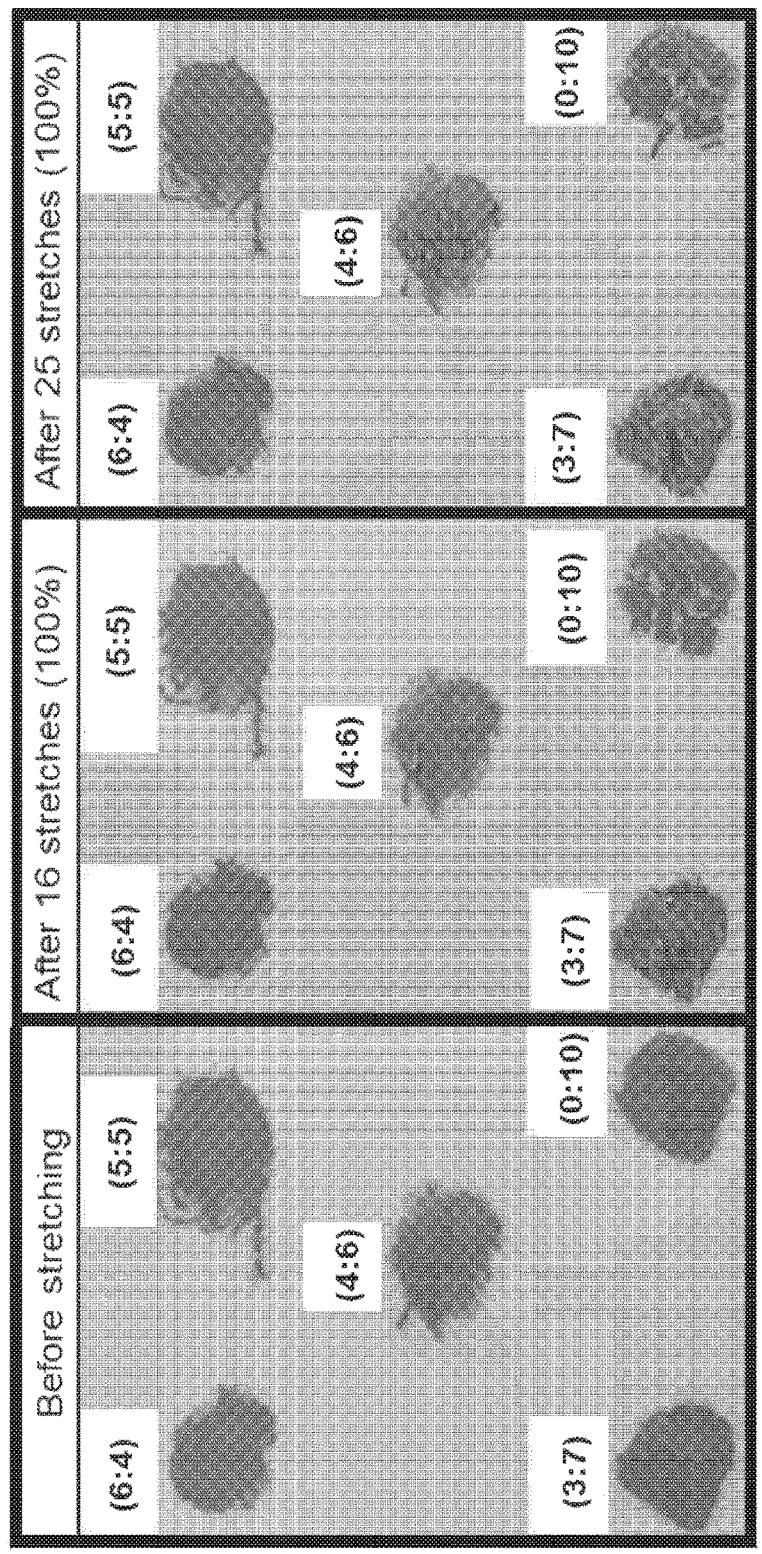
FIG. 13 is a photograph illustrating drying, stretching and cracking test results of the Examples.

FIG. 13 depicts drying, stretching, and cracking test results. Various blend ratios of the first and second components, as well as the second component sans the first component, are applied to and allowed to dry on the same rubber band. After drying, the rubber band is then stretched 16 times, followed by another 9 times for a total of 25 times. As shown in FIG. 13, inclusion of the silicone polyether copolymer at least minimizes, if not outright prevents, the acrylate copolymer from cracking. These results illustrate that incorporation of the silicone polyether copolymer allows for the acrylate copolymer films to flex.

The terms "comprising" or "comprise" are used herein in their broadest sense to mean and encompass the notions of "including", "include", "consist(ing) essentially of", and "consist(ing) of". The use of "for example", "e.g.", "such as", and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated.

The term "ambient temperature" or "room temperature" as used herein refers to a temperature of from about 20-30, ° C. Usually, "room temperature" ranges from about 20-25, ° C. All viscosity measurements referred to herein were measured at 25° C. unless otherwise indicated. Generally, as used herein a hyphen "-" or dash "-" in a range of values is "to" or "through"; a ">" is "above" or "greater-than"; a "≥" is "at least" or "greater-than or equal to"; a "<" is "below" or "less-than"; and a "≤" is "at most" or "less-than or equal to".

The term "branched" as used herein describes a polymer with >2 end groups. The term "substituted" as used in relation to another group, for example, a hydrocarbon group, means, unless indicated otherwise, one or more hydrogen atoms in the hydrocarbon group has been replaced with another substituent. Examples of such substituents include, but are not limited to, halogen atoms, such as chlorine, fluorine, bromine, and iodine; halogen atom containing groups, such as chloromethyl, perfluorobutyl, trifluoroethyl, and nonafluorohexyl; oxygen atoms; oxygen atom containing groups, such as (meth)acrylic and carboxyl; nitrogen atoms; nitrogen atom containing groups, such as amines, amino-functional groups, amido-functional groups, and cyano-functional groups; sulphur atoms; and sulphur atom containing groups, such as mercapto groups.

On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and/or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

Example 1

| Eye Shadow: Anhydrous, Ease of Spreading, Smooth Feel Formulation 02066 | | |
| --- | --- | --- |
| Ingredient | Wt. % | Trade Name/Supplier |
| Phase A | | |
| 1. Isododecane | 25.5 | |
| 2. Trimethylsiloxysilicate | 4 | DOW CORNING ® MQ-1600 SOLID RESIN |
| Phase B | | |
| 3. Dimethicone (and) Dimethicone/Vinyl Dimethicone Crosspolymer | 5 | DOW CORNING ® 3901 LIQUID SATIN BLEND |
| 4. Dimethicone (and) Dimethicone Crosspolymer | 45.5 | DOW CORNING ® EL-9140 DM SILICONE ELASTOMER BLEND |
| 5. Mica (and) Titanium Dioxide (and) Iron Oxides (and) Carmine | 20 | Cloisonne Nu-Antique Red/BASF |

Procedure

1. Mix phase A ingredients until homogeneous.
2. Mix phase B ingredients until homogeneous.
3. Add phase A to phase B.

Variations

Alternative Dow Corning ® Products have not been tested as of this printing.

Stability

Stability data for this formulation has not been established.

ATTRIBUTES

Anhydrous
Ease of Spreading
Smooth Feel

DOW CORNING ® PRODUCTS

DOW CORNING ® 3901 LIQUID SATIN BLEND
DOW CORNING ® EL-9140 DM SILICONE ELASTOMER BLEND
DOW CORNING ® MQ-1600 SOLID RESIN

What is claimed is:
1. A fluid composition comprising:
   I) a first component comprising dimethicone and dimethicone/vinyl dimethicone crosspolymer; and

II) a second component different from the first component, the second component comprising an MQ resin;
wherein the first component I) and the second component II) are present in a weight ration of from about 10:1 to about 1:10.

2. The fluid composition as set forth in any claim 1, wherein the first component I) and the second component II) are present in a weight ratio of from about 5:1 to about 1:5.

3. The fluid composition as set forth in claim 1, wherein the second component II) comprises an organosiloxane resin, the organosiloxane resin comprising siloxy units of the formula:

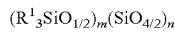

where each $R^1$ is an independently selected substituted or unsubstituted hydrocarbyl group, "m" is $\geq 4$, and "n" is $\geq 1$.

4. The fluid composition as set forth in claim 3, wherein:
i) the ratio of m/n is about 1.5 to about 1;
ii) each $R^1$ is an independently selected alkyl group having from 1-8 carbon atoms, an aryl group, a carbinol group, or an amino group; or
iii) both i) and ii).

5. The fluid composition as set forth in claim 1, further comprising a carrier fluid.

6. The fluid composition as set forth in claim 5, wherein the carrier fluid is:
i) selected from a group consisting of silicones, organic solvents, organic oils, and combinations thereof;
ii) present in an amount of from about 50 to about 99.9 wt % based on 100 parts by weight of the fluid composition; or
iii) both i) and ii).

7. The fluid composition as set forth in claim 1, wherein:
i) the fluid composition has a viscosity of at least 100 mPa·s at 23° C. and exhibits pituitous rheological properties;
ii) rheological properties of the fluid composition are determined from a plot of normal force (in Pascals) vs a perpendicular shear rate (in sec−1) and the plot has an average slope that is >3.6; or
iii) both i) and ii).

8. A personal care composition comprising the fluid composition as set forth in claim 1.

9. The fluid composition of claim 1, wherein the fluid composition comprises an acrylate copolymer.

10. The fluid composition of claim 9, wherein the acrylate copolymer is a carbosiloxane dendrimer.

* * * * *